(12) United States Patent
Joun et al.

(10) Patent No.: US 11,773,426 B2
(45) Date of Patent: Oct. 3, 2023

(54) MULTIPLEX NUCLEIC ACID AMPLIFICATION

(71) Applicant: LIFE TECHNOLOGIES CORPORATION, Carlsbad, CA (US)

(72) Inventors: David Joun, San Francisco, CA (US); Chieh-Yuan Li, Hayward, CA (US); Brian Reed, Woodbridge, CT (US); Craig Obergfell, San Diego, CA (US); Devin Dressman, Pittsburgh, PA (US); Abraham Rosenbaum, Passaic, NJ (US); Scott Benson, Alameda, CA (US); Andi Broka, Carlsbad, CA (US); Srinka Ghosh, San Francisco, CA (US)

(73) Assignee: Life Technologies Corporation, Carlsbad, CA (US)

( * ) Notice: Subject to any disclaimer, the term of this patent is extended or adjusted under 35 U.S.C. 154(b) by 681 days.

(21) Appl. No.: 16/514,814

(22) Filed: Jul. 17, 2019

(65) Prior Publication Data
US 2019/0338343 A1 Nov. 7, 2019

Related U.S. Application Data

(63) Continuation of application No. 14/736,509, filed on Jun. 11, 2015.
(Continued)

(51) Int. Cl.
*C12Q 1/68* (2018.01)
*C12Q 1/6806* (2018.01)
*C12Q 1/6844* (2018.01)

(52) U.S. Cl.
CPC ......... *C12Q 1/6806* (2013.01); *C12Q 1/6844* (2013.01); *C12Q 1/6846* (2013.01)

(58) Field of Classification Search
None
See application file for complete search history.

(56) References Cited

U.S. PATENT DOCUMENTS 6,297,017 B1 10/2001 Schmidt et al.
6,500,620 B2 12/2002 Yu et al.
(Continued)

FOREIGN PATENT DOCUMENTS

EP 3155127 A1 4/2017
WO WO-9922030 A1 5/1999
(Continued)

OTHER PUBLICATIONS

Tewhey et al. (Nature Biotechnology, 2009, 27(11):1025-1031).*
(Continued)

*Primary Examiner* — Stephanie K Mummert

(57) ABSTRACT

In some embodiments, the disclosure relates generally to compositions, comprising a single reaction mixture containing a plurality of different populations of discrete supports, and a plurality of different populations of target nucleic acids. The single reaction mixture can contain a first population of beads; a second population of beads; a first population of target nucleic acids, where at least two different target nucleic acids in the first population of target nucleic acids can bind to a bead in the first population of beads; and a second population of target nucleic acids, where at least two different target nucleic acids in the second population of target nucleic acids can bind to a bead in the second population of beads. The single reaction mixture can be employed to monoclonally amplify the first target nucleic acids on the first beads, and monoclonally amplify the second target nucleic acids on the second beads.

20 Claims, 9 Drawing Sheets

Specification includes a Sequence Listing.

Related U.S. Application Data

(60) Provisional application No. 62/012,213, filed on Jun. 13, 2014, provisional application No. 62/113,257, filed on Feb. 6, 2015.

(56) References Cited

U.S. PATENT DOCUMENTS

| | | | |
|---|---|---|---|
| 6,913,884 | B2 | 7/2005 | Stuelpnagel et al. |
| 7,285,384 | B2 | 10/2007 | Fan et al. |
| 7,459,273 | B2 | 12/2008 | Jones et al. |
| 7,803,537 | B2 | 9/2010 | Fan et al. |
| 7,842,457 | B2 * | 11/2010 | Berka .................. C12Q 1/6865 435/6.16 |
| 7,892,796 | B2 | 2/2011 | Grenier et al. |
| 8,217,160 | B2 | 7/2012 | Grenier et al. |
| 8,288,103 | B2 | 10/2012 | Oliphant et al. |
| 8,518,671 | B2 | 8/2013 | Grenier et al. |
| 8,628,918 | B2 | 1/2014 | Luo et al. |
| 8,685,753 | B2 | 4/2014 | Martin et al. |
| 9,309,557 | B2 | 4/2016 | Li et al. |
| 9,309,558 | B2 | 4/2016 | Li et al. |
| 9,309,566 | B2 | 4/2016 | Li et al. |
| 9,334,531 | B2 | 5/2016 | Li et al. |
| 9,371,557 | B2 | 6/2016 | Li et al. |
| 9,476,080 | B2 | 10/2016 | Li et al. |
| 10,113,195 | B2 | 10/2018 | Li et al. |
| 10,329,544 | B2 | 6/2019 | Li et al. |
| 2010/0015668 | A1 | 1/2010 | Staehler et al. |
| 2010/0112558 | A1 | 5/2010 | Gao et al. |
| 2013/0244882 | A1 | 9/2013 | Oliphant et al. |
| 2014/0051593 | A1 | 2/2014 | Taft et al. |
| 2014/0141418 | A1 | 5/2014 | Park et al. |
| 2015/0361481 | A1 | 12/2015 | Joun et al. |
| 2017/0067098 | A1 | 3/2017 | Li et al. |
| 2019/0338258 | A1 | 11/2019 | Li et al. |

FOREIGN PATENT DOCUMENTS

| | | |
|---|---|---|
| WO | WO-2005010145 A2 | 2/2005 |
| WO | WO-2008076842 A2 | 6/2008 |
| WO | WO-2010028366 A2 | 3/2010 |
| WO | WO-2015191815 A1 | 12/2015 |

OTHER PUBLICATIONS

Wang et al. (Molecules, 2011, 16:7365-7376) (Year: 2011).*
Kojima et al. (Nucleic Acids Research 2005, 33(17):e150, p. 1-9) (Year: 2005).*
Bentley et al. (Tissue Antigens, 2009, 74:393-403) (Year: 2009).*
Moonsamy et al. (Tissue Antigens, 2013, 81:141-149) (Year: 2013).*
Turner et al. (Jul. 2006, Fusion PCR protocol, p. 1-5) (Year: 2006).*
Binladen, Jonas et al., "The Use of Coded PCR Primers Enables High-Throughput Sequencing of Multiple Homolog Amplification Products by 454 Parallel Sequencing", PLoS ONE, 2(2):, 2007, e197.
Dressman, D et al., "Transforming single DNA molecules into fluorescent magnetic particles for detection and enumeration of genertic vari", PNAS, vol. 100 (15), 2003, pp. 8817-8822.
Dumonceaux et al. (J Clin Microbial, 2009, 4067-4077) (Year: 2009).
Kojima, T. et al., "PCR amplification from single DNA molecules on magnetic beads in emulsion: application for high-throughput screening of transcription factor targets", Nucleic Acids Research, vol. 33 (17) e150, Oct. 6, 2005, 9 Pages.
Ng et al. (Biosensors and Bioelectronics, 2008, vol. 23, p. 803-810).
PCT/US2015/035265, International Search Report and Written Opinion dated Sep. 14, 2015, 13 Pages.
Shapero, Michael et al., "SNP Genotyping by Multiplexed Solid-Phase Amplification and Fluorescent Minisequencing", Genome Research, 11, 2001, 1926-1934.
Xu, Ming Y. et al., "Dual primer emulsion PCR for next-generation DNA sequencing", BioTechniques, vol. 48, No. 5, 2010, 409-412.

* cited by examiner

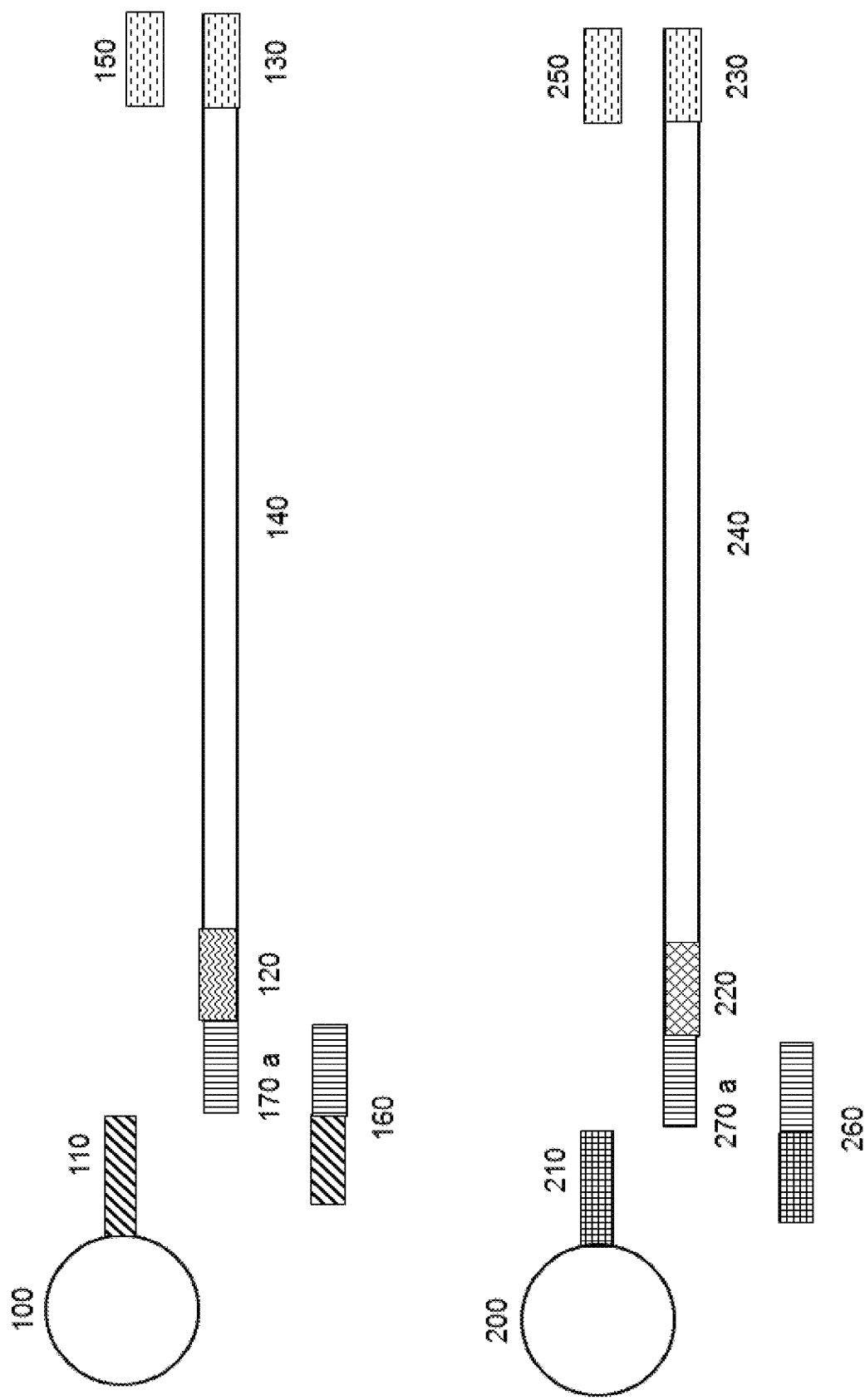

SEQUENCE LISTING

<160> NUMBER OF SEQ ID NOS: 31

<210> SEQ ID NO 1
<211> LENGTH: 32
<212> TYPE: DNA
<213> ORGANISM: Artificial Sequence
<220> FEATURE:
<223> OTHER INFORMATION: Synthetic primer: AV1

<400> SEQUENCE: 1
gcacacattc agagtcagca gctcagcatc at                32

<210> SEQ ID NO 2
<211> LENGTH: 32
<212> TYPE: DNA
<213> ORGANISM: Artificial Sequence
<220> FEATURE:
<223> OTHER INFORMATION: Synthetic primer: AV2

<400> SEQUENCE: 2
ttaggagatg ttcatgcaga ctcacgatca gt                                32

<210> SEQ ID NO 3
<211> LENGTH: 32
<212> TYPE: DNA
<213> ORGANISM: Artificial Sequence
<220> FEATURE:
<223> OTHER INFORMATION: Synthetic primer: AV3

<400> SEQUENCE: 3
agtcacttat catcggtggt acgcagctca tt                                32

<210> SEQ ID NO 4
<211> LENGTH: 34
<212> TYPE: DNA
<213> ORGANISM: Artificial Sequence
<220> FEATURE:
<223> OTHER INFORMATION: Synthetic primer: AV4

<400> SEQUENCE: 4
attcgagctg ttcatctgta tcttgcgcta ccaa                              34

<210> SEQ ID NO 5
<211> LENGTH: 32
<212> TYPE: DNA
<213> ORGANISM: Artificial Sequence
<220> FEATURE:
<223> OTHER INFORMATION: Synthetic primer: AV5

<400> SEQUENCE: 5
gaatctgttc tcactattca cgctggagga gt                                32

<210> SEQ ID NO 6
<211> LENGTH: 35
<212> TYPE: DNA
<213> ORGANISM: Artificial Sequence
<220> FEATURE:
<223> OTHER INFORMATION: Synthetic primer: AV6

<400> SEQUENCE: 6
gtaactcgat caggtcacac gaccgttctc agcat                             35

<210> SEQ ID NO 7
<211> LENGTH: 33
<212> TYPE: DNA
<213> ORGANISM: Artificial Sequence
<220> FEATURE:
<223> OTHER INFORMATION: Synthetic primer: AV7

<400> SEQUENCE: 7
gatttcgcag ctaaccttgg tggaagctct cat                               33

<210> SEQ ID NO 8
<211> LENGTH: 32
<212> TYPE: DNA
<213> ORGANISM: Artificial Sequence
<220> FEATURE:
<223> OTHER INFORMATION: Synthetic primer: AV8

<400> SEQUENCE: 8
cttgaactac accactctga tgtgccagtc ta                                32

<210> SEQ ID NO 9

```
<211> LENGTH: 35
<212> TYPE: DNA
<213> ORGANISM: Artificial Sequence
<220> FEATURE:
<223> OTHER INFORMATION: Synthetic primer: AV9

<400> SEQUENCE: 9
tatcgagcta gtgcgtgcta tcagaaccta tcagt                                35

<210> SEQ ID NO 10
<211> LENGTH: 33
<212> TYPE: DNA
<213> ORGANISM: Artificial Sequence
<220> FEATURE:
<223> OTHER INFORMATION: Synthetic primer: AV10

<400> SEQUENCE: 10
acgtcgacac tagctacctg tcagctacgt gta                                  33

<210> SEQ ID NO 11
<211> LENGTH: 52
<212> TYPE: DNA
<213> ORGANISM: Artificial Sequence
<220> FEATURE:
<223> OTHER INFORMATION: Synthetic primer: ML1a

<400> SEQUENCE: 11
ccactacgcc tccgctttcc tctctatggg cagtcggtga agctctcatg at             52

<210> SEQ ID NO 12
<211> LENGTH: 54
<212> TYPE: DNA
<213> ORGANISM: Artificial Sequence
<220> FEATURE:
<223> OTHER INFORMATION: Synthetic primer: ML1b
<220> FEATURE:
<221> NAME/KEY: modified_base
<222> LOCATION: (53)..(54)
<223> OTHER INFORMATION: phosphorothiolate, phosphorothioate, and/or
      phosphoramidate linkage

<400> SEQUENCE: 12
atcatgagag cttcaccgac tgcccataga gaggaaagcg gaggcgtagt ggtt           54

<210> SEQ ID NO 13
<211> LENGTH: 52
<212> TYPE: DNA
<213> ORGANISM: Artificial Sequence
<220> FEATURE:
<223> OTHER INFORMATION: Synthetic primer: ML2a

<400> SEQUENCE: 13
ccactacgcc tccgctttcc tctctatggg cagtcggtgt gccagtctag at             52

<210> SEQ ID NO 14
<211> LENGTH: 54
<212> TYPE: DNA
<213> ORGANISM: Artificial Sequence
<220> FEATURE:
<223> OTHER INFORMATION: Synthetic primer: ML2b
<220> FEATURE:
<221> NAME/KEY: modified_base
<222> LOCATION: (53)..(54)
<223> OTHER INFORMATION: phosphorothiolate, phosphorothioate, and/or
      phosphoramidate linkage

<400> SEQUENCE: 14
atctagactg gcacaccgac tgcccataga gaggaaagcg gaggcgtagt ggtt           54
```

<210> SEQ ID NO 15
<211> LENGTH: 52
<212> TYPE: DNA
<213> ORGANISM: Artificial Sequence
<220> FEATURE:
<223> OTHER INFORMATION: Synthetic primer: ML3a

<400> SEQUENCE: 15
ccactacgcc tccgctttcc tctctatggg cagtcggtga cctatcagtg at    52

<210> SEQ ID NO 16
<211> LENGTH: 54
<212> TYPE: DNA
<213> ORGANISM: Artificial Sequence
<220> FEATURE:
<223> OTHER INFORMATION: Synthetic primer: ML3b
<220> FEATURE:
<221> NAME/KEY: modified_base
<222> LOCATION: (53)..(54)
<223> OTHER INFORMATION: phosphorothiolate, phosphorothioate, and/or
      phosphoramidate linkage

<400> SEQUENCE: 16
atcactgata ggtcaccgac tgcccataga gaggaaagcg gaggcgtagt ggtt    54

<210> SEQ ID NO 17
<211> LENGTH: 52
<212> TYPE: DNA
<213> ORGANISM: Artificial Sequence
<220> FEATURE:
<223> OTHER INFORMATION: Synthetic primer: ML4a

<400> SEQUENCE: 17
ccactacgcc tccgctttcc tctctatggg cagtcggtgg ctacgtgtag at    52

<210> SEQ ID NO 18
<211> LENGTH: 54
<212> TYPE: DNA
<213> ORGANISM: Artificial Sequence
<220> FEATURE:
<223> OTHER INFORMATION: Synthetic primer: ML4b
<220> FEATURE:
<221> NAME/KEY: modified_base
<222> LOCATION: (53)..(54)
<223> OTHER INFORMATION: phosphorothiolate, phosphorothioate, and/or
      phosphoramidate linkage

<400> SEQUENCE: 18
atctacacgt agccaccgac tgcccataga gaggaaagcg gaggcgtagt ggtt    54

<210> SEQ ID NO 19
<211> LENGTH: 52
<212> TYPE: DNA
<213> ORGANISM: Artificial Sequence
<220> FEATURE:
<223> OTHER INFORMATION: Synthetic primer: ML5a

<400> SEQUENCE: 19
ccactacgcc tccgctttcc tctctatggg cagtcggtgt gccagtctag at    52

<210> SEQ ID NO 20
<211> LENGTH: 54
<212> TYPE: DNA
<213> ORGANISM: Artificial Sequence
<220> FEATURE:
<223> OTHER INFORMATION: Synthetic primer: ML5b
<220> FEATURE:

<221> NAME/KEY: modified_base
<222> LOCATION: (53)..(54)
<223> OTHER INFORMATION: phosphorothiolate, phosphorothioate, and/or
      phosphoramidate linkage

<400> SEQUENCE: 20
atctagactg gcacaccgac tgcccataga gaggaaagcg gaggcgtagt ggtt        54

<210> SEQ ID NO 21
<211> LENGTH: 52
<212> TYPE: DNA
<213> ORGANISM: Artificial Sequence
<220> FEATURE:
<223> OTHER INFORMATION: Synthetic primer: ML6a

<400> SEQUENCE: 21
ccactacgcc tccgctttcc tctctatggg cagtcggtgg ctacgtgtag at        52

<210> SEQ ID NO 22
<211> LENGTH: 54
<212> TYPE: DNA
<213> ORGANISM: Artificial Sequence
<220> FEATURE:
<223> OTHER INFORMATION: Synthetic primer: ML6b
<220> FEATURE:
<221> NAME/KEY: modified_base
<222> LOCATION: (53)..(54)
<223> OTHER INFORMATION: phosphorothiolate, phosphorothioate, and/or
      phosphoramidate linkage

<400> SEQUENCE: 22
atctacacgt agccaccgac tgcccataga gaggaaagcg gaggcgtagt ggtt        54

<210> SEQ ID NO 23
<211> LENGTH: 52
<212> TYPE: DNA
<213> ORGANISM: Artificial Sequence
<220> FEATURE:
<223> OTHER INFORMATION: Synthetic primer: AV1/ML1

<400> SEQUENCE: 23
gcacacattc agagtcagca gctcagcatc atgcagtcgg tgaagctctc at        52

<210> SEQ ID NO 24
<211> LENGTH: 52
<212> TYPE: DNA
<213> ORGANISM: Artificial Sequence
<220> FEATURE:
<223> OTHER INFORMATION: Synthetic primer: AV2/ML2

<400> SEQUENCE: 24
ttaggagatg ttcatgcaga ctcacgatca gtgcagtcgg tgtgccagtc ta        52

<210> SEQ ID NO 25
<211> LENGTH: 52
<212> TYPE: DNA
<213> ORGANISM: Artificial Sequence
<220> FEATURE:
<223> OTHER INFORMATION: Synthetic primer: AV3/ML3

<400> SEQUENCE: 25
agtcacttat catcggtggt acgcagctca ttgcagtcgg tgacctatca gt        52

<210> SEQ ID NO 26
<211> LENGTH: 54
<212> TYPE: DNA
<213> ORGANISM: Artificial Sequence

```
<220> FEATURE:
<223> OTHER INFORMATION: Synthetic primer: AV4/ML4

<400> SEQUENCE: 26
attcgagctg ttcatctgta tcttgcgcta ccaagcagtc ggtggctacg tgta         54

<210> SEQ ID NO 27
<211> LENGTH: 52
<212> TYPE: DNA
<213> ORGANISM: Artificial Sequence
<220> FEATURE:
<223> OTHER INFORMATION: Synthetic primer: AV5/ML5

<400> SEQUENCE: 27
gaatctgttc tcactattca cgctggagga gtgcagtcgg tgtgccagtc ta           52

<210> SEQ ID NO 28
<211> LENGTH: 55
<212> TYPE: DNA
<213> ORGANISM: Artificial Sequence
<220> FEATURE:
<223> OTHER INFORMATION: Synthetic primer: AV6/ML6

<400> SEQUENCE: 28
gtaactcgat caggtcacac gaccgttctc agcatgcagt cggtggctac gtgta        55

<210> SEQ ID NO 29
<211> LENGTH: 53
<212> TYPE: DNA
<213> ORGANISM: Artificial Sequence
<220> FEATURE:
<223> OTHER INFORMATION: Synthetic primer: B/P1

<400> SEQUENCE: 29
cctatcccct gtgtgccttg gcagtctcag cctctctatg ggcagtcggt gat          53

<210> SEQ ID NO 30
<211> LENGTH: 41
<212> TYPE: DNA
<213> ORGANISM: Artificial Sequence
<220> FEATURE:
<223> OTHER INFORMATION: Synthetic primer: P1(a adaptor)

<400> SEQUENCE: 30
ccactacgcc tccgctttcc tctctatggg cagtcggtga t                       41

<210> SEQ ID NO 31
<211> LENGTH: 43
<212> TYPE: DNA
<213> ORGANISM: Artificial Sequence
<220> FEATURE:
<223> OTHER INFORMATION: Synthetic primer: P1(b adaptor)
<220> FEATURE:
<221> NAME/KEY: modified_base
<222> LOCATION: (42)..(43)
<223> OTHER INFORMATION: phosphorothiolate, phosphorothioate, and/or
      phosphoramidate linkage

<400> SEQUENCE: 31
atcaccgact gcccatagag aggaaagcgg aggcgtagtg gtt                     43
```

MULTIPLEX NUCLEIC ACID AMPLIFICATION

This application is a continuation of U.S. application Ser. No. 14/736,509, filed Jun. 11, 2015, which claims priority to U.S. Provisional Application No. 62/012,213, filed Jun. 13, 2014, and to U.S. Provisional Application No. 62/113,257, filed Feb. 6, 2015, each of which applications is incorporated by reference in its entirety herein.

This application hereby incorporates by reference the material of the electronic Sequence Listing filed concurrently herewith. The material in the electronic Sequence Listing is submitted as a text (.txt) file entitled "LT00912CON ST25.txt" created on Jul. 17, 2019, which has a file size of 8 KB, and is herein incorporated by reference in its entirety.

Throughout this application various publications, patents, and/or patent applications are referenced. The disclosures of the publications, patents and/or patent applications in their entireties are hereby incorporated by reference into this application in order to more fully describe the state of the art to which this invention pertains.

Many nucleic acid analysis platforms, including "next-gen sequencing" (NGS), PCR and/or genetic analysis platforms, utilize beads or single surfaces (e.g., arrays) that are attached with one or more monoclonal amplicons (e.g., templated beads or templated arrays). These templated beads and/or arrays are typically generated via amplification-based methods. For example, templated beads can be formed using methods such as emulsion PCR, which employs water-in-oil emulsions. This type of emulsion forms numerous aqueous micro-droplets that are partitioned from each other by an oil phase. Ideally, the micro-droplets contain a single template nucleic acid and one bead, along with enzymes, nucleotides and other reagents for conducting a nucleic acid amplification reaction. Each micro-droplet serves as a separate compartment within which clonal amplification occurs. When such micro-droplets are incubated under suitable amplification conditions, the individual micro-droplets yield one bead attached to monoclonal amplicons of the template nucleic acid. In other methods, nucleic acid templates can be mixed with beads and amplified clonally onto beads without need for emulsions. See, e.g., U.S. Ser. No. 13/328,844 (U.S. Patent Publication No. 20120156728) and Ser. No. 13/842,296 (U.S. Patent Publication No. 20130225421), incorporated by reference herein in their entireties. However, such methods typically require tightly controlled dilution and/or careful adjustment of the relative concentrations of the template nucleic acids and beads in order to dilute the number of nucleic acid molecules such that only one template nucleic acid molecule is amplified onto any given bead. This can be challenging to achieve. For example, at least some of the micro-droplets in an emulsion will often contain multiple different template nucleic acids, which leads to formation of polyclonal beads that might not yield useful information in a downstream assay. Other micro-droplets may contain one template nucleic acid molecule and multiple beads, which leads to multiple beads each attached to monoclonal amplicons of the same template nucleic acid, which results in duplicate sequencing reads. Polyclonality and duplicate reads are significant problems for interpretation of next gen sequencing data. There is a need for improved nucleic acid amplification methods for clonal amplification of multiple templates in parallel with higher yield and throughput. There is also a need for clonal amplification methods that avoid the need for limiting dilution, and methods that allow use of higher effective concentrations of templates and primers within the amplification reaction mixture while sufficiently preserving clonality.

BRIEF DESCRIPTION OF THE DRAWINGS

FIG. 1 also depicts one bead from a second plurality of second types of beads (200) attached with a second capture primer (210), one target nucleic acid from a second population of target nucleic acids (240) that includes a third adaptor (220) and a fourth adaptor (230), and a second reverse primer (250). The first and second beads, the first and second target nucleic acids, and the first and second reverse primers can be contained in a single reaction mixture.

FIG. 2 also depicts one bead from a second plurality of second types of beads (200) attached with a second capture primer (210), one target nucleic acid from a second population of target nucleic acids (240) that includes a third adaptor (220) and a fourth adaptor (230), a second reverse primer (250), and a second fusion primer (260). The first and second beads, the first and second target nucleic acids, the first and second reverse primers, and the first and second fusion primers can be contained in a single reaction mixture.

FIG. 3A also depicts one target nucleic acid from a second population of target nucleic acids (240) that includes a third adaptor (220) and a fourth adaptor (230), and a second conversion primer (270 *a/b*) which can be a fusion primer. Optionally, the second conversion primer (270 *a/b*) includes a sequence (270*a*) that is not contained in, or is not complementary to, a portion of the third adaptor (220). In another exemplary embodiment, the second conversion primer (270 *a/b*) can be used in a primer extension reaction to append a conversion adaptor sequence (270*a*) to the third adaptor (220) to yield a second nucleic acid molecule having sequences 270*a*, 220, 240 and 230. The first and second target nucleic acids, and the first and second conversion primers can be contained in a single reaction mixture.

FIG. 3B is a schematic that depicts one embodiment of the compositions, as well as related, systems, methods, kits and apparatuses for nucleic acid synthesis. One bead from a first plurality of first types of beads (100) attached with a first capture primer (110), one target nucleic acid from a first population of target nucleic acids (140) that includes a first conversion adaptor (170a) and a first adaptor (120) and a second adaptor (130), a first reverse primer (150), and a first fusion primer (160). FIG. 3B also depicts one bead from a second plurality of second types of beads (200) attached with a second capture primer (210), one target nucleic acid from a second population of target nucleic acids (240) that includes second conversion adaptor (270a) and a third adaptor (220) and a fourth adaptor (230), a second reverse primer (250), and a second fusion primer (260). The first and second beads, the first and second target nucleic acids, the first and second reverse primers, and the first and second fusion primers can be contained in a single reaction mixture.

DETAILED DESCRIPTION

Figure 1:
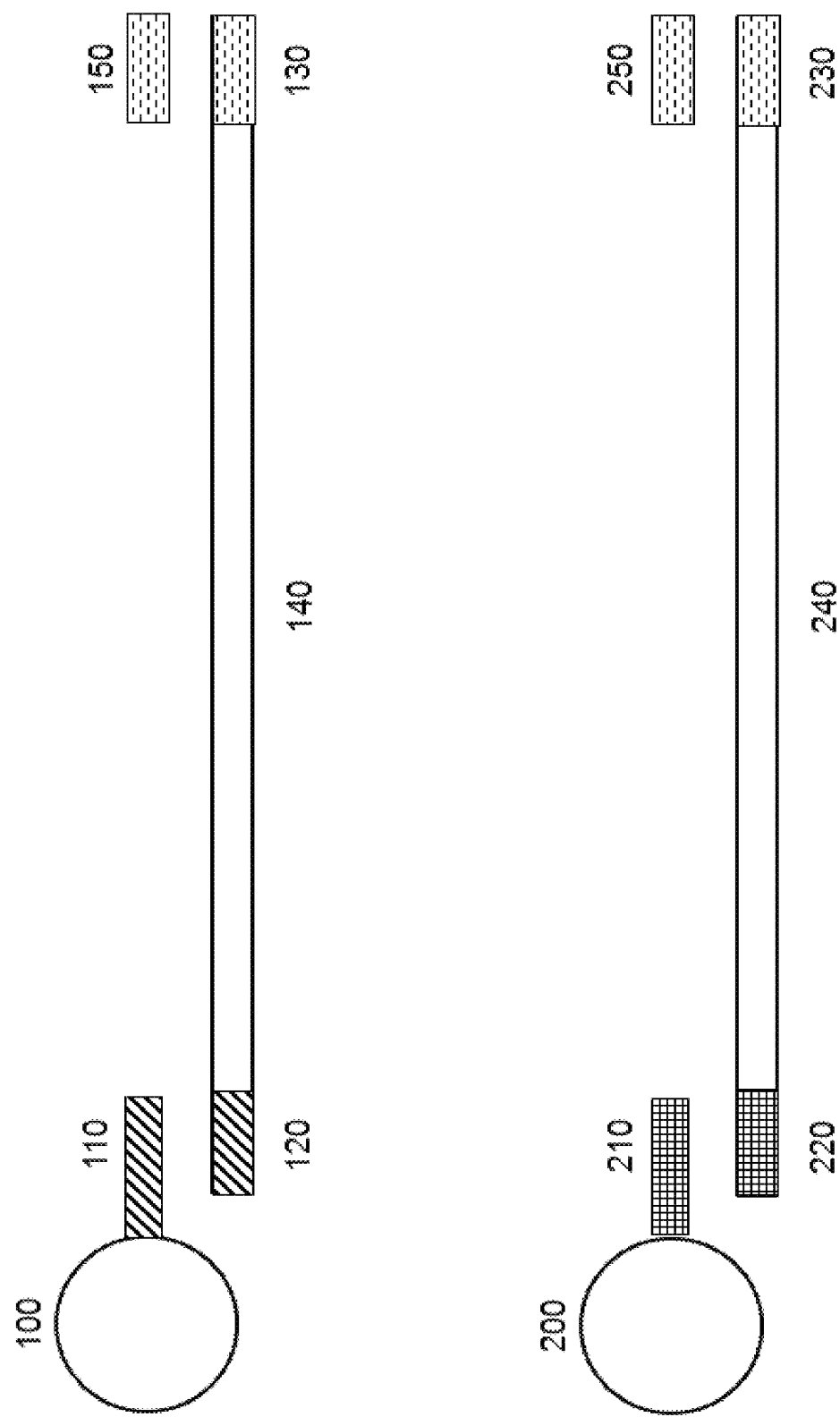
FIG. 1 is a schematic that depicts one embodiment of the compositions, as well as related, systems, methods, kits and apparatuses for nucleic acid synthesis. One bead from a first plurality of first types of beads (100) attached with a first capture primer (110), one target nucleic acid from a first population of target nucleic acids (140) that includes a first adaptor (120) and a second adaptor (130), and a first reverse primer (150).

In some embodiments, the disclosure relates generally to methods, as well as related, systems, compositions, kits and apparatuses, for amplifying different template nucleic acids with different discrete supports (e.g., beads), or onto different discrete regions of a single support (e.g., arrays). The advantages provided by the methods, as well as related, systems, compositions, kits and apparatuses include generating fewer polyclonal amplicons while producing more monoclonal amplicons (or at least substantially monoclonal amplicons). The advantages also include reducing duplicate sequencing reads.

In some embodiments, the disclosure relates generally to methods, as well as related, systems, compositions, kits and apparatuses, for amplifying different target nucleic acids by one or more rounds of nucleic acid synthesis. In some embodiments, the methods can include amplifying multiple different target nucleic acids onto beads, to produce a plurality of templated beads, where each bead is attached to a substantially monoclonal population of one of the target nucleic acids. In some embodiments, the methods, as well as related, systems, compositions, kits and apparatuses, comprise amplifying the different target nucleic acids with multiple beads, in parallel, in a single reaction mixture. In some embodiments, the single reaction mixture can be compartmentalized (e.g., via emulsion), or alternatively the single reaction mixture can lack compartmentalization. In some embodiments, the methods include reducing the production of polyclonal amplicons within the reaction mixture. The reducing optionally includes increasing the average distance between the individual target nucleic acids to be amplified within the single reaction mixture. In some embodiments, reducing the production of polyclonal amplicons can include increasing the volume of the reaction mixture. It is understood that applying suitable techniques, such as those described herein, can result in both increasing the volume of the reaction mixture and increasing the average distance between individual target nucleic acids to be amplified.

In some embodiments, the average distance between target nucleic acids within the reaction mixture and/or the volume of the reaction mixture can be increased by adding additional components to the reaction mixture. In some embodiments, the additional components can include one or more discrete physical components, such as particles, beads, supports, and the like. In some embodiments, the discrete physical components can be useful in maintaining the separation between two different target nucleic acids to be amplified. In some embodiments, the discrete physical components can be useful in increasing the effective distance between two target nucleic acids to be amplified. "Effective distance", as used herein, refers to the average path length taken by a first target nucleic acid to travel from its current location to the location of a second target nucleic acid within the same reaction mixture.

In some embodiments, the additional components in the reaction mixture can bind to migrating or diffusible target nucleic acids. In some embodiments, the additional components can bind non-specifically to migrating or diffusible target nucleic acids. In some embodiments, the additional components can bind to one or more specific nucleotide sequences on at least a portion of the migrating or diffusible target nucleic acids. In some embodiments, the sequence-specificity of the nucleotide sequence binding of the additional components can be provided by one or more capture primers. The capture primers are optionally attached to one or more beads, or to one or more locations on a surface. In some embodiments, the capture primers are attached to at least one of the additional components in the reaction mixture. In some embodiments, the capture primers include sequences that are complementary to at least a portion of the target nucleic acids. In some embodiments, the capture primers attached to or otherwise associated with the beads, surface and/or additional components are random or degenerate capture primers, such that the random or degenerate primers are able to bind a plurality of complementary sequence portions on migrating or diffusible target nucleic acids. In some embodiments, the capture primers attached to the beads, surface and/or additional components are capable of template-directed elongation. For example, the capture primers optionally have a terminal 3' OH group. In some embodiments, the capture primers include an extendible 3' terminal end. In some embodiments, the capture primers attached to the additional components are incapable of template-directed elongation, such as by modification of the 3'-hydroxyl group on the 3' terminal nucleotide of the oligonucleotides. In this manner, the extension-incapable primer can bind to migrating or diffusible target nucleic acid, either in a sequence-specific or sequence-non-specific manner, but because they are not capable of further template-directed elongation they will not contribute to further amplification that may lead to polyclonality. In some embodiments, the 3' terminal nucleotide of a capture primer is a dideoxynucleotide, such that the capture primer is elongation-incompetent. In some embodiments these elongation-incompetent capture primers are modified, such as by modified internucleotide linkages (e.g., thiophosphate) or blocking groups, so as to be resistant to exonucleases or proof-reading, such as 3'-5' exonuclease activity. In some embodiments, one or more capture primers can be attached to a particle, bead, or support, where the capture primer binds selectively, or non-selectively, to a target nucleic acid, and where the capture primer is capable of supporting a primer extension reaction.

Without intending to be bound by any particular model or theory, by adding the additional components (e.g., beads, particles or supports) described above to the amplification reaction mixture, the additional components serve to surround and separate the target nucleic acids from each other, thereby increasing the effective distance between the individual target nucleic acid molecules, and thus increasing the actual distance that migrating target nucleic acids must traverse to encounter another template location, which may result in polyclonality. In some embodiments, the presence of the additional components may also physically impede or block the migration of target nucleic acids within the reaction mixture, since the additional components are typically impermeable to migrating target nucleic acids. In some embodiments, the additional components are essentially impermeable to the migrating target nucleic acids as the components are of a different phase of matter (e.g. solid or gas) than the reaction mixture (e.g. liquid).

In some embodiments, the addition of the additional components, such as beads, capture primers and/or adaptors to the reaction mixture can serve to reduce or eliminate target nucleic acid migration and polyclonality in small volumes of reaction mixtures. In particular, reducing the volume of the amplification reaction mixture may be desirable in certain embodiments as it can improve efficiency of the reaction, or reduce the amount of needed reagents, or reduce the size of the reaction vessel, or other advantages or any combination thereof. However, reducing the volume may also decrease the distance between different template molecules in the reaction mixture, thereby potentially increasing the problem of target nucleic acid migration and hence polyclonality. Thus, in some embodiments, by also introducing the additional components as described herein, the migration of target nucleic acids that may cause polyclonality can be reduced, mitigated or prevented despite the small reaction volume as described herein.

In some embodiments, the addition of additional components described above to the reaction mixture, which contains the different target nucleic acids to be amplified, serves to increase the total volume of the reaction volume. In such embodiments, and without intending to be bound by any model or theory, increasing the volume may increase the mean distance between any two or more different target nucleic acids in the reaction mixture. In this manner, by increasing the mean distance, the likelihood of migrating target molecules traversing the distance between different target molecules, and thus reduce, mitigate or prevent polyclonality from amplification of different target nucleic acids at a given amplification location.

The disclosed methods (and related compositions, systems, kits and reagents) can offer several advantages as compared to conventional amplification methods, including emPCR. For example, conventional PCR workflows are time-consuming, and waste equipment and reagents as compared to the disclosed methods. For example, to conduct multiplex sequencing on a high throughput system, separate batches of templated beads must be prepared (each batch being different from the other batches), which requires setting-up multiple amplification reaction mixtures in separate reaction vessels, each vessel containing different beads and/or different target nucleic acids and/or separate reagents. The resulting separate batches of different types of templated beads are pooled together to make a mixture. The throughput of each separate amplification reaction is typically limited by Poisson statistics. For example, the proportion of productive droplets in an emPCR reaction (including the proportion of droplets yielding monoclonal or substantially monoclonal amplified populations, or the proportion of droplets yielding monoclonal or substantially monoclonal templated beads) is typically limited according to Poisson statistics to the number of droplets that receive a single template nucleic acid.

In contrast, the nucleic acid synthesis methods, according to the present teachings, provide advantages not offered by the conventional amplification methods. The nucleic acid synthesis methods yield a simplified workflow, from the bead templating step to the sequencing step, because a mixture of different types of templated beads is prepared in a single reaction vessel, using a single reaction mixture (with or without emulsions), with (i) different bead types, each bead type attached with different capture primers, and with (ii) different populations of target nucleic acids, each population having different adaptor sequences joined to the target nucleic acids, where the different adaptor sequences bind selectively to one of the different types of capture primers. Thus, the simplified methods do not require multiple reaction vessels, use reduced amounts of reagents, and do not employ a pooling step.

Many next generation sequencing workflows involve at least one nucleic acid amplification step. The amplification step can introduce amplification biases, which include polyclonality and duplication. These biases are problematic because they distort the original complexity (e.g., relative abundance) of the genetic material to be sequenced.

The disclosed methods, as well as related, systems, compositions, kits and apparatuses, offer advantages over standard emulsion PCR procedures, by reducing both polyclonality and duplication rates of the templated beads.

The disclosed methods also provide increased throughput and reaction efficiency by overcoming Poisson-based limitations based on the requirement to compartmentalize or otherwise isolate single template nucleic acid molecules to achieve clonal amplification. For example, the disclosed methods overcome Poisson-based constraints and allow the amplification of different types of templates onto different types of beads within a single amplification reaction, optionally within a single droplet within an emulsion-based amplification reaction.

The standard emPCR methods require meticulous dilution and adjustment of the relative concentrations of the beads and target nucleic acids so that, ideally each aqueous droplet in the emulsion receives no more than a single target nucleic acid, and a single bead that is attached with capture primers. For example, due to Poisson-based constraints, typically about 20-35% of the templated beads generated by standard emulsion PCR procedures are polyclonal. In a massively parallel sequencing system, the monoclonal and polyclonal templated beads are loaded together on the same sequencing apparatus (e.g., wells, grooves, and flowcells). The polyclonal beads do not yield meaningful sequencing information, because each bead is templated with different target sequences. Thus, the presence of polyclonal beads on the sequencing apparatus reduces the overall percent of useful sequencing reads, and reduces sequencing throughput. In contrast, templated beads prepared according to the present teachings can have reduced polyclonality rates of about 12-30%, which produce improved overall useful sequencing information that leads to an increase in the number of sequencing reads obtained from a single sequencing run, and increased total sequencing throughput. The present teachings provide methods for improving polyclonality rates without dilution and/or adjustment of the relative concentrations of the beads and target nucleic acids, and are conducted a single reaction vessel that contains a single reaction mixture, optionally with an emulsion An increase in the number of sequencing reads can also be achieved by producing enough templated beads to load the greatest number of available sites (e.g., wells, grooves, flowcell, and the like) on the sequencing apparatus. The standard emPCR procedures do not produce enough templated beads, therefore multiple reactions must be prepared, and the templated beads are pooled and loaded onto the sequencing apparatus.

The nucleic acid synthesis methods, according to the present teachings, can be used to prepare emulsions with an increase in the number of aqueous droplets, without a change in reaction volume, to yield an increase in the number of templated beads. This will obviate the need to prepare multiple amplification reactions and bead pooling, and will increase the number of sequencing reads.

When conducting a standard emPCR procedure, changes in reaction volume will also alter the yield of duplicate beads. For example, a decrease in the amplification reaction volume will increase the duplicate bead rate.

The nucleic acid synthesis methods, according to the present teachings, can be conducted in a reduced total reaction volume without significantly increasing the yield of duplicate beads. For example, using the nucleic acid synthesis method (with emulsion), templated beads were prepared in about 2.4 mL reaction volume and yielded about 3.8% duplicate beads, compared to templated beads prepared in about 1.2 mL reaction volume that yielded about 9.4% duplicate beads. In contrast, a control emPCR reaction was conducted in about 1.2 mL and yielded about 26% duplicate beads. The nucleic acid synthesis methods, according to the present teachings, can be conducted in reaction volumes as small as 600 µL or smaller volumes.

A standard emPCR reaction will produce templated beads having about 15-20% duplicate beads. Duplicate beads in a massively parallel sequencing system are undesirable for analyses that compare abundances. For example, a starting pool of RNA may contain different abundances of different transcript species. The relative abundances of the different RNA species will be misrepresented by templated bead preparations that have high duplicate rates.

Templated beads prepared by the nucleic acid synthesis methods, according to the present teachings, have a significantly reduced duplicate bead rate of about 2-12% (using RNA or DNA as starting material), which makes interpretation of the sequencing data more closely aligned with the complexity of the original genetic material.

Another example of amplification bias includes batch effect, which arises from variations in conducting different reactions on the same day or on different days, for example, due to pipetting inaccuracies, reagent batch differences, reaction conditions, and differences in the technicians who are conducting the amplification reactions. Another source of batch effect comes from different primer and/or adaptor sequences that exhibit slight differences in amplification efficiencies. Under standard emPCR conditions, the different amplification efficiencies can be exacerbated when amplified in separate reaction vessels (e.g., separate batches).

The nucleic acid synthesis methods, according to the present teachings, can be used to prepare a mixture of different types of templated beads with reduced batch bias, by conducting the amplification reaction in a single reaction vessel, using a single reaction mixture (with or without emulsions).

The nucleic acid synthesis methods, according to the present teachings, can be used to reduce bead clumping that may occur in a single reaction nucleic acid synthesis method. For example, any of the capture primers, adaptors, reverse primers, fusion primers, and/or conversion primers can cause bead clumping, which may lead to producing polyclonal beads or duplicate beads. Without wishing to be bound by theory, we postulate that bead clumping may be caused by primer dimer interaction between two or more different types of capture primers attached to beads. One approach to solving the bead clumping problem includes selecting the length and/or sequence of any of the primers to reduce bead clumping, where the primers include any one or any combination of the capture primers, adaptors, reverse primers, fusion primers, and/or conversion primers.

The nucleic acid synthesis methods, according to the present teachings, can be used to reduce duplicate bead formation that may occur in a single reaction nucleic acid synthesis method. For example, any of the capture primers, adaptors, reverse primers, fusion primers, and/or conversion primers can cause duplicate bead formation. Without wishing to be bound by theory, we postulate that bead clumping may lead to increased production of duplicate template beads. One approach to solving the duplicate bead formation problem includes selecting the length and/or sequence of any of the primers to duplicate bead formation, where the primers include any one or any combination the capture primers, adaptors, reverse primers, fusion primers, and/or conversion primers. Another approach includes increasing the number of different types of beads in the nucleic acid synthesis method. For example, duplicate bead formation can be reduced by increasing the number of different types beads used to conduct the nucleic acid synthesis method from two types, to three, four, five, six, or more different types of beads. In some embodiments, reduced duplicate bead formation yields improved sequencing metrics, including aligned reads, coverage, polyclonality and mean read length.

In some embodiments, the disclosure relates generally to compositions, as well as related, systems, methods, kits and apparatuses, comprising a plurality of different populations of supports, and a plurality of different populations of target nucleic acids. In some embodiments, the different populations of target nucleic acids can each bind (e.g., bind selectively) to a correspond population of beads. In some embodiments, the compositions (and related methods, systems, kits and apparatuses) also includes any one or any combination of: primers (e.g., capture primer, fusion primer, and/or reverse primers), enzymes (e.g., polymerases), accessory proteins (e.g., recombinase, recombinase loading protein, single-stranded binding protein, helicase or topoisomerase), nucleotides, divalent cations, binding partners and/or co-factors.

In some embodiments, the plurality of different populations of discrete supports, and the plurality of different populations of target nucleic acids, are contained in a single reaction mixture. In some embodiments, the single reaction mixture comprises a single amplification reaction mixture. In some embodiments, the plurality of different populations of discrete supports, and a plurality of different populations of target nucleic acids, can be contained in a single reaction vessel.

In some embodiments, the disclosure relates generally to compositions, as well as related, systems, methods, kits and apparatuses, comprising at least two different populations of discrete supports (e.g., beads and the like) and at least two different populations of target nucleic acids. In some embodiments, the at least two different population of discrete supports are each attached to a particular nucleic acid sequence, e.g., a capture primer sequence. In some embodiments, each different population of supports is attached to a different capture primer sequence. In some embodiments, the discrete supports are each attached to one or more capture primers that provide binding, via hybridization, to their corresponding population of target nucleic acids that can hybridize to the capture primers. In some embodiments, the discrete supports comprise a plurality of particles or beads. In some embodiments, the compositions (and related methods, systems, kits and apparatuses) also includes any one or any combination of: additional primers (e.g., capture primer, fusion primer, and/or reverse primers), enzymes (e.g., polymerases), accessory proteins (recombinase, recombinase loading protein, single-stranded binding protein, helicase or topoisomerase), nucleotides, divalent cations, binding partners and/or co-factors. In some embodiments, at least two different populations of discrete supports are each bound to a different population of target nucleic acids in a single reaction mixture. In some embodiments, the at least two different populations of discrete supports and at least two different populations of target nucleic acids can be contained in a single amplification reaction mixture. In some embodiments, the at least two different populations of discrete supports and at least two different populations of target nucleic acids can be contained in a single reaction vessel. In some embodiments, the compositions (and related methods, systems, kits and apparatuses) comprise more than two different populations of discrete supports and more than two different populations of target nucleic acids.

In some embodiments, the disclosure relates generally to compositions, and related methods, systems, kits and apparatuses, comprising (i) at least a first population of beads, (ii) at least a first population of target nucleic acids, (iii) at least a second population of beads, and (iv) at least a second population of target nucleic acids.

In some embodiments, the compositions (and related methods, systems, kits and apparatuses) comprise a single reaction mixture that includes (i) at least a first population of beads, (ii) at least a first population of target nucleic acids, (iii) at least a second population of beads, and (iv) at least a second population of target nucleic acids.

In some embodiments, the disclosure relates generally to compositions, and related methods, systems, kits and apparatuses, comprising a single reaction mixture that also includes any one or any combination of: additional primers (e.g., capture primer, fusion primer, and/or reverse primers), enzymes (e.g., polymerases), accessory proteins (recombinase, recombinase loading protein, single-stranded binding protein, helicase or topoisomerase), one or more nucleotides, divalent cations, binding partners and/or co-factors.

In some embodiments, the first population of beads can bind the first population of target nucleic acids (FIG. 1). Optionally, the binding between the first population of beads and the first population of target nucleic acids includes nucleic acid hybridization. Optionally the beads of the first population include first capture primers and the binding includes hybridizing the target nucleic acids of the first population to the first capture primers. Optionally, the beads of the first population include first capture primers and no other types of capture primers.

In some embodiments, the first population of beads is bound to the first population of target nucleic acids.

In some embodiments, one or more first type of capture primers are attached to the first population of beads.

In some embodiments, the first population of target nucleic acids contains a plurality of target nucleic acids having the same sequences and/or a plurality of target nucleic acids having different sequences. In some embodiments, the target nucleic acids of the first population include a common sequence ("first common sequence") that is present in some or all members of the first population. In some embodiments, the target nucleic acids of the first population each include one or more common sequences and optionally one or more additional sequences that are not common. In some embodiments, the first common sequence can include a primer binding site ("first primer binding site") that is complementary or identical to a first capture primer.

In some embodiments, the first population of beads is attached to one or more first capture primers that can hybridize to the first population of target nucleic acids or their complements. In some embodiments, the first capture primers can hybridize to the first primer binding site or its complement.

In some embodiments, the second population of beads can bind the second population of target nucleic acids (FIG. 1). Optionally, the binding between the second population of beads and the second population of target nucleic acids includes nucleic acid hybridization. Optionally the beads of the second population include second capture primers and the binding includes hybridizing the target nucleic acids of the second population to the second capture primers. Optionally, the beads of the second population include second capture primers and no other types of capture primers.

In some embodiments, the second population of beads is bound to the second population of target nucleic acids. Optionally, the binding between the second population of beads and the second population of target nucleic acids includes nucleic acid hybridization.

In some embodiments, one or more second type of capture primers are attached to the second population of beads.

In some embodiments, the second population of target nucleic acids contains a plurality of target nucleic acids having the same sequences and/or a plurality of target nucleic acids having different sequences. In some embodiments, the target nucleic acids of the second population include a common sequence ("second common sequence") that is present in some or all members of the second population. In some embodiments, the target nucleic acids of the second population each include one or more common sequences and optionally one or more additional sequences that are not common. In some embodiments, the second common sequence can include a primer binding site ("second primer binding site") that is complementary or identical to a second capture primer.

In some embodiments, the second population of beads is attached to one or more second capture primers that can hybridize to the second population of target nucleic acids or their complements. In some embodiments, the second capture primers can hybridize to the second primer binding site or its complement.

In some embodiments, the at least a first population of beads, the at least a first population of target nucleic acids, the at least a second population of beads, and the at least a second population of target nucleic acids, are contained in a single reaction mixture.

The single reaction mixture can further include a third population of target nucleic acids and a third population of beads. The third population of target nucleic acids can include a third common sequence containing a third primer binding site. The third population of beads can include a third capture primer that is complementary or identical to the third primer binding site.

The single reaction mixture can further include a fourth population of target nucleic acids and a fourth population of beads. The fourth population of target nucleic acids can include a fourth common sequence containing a fourth primer binding site. The fourth population of beads can include a fourth capture primer that is complementary or identical to the fourth primer binding site.

The single reaction mixture can further include a fifth, sixth, seventh, eighth, ninth, tenth or higher order population of target nucleic acids and a fifth, sixth, seventh, eighth, ninth, tenth or higher order population of beads. The fifth, sixth, seventh, eighth, ninth, tenth or higher order population of target nucleic acids can include a fifth, sixth, seventh, eighth, ninth, tenth or higher order common sequence containing a fifth, sixth, seventh, eighth, ninth, tenth or higher order primer binding site. The fifth, sixth, seventh, eighth, ninth, tenth or higher order population of beads can include a fifth, sixth, seventh, eighth, ninth, tenth or higher order capture primer that is complementary or identical to the fifth, sixth, seventh, eighth, ninth, tenth or higher order primer binding site.

In some embodiments, the single reaction mixture comprises a single amplification reaction mixture.

In some embodiments, the at least a first population of beads, the at least a first population of target nucleic acids, the at least a second population of beads, and the at least a second population of target nucleic acids, are contained in a single reaction vessel.

Single reaction mixture also includes any one or any combination of: additional primers (e.g., capture primer, fusion primer, and/or reverse primers), enzymes (e.g., polymerases and/or recombinases), accessory proteins, one or more nucleotides, divalent cations, affinity moieties and/or co-factors.

In some embodiments, the disclosure relates generally to compositions, and related methods, systems, kits and apparatuses, comprising a single reaction mixture that contains (i) a first population of beads, the beads of the first population being attached to one or more first capture primers; (ii) a second population of beads, the beads of the second population being attached to one or more second capture primers, wherein the first and second capture primers are different; (iii) a first population of target nucleic acids, wherein the first population includes at least two different target nucleic acids that can each bind independently to the first capture primers; and (iv) a second population of target nucleic acids, wherein the second population includes at least two different target nucleic acids that can each bind independently to the second capture primers. Optionally, the first population of target nucleic acids includes a primer binding sequence for binding the first capture primers. Optionally, the second population of target nucleic acids includes a primer binding sequence for binding the second capture primers. Optionally, the single reaction mixture includes any one or any combination of: additional primers (e.g., capture primer, fusion primer, and/or reverse primers), enzymes (e.g., polymerases), accessory proteins (recombinase, recombinase loading protein, single-stranded binding protein, helicase or topoisomerase), one or more nucleotides, divalent cations, binding partners and/or co-factors.

In some embodiments, the disclosure relates generally to compositions, and related methods, systems, kits and apparatuses, comprising (i) a first plurality of beads of a first type, (ii) a second plurality of beads of a second type, (iii) a first population of target nucleic acids, and (iv) a second population of target nucleic acids. In some embodiments, the beads of the first type include first capture primers. In some embodiments, the beads of the second type include second capture primers. The first capture primers can be different from the second capture primers. In some embodiments, the first population of target nucleic acids includes a first primer binding sequence that can bind to the first capture primers. The second population of target nucleic acids can include a second primer binding sequence that can bind to the second capture primers. In some embodiments, a composition according to the disclosure is present within a single reaction mixture. In some embodiments, the composition includes a polymerase and/or nucleotides and/or other amplification reagents. In some embodiments, the composition is present within an emulsion microdroplet. In some embodiments, the composition further includes beads of a third type attached to third capture primers. The composition can further include a third population of target nucleic acids including third primer binding sequences, wherein the third primer binding sequence can hybridize to the third capture primers but not to the first and second capture primers.

In some embodiments, the composition further includes beads of a fourth type attached to fourth capture primers. The composition can further include a fourth population of target nucleic acids including fourth primer binding sequences, wherein the fourth primer binding sequence can hybridize to the fourth capture primers but not to the first, second and third capture primers.

In some embodiments, the composition further includes beads of a fifth type attached to fifth capture primers. The composition can further include a fifth population of target nucleic acids including fifth primer binding sequences, wherein the fifth primer binding sequence can hybridize to the fifth capture primers but not to the first, second, third and fourth capture primers.

In some embodiments, the disclosure relates generally to compositions, and related methods, systems, kits and apparatuses, comprising a single reaction mixture which (i) a first plurality of beads of a first type, (ii) a second plurality of beads of a second type, (iii) a first population of target nucleic acids, and (iv) a second population of target nucleic acids.

In some embodiments, the compositions (and related methods, systems, kits and apparatuses) comprise a single reaction mixture which (i) a first plurality of beads of a first type, (ii) a second plurality of beads of a second type, (iii) a first population of target nucleic acids, and (iv) a second population of target nucleic acids, where the single reaction mixtures does not provide compartmentalization or partitioning.

In some embodiments, the compositions (and related methods, systems, kits and apparatuses) comprise a single reaction mixture that contains (i) a first plurality of beads of a first type, the beads of the first type being attached to one or more first capture primers; (ii) a plurality of beads of a second type, the beads of the second type being attached to one or more second capture primers, wherein the first and second capture primers are different; (iii) a first population of target nucleic acids, wherein the first population includes at least two different target nucleic acids that can each bind independently to a first capture primer; and (iv) a second population of target nucleic acids, wherein the second population includes at least two different target nucleic acids that can each bind independently to a second capture primer. In some embodiments, the single reaction mixture does not provide compartmentalization.

In some embodiments, the beads of the first type can be attached to one or more first capture primers.

In some embodiments, the beads of the second type can be attached to one or more second capture primers.

In some embodiments, the first population of target nucleic acids includes at least two different target nucleic acids that can each bind independently to a first capture primer.

Optionally, at least two different target nucleic acids in the first population of target nucleic acids include a primer binding sequence ("first primer binding sequence") that can hybridize to the first capture primer or its complement.

In some embodiments, the second population of target nucleic acids includes at least two different target nucleic acids that can each bind independently to a second capture primer.

Optionally, at least two different target nucleic acids in the second population of target nucleic acids include a primer binding sequence ("second primer binding sequence") that can hybridize to the second capture primer or its complement.

In some embodiments, the single reaction mixture comprises a single continuous liquid phase. Optionally, the single continuous liquid phase comprises an aqueous phase liquid. Optionally, the single continuous liquid phase lacks a hydrophobic phase.

In some embodiments, the single continuous liquid phase does not partition the first type of beads from the second type of beads. In some embodiments, the single continuous liquid phase does not partition the first population of target nucleic acids from the second population of target nucleic acids. In some embodiments, the single continuous liquid phase does not partition any of the types of beads from any of the types of target nucleic acids.

In some embodiments, a single reaction vessel contains the single reaction mixture which includes the first and second plurality of beads of the first and second type, respectively, and the first and second population of target nucleic acids, where the single reaction mixture is not compartmentalized or partitioned.

In some embodiments, the first population of target nucleic acids contains target nucleic acids having the same sequence or a mixture of different sequences.

Optionally, the first population of target nucleic acids contains two or more target nucleic acids that can bind the first plurality of beads.

Optionally, the binding between the first plurality of beads and the first population of target nucleic acids comprise selective binding that includes Watson-Crick base pairing between two nucleic acids.

Optionally, one or more first type of capture primers are attached to the first plurality of beads.

Optionally, the first population of target nucleic acids contains two or more different target nucleic acids that can bind independently to first capture primers.

Optionally, first plurality of beads is attached with one or more of a first type of capture primers having the same sequence or a mixture of different sequences.

Optionally, the first type of capture primers are attached covalently to the first plurality of beads.

Optionally, the first plurality of beads is attached with one type of capture primers having the same sequence.

Optionally, the first plurality of beads do not include any second capture primers.

Optionally, the first type of capture primers include at least one unique identifier sequence.

Optionally, the target nucleic acids in the first population of target nucleic acids are bound to the first plurality of beads.

Optionally, the target nucleic acids of the first population of target nucleic acids are bound to the first plurality of beads by hybridization.

Optionally, at least two different target nucleic acids from the first population of target nucleic acids are each hybridized to a first capture primer.

Optionally, at least one region of a target nucleic acid in the first population of target nucleic acids has a sequence that is complementary or identical to at least a region of a first or second capture primer.

Optionally, at least one region of a target nucleic acid in the first population of target nucleic acids has an identical sequence to at least a region of a first or second capture primer.

In some embodiments, the second population of target nucleic acids contains target nucleic acids having the same sequence or a mixture of different sequences.

Optionally, the second population of target nucleic acids contains two or more target nucleic acids that can bind the second plurality of beads.

Optionally, the binding between the second plurality of beads and the second population of target nucleic acids comprise selective binding.

Optionally, one or more second type of capture primers are attached to the second plurality of beads.

Optionally, the second population of target nucleic acids contains two or more different target nucleic acids that can bind independently to second capture primers.

Optionally, second plurality of beads is attached with one or more of a second type of capture primers having the same sequence or a mixture of different sequences.

Optionally, the second type of capture primers are attached covalently to the second plurality of beads.

Optionally, the second plurality of beads is attached with one type of capture primers having the same sequence.

Optionally, the second plurality of beads do not include any first capture primers.

Optionally, the second type of capture primers include at least one unique identifier sequence.

Optionally, the target nucleic acids in the second population of target nucleic acids are bound to the second plurality of beads.

Optionally, the target nucleic acids of the second population of target nucleic acids are bound to the second plurality of beads by hybridization.

Optionally, at least two different target nucleic acids from the second population of target nucleic acids are each hybridized to a second capture primer.

Optionally, at least one region of a target nucleic acid in the second population of target nucleic acids has a sequence that is complementary or identical to at least a region of a first or second capture primer.

Optionally, at least one region of a target nucleic acid in the second population of target nucleic acids has an identical sequence to at least a region of a first or second capture primer.

Optionally, the target nucleic acids in the first population of target nucleic acids can have the same sequence or a mixture of different sequences.

Optionally, the target nucleic acids in the second population of target nucleic acids can have the same sequence or a mixture of different sequences.

Optionally, at least one target nucleic acid from the first population of target nucleic acids and at least one target nucleic acid from the second population of target nucleic acids have the same sequence.

Optionally, the first population of target nucleic acids and the second population of target nucleic acids do not contain any target nucleic acids with the same sequence.

Optionally, the first plurality of beads is attached with a first type of capture primers, and the second plurality of beads is attached with a second type of capture primers, and the sequences of the first type of capture primers and the second type of capture primers are the same or differ.

Optionally, the first plurality of beads includes only capture primers of the first type.

Optionally, the second plurality of beads includes only capture primers of the second type.

Optionally, the first population of beads binds selectively, via hybridization, to the first population of target nucleic acids.

Optionally, the second population of beads binds selectively, via hybridization, to the second population of target nucleic acids.

Optionally, the selective binding between the first population of beads and the first population of target nucleic acids, and between the second population of beads and the second population of target nucleic acids, occurs in a single reaction mixture.

Optionally, the selective binding between the first population of beads and the first population of target nucleic acids, and between the second population of beads and the second population of target nucleic acids, occurs in a single reaction mixture that provides no compartmentalization.

In some embodiments, the compositions (and related methods, systems, kits and apparatuses) which comprise a single reaction mixture further includes additional primer types, including third, fourth, fifth, or more different primer types.

In some embodiments, the compositions (and related methods, systems, kits and apparatuses) which comprise a single reaction mixture further includes any one or any combination of: additional primers (e.g., capture primer, fusion primer, and/or reverse primers), enzymes (e.g., polymerases), accessory proteins (recombinase, recombinase loading protein, single-stranded binding protein, helicase or topoisomerase), one or more nucleotides, divalent cations, binding partners and/or co-factors.

Optionally, the enzymes catalyze nucleotide incorporation (e.g., polymerase).

Optionally, the enzymes comprise accessory proteins.

Optionally, the additional primers include primers in solution or attached to a support (e.g., a bead or particle).

Optionally, the nucleotides comprise natural nucleotides or analogs thereof.

Optionally, the binding partners comprise biotin.

Optionally, the co-factors include salts, cations, ATP, phosphocreatine, magnesium, manganese, and calcium.

Optionally, the first plurality of beads of a first type, the first population of target nucleic acids, the second plurality of beads of a second type, and the second population of target nucleic acids, are contained in a single reaction mixture.

Optionally, the single reaction mixture comprises an amplification reaction mixture.

Optionally, the first plurality of beads of a first type, the first population of target nucleic acids, the second plurality of beads of a second type, and the second population of target nucleic acids, are contained in a single reaction vessel.

In some embodiments, the disclosure relates generally to compositions, as well as related, systems, methods, kits and apparatuses, comprising at least two different types of beads and at least two different types of target nucleic acids, in a single reaction mixture that provides compartmentalization or partitioning. In some embodiments, the single reaction mixture provides at least one compartment that contains at least two different types of beads and at least two different types of target nucleic acids. For example, the single reaction mixture has at least one compartment that contains (1) a first plurality of beads of a first type and a second plurality of beads of a second type, and (2) a first population of target nucleic acids and a second population of target nucleic acids. Optionally, the at least one compartment can contain additional different types of beads and additional different types of target nucleic acids.

In some embodiments, the disclosure relates generally to compositions, and related methods, systems, kits and apparatuses, comprising a single reaction mixture which (i) a first plurality of beads of a first type, (ii) a second plurality of beads of a second type, (iii) a first population of target nucleic acids, and (iv) a second population of target nucleic acids, where the single reaction mixtures provides compartmentalization or partitioning. In some embodiments, the single reaction mixture provides at least one compartment. Optionally, the at least one compartment can contain additional different types of beads and additional different types of target nucleic acids.

In some embodiments, the disclosure relates generally to the compositions, and related methods, systems, kits and apparatuses, comprising a single reaction mixture that provides at least one compartment, where the at least one compartment contains (i) a first plurality of beads of a first type, the beads of the first type being attached to one or more first capture primers; (ii) a plurality of beads of a second type, the beads of the second type being attached to one or more second capture primers, wherein the first and second capture primers are different; (iii) a first population of target nucleic acids, wherein the first population includes at least two different target nucleic acids that can each bind independently to a first capture primer; and (iv) a second population of target nucleic acids, wherein the second population includes at least two different target nucleic acids that can each bind independently to a second capture primer.

Optionally, the single reaction mixture is contained in a single reaction vessel.

In some embodiments, the beads of the first type can be attached to one or more first capture primers.

In some embodiments, the beads of the second type can be attached to one or more second capture primers.

In some embodiments, the first population of target nucleic acids includes at least two different target nucleic acids that can each bind independently to a first capture primer.

Optionally, at least two different target nucleic acids in the first population of target nucleic acids include a primer binding sequence for binding the first capture primer.

In some embodiments, the second population of target nucleic acids includes at least two different target nucleic acids that can each bind independently to a second capture primer.

Optionally, at least two different target nucleic acids in the second population of target nucleic acids include a primer binding sequence for binding the second capture primer.

Optionally, the single reaction mixture further includes any one or any combination of: additional primers (e.g., capture primer, fusion primer, and/or reverse primers), enzymes (e.g., polymerases), accessory proteins (recombinase, recombinase loading protein, single-stranded binding protein, helicase or topoisomerase), one or more nucleotides, divalent cations, binding partners and/or co-factors.

In some embodiments, the disclosure relates generally to compositions, as well as related, systems, methods, kits and apparatuses, comprising a single reaction mixture that provides compartmentalization or partitioning includes an emulsion.

Optionally, the emulsion comprises a discontinuous hydrophilic phase and a continuous hydrophobic phase.

Optionally, the discontinuous hydrophilic phase is surrounded by the continuous hydrophobic phase.

Optionally, the emulsion comprises at least one hydrophilic phase compartment (e.g., droplet or micro-reactor) surrounded by a continuous hydrophobic phase.

Optionally, the discontinuous hydrophilic phase provides a compartment.

Optionally, the emulsion comprises a plurality of hydrophilic phase droplets and a continuous hydrophobic phase.

Optionally, the emulsion comprises a plurality of aqueous droplets and a continuous hydrophobic phase.

Optionally, the emulsion comprises at least one aqueous droplet.

Optionally, the at least one aqueous droplet includes one or more beads.

Optionally, the at least one aqueous droplet includes one or more different target nucleic acids.

Optionally, the emulsion includes at least one aqueous droplet that includes one or more beads of the first type, the second type, or beads of both the first and second type.

Optionally, the emulsion includes at least one aqueous droplet that includes one or more different target nucleic acids, including the first population, the second population, or both the first and second populations of target nucleic acids.

In some embodiments, the emulsion comprises two immiscible liquid phases. In some embodiments, two immiscible liquid phases are mixed together to make the emulsion. In some embodiments, one of the liquid phases is dispersed in the other. Optionally, the emulsion comprises a mixture of an aqueous liquid and a water-immiscible organic liquid. Optionally, the emulsion comprises at least one anionic, cationic or non-ionic surfactant. Optionally, the emulsion can have a droplet-type dispersion comprising oil-in-water, water-in-oil, or a bicontinuous microemulsion.

In some embodiments, the water immiscible organic liquid comprises an oil. In some embodiments, the oil can be from a natural source, including animal (e.g., tallow or lard), fish (e.g., fish oil), shark, seeds, nuts or plants (e.g., vegetable oils). Optionally, the oil can be from derived from petroleum, including mineral oils. Optionally, the oil comprises a fluorochemical oil, polyalphaolefin or ester oil.

In some embodiments, the surfactant includes small molecule surfactants, polymeric surfactants, triblock co-polymer surfactants or non-ionic block copolymer surfactants. Optionally, the surfactant comprises a sorbitan oleate or a silicone surfactant.

Optionally, the hydrophilic phase compartment can contain at least two different types of beads. Optionally, the hydrophilic phase compartment can contain at least two different types of target nucleic acids.

Optionally, at least one hydrophilic phase compartment can contain (i) a first plurality of beads of a first type, (ii) a first population of target nucleic acids, (iii) a second plurality of beads of a second type, and (iv) a second population of target nucleic acids. Optionally, the at least one hydrophilic phase compartment can contain additional different types of beads and additional different types of target nucleic acids. Optionally, the hydrophilic phase compartment can further contain any one or any combination of: primers (e.g., capture primer, fusion primer, and/or reverse primers), enzymes (e.g., polymerases), accessory proteins (recombinase, recombinase loading protein, single-stranded binding protein, helicase or topoisomerase), one or more nucleotides, divalent cations, binding partners and/or co-factors.

Optionally, the at least one compartment (e.g., hydrophilic phase compartment) contains the first population of target nucleic acids which include target nucleic acids having the same sequence or a mixture of different sequences.

Optionally, the first population of target nucleic acids contains two or more target nucleic acids that can bind the first plurality of beads.

Optionally, the binding between the first plurality of beads and the first population of target nucleic acids comprise selective binding.

Optionally, the first plurality of beads are attached to one or more first type of capture primers.

Optionally, the first population of target nucleic acids contains two or more different target nucleic acids that can bind independently to first capture primers.

Optionally, first plurality of beads is attached with one or more of a first type of capture primers having the same sequence or a mixture of different sequences.

Optionally, the first type of capture primers are attached covalently to the first plurality of beads.

Optionally, the first plurality of beads is attached with one type of capture primers having the same sequence.

Optionally, the first plurality of beads do not include any second capture primers.

Optionally, the first type of capture primers include at least one unique identifier sequence.

Optionally, the target nucleic acids in the first population of target nucleic acids are bound to the first plurality of beads.

Optionally, the target nucleic acids of the first population of target nucleic acids are bound to the first plurality of beads by hybridization.

Optionally, at least two different target nucleic acids from the first population of target nucleic acids are each hybridized to a first capture primer.

Optionally, at least one region of a target nucleic acid in the first population of target nucleic acids is complementary to at least a region of a first or second capture primer.

Optionally, at least one region of a target nucleic acid in the first population of target nucleic acids has an identical sequence to at least a region of a first or second capture primer.

Optionally, the at least one compartment (e.g., hydrophilic phase compartment) contains the second population of target nucleic acids which include target nucleic acids having the same sequence or a mixture of different sequences.

Optionally, the second population of target nucleic acids contains two or more target nucleic acids that can bind the second plurality of beads.

Optionally, the binding between the second plurality of beads and the second population of target nucleic acids comprise selective binding.

In some embodiments, one or more second type of capture primers are attached to the second plurality of beads.

Optionally, the second population of target nucleic acids contains two or more different target nucleic acids that can bind independently to second capture primers.

Optionally, second plurality of beads is attached with one or more of a second type of capture primers having the same sequence or a mixture of different sequences.

Optionally, the second type of capture primers are attached covalently to the second plurality of beads.

Optionally, the second plurality of beads is attached with one type of capture primers having the same sequence.

Optionally, the second plurality of beads do not include any first capture primers.

Optionally, the second type of capture primers include at least one unique identifier sequence.

Optionally, the target nucleic acids in the second population of target nucleic acids are bound to the second plurality of beads.

Optionally, the target nucleic acids of the second population of target nucleic acids are bound to the second plurality of beads by hybridization.

Optionally, at least two different target nucleic acids from the second population of target nucleic acids are each hybridized to a second capture primer.

Optionally, at least one region of a target nucleic acid in the second population of target nucleic acids is complementary to at least a region of a first or second capture primer.

Optionally, at least one region of a target nucleic acid in the second population of target nucleic acids has an identical sequence to at least a region of a first or second capture primer.

Optionally, the at least one compartment (e.g., hydrophilic phase compartment) contains at least one target nucleic acid from the first population of target nucleic acids and at least one target nucleic acid from the second population of target nucleic with the same sequence.

Optionally, the at least one compartment (e.g., hydrophilic phase compartment) contains the first population of target nucleic acids and the second population of target nucleic acids which do not include any target nucleic acids with the same sequence.

Optionally, the first plurality of beads is attached with a first type of capture primers, and the second plurality of beads is attached with a second type of capture primers, and the sequences of the first type of capture primers and the second type of capture primers are the same or different.

Optionally, the first plurality of beads includes only capture primers of the first type.

Optionally, the second plurality of beads includes only capture primers of the second type.

Optionally, the first population of beads binds selectively, via hybridization, to the first population of target nucleic acids.

Optionally, the second population of beads binds selectively, via hybridization, to the second population of target nucleic acids.

Optionally, the selective binding occurs in the at least one compartment (e.g., hydrophilic phase compartment).

Optionally, the at least one compartment (e.g., hydrophilic phase compartment) contains additional primers, including third, fourth, fifth, or more different primer types.

In some embodiments, the disclosure relates generally to compositions, and related methods, systems, kits and apparatuses, comprising a single reaction mixture having at least one compartment (e.g., hydrophilic phase compartment) which contains (i) a first plurality of beads of a first type, (ii) a first population of target nucleic acids, (iii) a second plurality of beads of a second type, (iv) a second population of target nucleic acids, and (v) any one or any combination of: additional primers (e.g., capture primer, fusion primer, and/or reverse primers), enzymes (e.g., polymerases), accessory proteins (recombinase, recombinase loading protein, single-stranded binding protein, helicase or topoisomerase), one or more nucleotides, divalent cations, binding partners and/or co-factors.

Optionally, the enzymes catalyze nucleotide incorporation (e.g., polymerase).

Optionally, the enzymes comprise accessory proteins (e.g., recombinase, recombinase loading protein, single-stranded binding protein, helicase or topoisomerase).

Optionally, the additional primers include primers in solution or attached to at least one discrete support. Optionally, the additional primers include primers that are not covalently attached to the first or second, or to any type of beads.

Optionally, the nucleotides comprise natural nucleotides or analogs thereof.

Optionally, the binding partners comprise biotin.

Optionally, the co-factors include salts, cations, ATP, phosphocreatine, magnesium, manganese, and calcium.

Optionally, the single reaction mixture comprises an amplification reaction mixture.

Optionally, the first plurality of beads of a first type, the first population of target nucleic acids, the second plurality of beads of a second type, and the second population of target nucleic acids, are contained in a single reaction vessel.

In some embodiments, the disclosure relates generally to compositions, as well as related, systems, methods, kits and apparatuses, comprising a reaction mixture containing a plurality of different template nucleic acids with a plurality of discrete supports (e.g., beads), and a plurality of target nucleic acid molecules (also referred to herein simply as "target nucleic acids"), wherein the beads and the target nucleic acids are present in a specific amounts resulting in a defined ratio of beads-to-target nucleic acids. In some embodiments, the ratio of beads-to-target nucleic acids is the number of beads present in a defined volume of reaction mixture, divided by the number of target nucleic acids within the defined volume of the reaction mixture. In some embodiments, the beads and the target nucleic acids are added to given amounts of oil and/or aqueous phases to form a reaction mixture containing beads, target nucleic acids and oil phases and/or aqueous phases; optionally the ratio is the number of beads added, divided by the number of target nucleic acids added, to form a defined volume of the reaction mixture. In some embodiments, the reaction mixture includes a particular, predefined or preselected ratio of beads-to-target nucleic acids in a defined volume of the reaction mixture. Optionally, the reaction mixture contains a ratio of beads-to-target nucleic acids in a volume of reaction mixture that either includes or lacks compartmentalization. Optionally, the reaction mixture is a single reaction mixture. In some embodiments, the reaction mixture contains a ratio of beads-to-target nucleic acids in a volume that includes from about an average of 1 discrete support and an average of 1 target nucleic acid per 1 mL reaction mixture to an average of about 2 discrete supports: an average of 1 target nucleic acid per 1 mL reaction mixture, or about an average of 2 discrete support and an average of 1 target nucleic acid per 1 mL reaction mixture to an average of about 5 discrete supports: an average of 1 target nucleic acid per 1 mL reaction mixture. In some embodiments, the reaction mixture includes an average beads-to-target nucleic acid ratio, which can be the average number of beads divided by the average number of nucleic acids present in a defined volume of the reaction mixture. For example, the reaction mixture optionally includes a ratio of an average of 5 discrete supports to an average of 1 target nucleic acid per 1 mL reaction mixture ("5:1 average beads-to-target nucleic acid ratio"), or a ratio of an average of 7 discrete supports to an average of 1 target nucleic acid per 1 mL ("7:1 average beads-to-target nucleic acid ratio"), or a ratio of an average of 10 discrete supports to an average of 1 target nucleic acid per 1 mL of reaction mixture ("10:1 average beads-to-target nucleic acid ratio"). In some embodiments, the reaction mixture includes an average bead-to-target nucleic acid ratio of about 1, about 5, or about 7, or about 10, or about 15, or about 25. In some embodiments, the reaction mixture includes an average bead-to-target nucleic acid ratio of from about 1 to about 10, or from 1 to 10, from 1 to 15, or from 1 to 25, or from about 1 to about 5, or from 1 to 5, or from 5 to 25, or from 5 to 15, or from 5 to 10, or from 5 to 7, or from 7 to 15, or from 7 to 10, or from 7 to 25, or from 15 to 25. In some embodiments, the reaction mixture includes a ratio of about 10 discrete supports:1 target nucleic acid per 1 mL of reaction mixture to about 15 discrete supports:1 nucleic acid per 1 mL, or a ratio of about 15 discrete supports:1 nucleic acid per 1 mL to about 20 discrete supports:1 nucleic acid per 1 mL, or a ratio of about 20 discrete supports:1 nucleic acid per 1 mL to about 25 discrete supports:1 target nucleic acid per 1 mL, or a ratio of about 25 discrete supports:1 target nucleic acid per 1 mL to about 30 discrete supports:1 nucleic acid per 1 mL, or a ratio of about 30 discrete supports:1 target nucleic acid per 1 mL to about 50 discrete supports:1 target nucleic acid per 1 mL of reaction mixture.

Optionally, the reaction mixture contains a ratio of beads-to-target nucleic acids in a volume of the reaction mixture that includes about 0.5 billion discrete supports and about 50 million target nucleic acids per 1 mL volume of reaction mixture.

Optionally, the reaction mixture contains a ratio of beads-to-target nucleic acids in a volume of reaction mixture that includes about 1 billion discrete supports and about 100 million target nucleic acids per 1 mL of reaction mixture.

Optionally, the ratio of the discrete supports to the target nucleic acids can be increased or decreased per 1 mL reaction mixture.

Optionally, the amount of discrete supports can be increased about 2- to 10-fold per 1 mL reaction mixture (e.g., increased to about 1-5 billion discrete supports per 1 mL reaction mixture).

Optionally, the amount of discrete supports can be increased about 2- to 10-fold per 1 mL reaction mixture (e.g., increased to about 2-10 billion discrete supports per 1 mL reaction mixture), or increased about 10- to 20-fold per 1 mL reaction mixture (e.g., increased to about 10-20 billion discrete supports per 1 mL reaction mixture), or increased about 20- to 30-fold per 1 mL reaction mixture (e.g., increased to about 20-30 billion discrete supports per 1 mL reaction mixture), or increased about 30- to 40-fold per 1 mL reaction mixture (e.g., increased to about 30-40 billion discrete supports per 1 mL reaction mixture), or increased about 40- to 50-fold or more per 1 mL reaction mixture (e.g., increase to about 40-50 billion discrete supports or more per 1 mL reaction mixture).

Optionally, the amount of discrete supports can be decreased about 2- to 10-fold per 1 mL reaction mixture, or decreased about 10- to 25-fold per 1 mL reaction mixture, or decreased about 25- to 50-fold per 1 mL reaction mixture.

Optionally, the amount of target nucleic acids can be increased about 2- to about 5-fold per 1 mL reaction mixture (e.g., increased to about 100-250 million target nucleic acids per 1 mL reaction mixture).

Optionally, the amount of target nucleic acids can be increased about 2- to about 5-fold per 1 mL reaction mixture (e.g., increased to about 200-500 million target nucleic acids per 1 mL reaction mixture), or increased about 5- to about 10-fold per 1 mL reaction mixture (e.g., increased to about 500-1000 million target nucleic acids per 1 mL reaction mixture), or increased about 10- to about 20-fold per 1 mL reaction mixture (e.g., increased to about 1000-2000 million target nucleic acids per 1 mL reaction mixture), or increased about 20- to about 50-fold per 1 mL reaction mixture (e.g., increased to about 2000-5000 million target nucleic acids per 1 mL reaction mixture).

Optionally, the amount of target nucleic acids can be increased up to 100-fold or more per 1 mL reaction mixture (e.g., increased to about 10,000 million target nucleic acids or more per 1 mL reaction mixture).

Optionally, the amount of target nucleic acids can be decreased about 2- to 10-fold per 1 mL reaction mixture, or decreased about 10- to 25-fold per 1 mL reaction mixture, or decreased about 25- to 50-fold per 1 mL reaction mixture.

In some embodiments, the compositions, as well as related, systems, methods, kits and apparatuses, comprising a single reaction mixture containing about 6 billion discrete supports and about 300-800 million target nucleic acids in about 2.4 mL reaction mixture.

In some embodiments, the compositions, as well as related, systems, methods, kits and apparatuses, comprise a single reaction mixture containing between about 18-24 billion discrete supports and about 1800 million target nucleic acids in a defined volume. Optionally, the defined volume of the reaction mixture is between 1 mL and 5 mL, typically between 2 and 4 mL, more typically between 2 and 3 mL. In some embodiments, the defined volume is 2.4 mL. Optionally, the reaction mixture includes or lacks compartmentalization.

In some embodiments, the disclosure relates generally to methods, as well as related, systems, compositions, kits and apparatuses, for synthesizing nucleic acids by (a) providing a plurality of different populations of target nucleic acids, and a plurality of different types of discrete supports, and (b) forming different amplified populations of the target nucleic acids that are attached to the different types of discrete supports. In some embodiments, the methods for synthesizing nucleic acids can be used to amplify nucleic acids.

In some embodiments, the disclosure relates generally to methods, as well as related, systems, compositions, kits and apparatuses, for amplifying different target nucleic acids by one or more rounds of nucleic acid synthesis.

In some embodiments, the plurality of different populations of target nucleic acids, can bind the plurality of different types of discrete supports. In some embodiments, the different types of discrete supports include different types of capture primers. In some embodiments, the plurality of different populations of target nucleic acids binds the different types of capture primers. In some embodiments, the plurality of different populations of target nucleic acids, and the plurality of different types of discrete supports, are provided in a single reaction mixture. In some embodiment, the single reaction mixture comprises a nucleic acid amplification reaction mixture. In some embodiments, the single reaction mixture includes any one or any combination of: primers (e.g., capture primer, fusion primer, and/or reverse primers), enzymes (e.g., polymerases), accessory proteins (recombinase, recombinase loading protein, single-stranded binding protein, helicase or topoisomerase), one or more nucleotides, divalent cations, binding partners and/or co-factors. Optionally, the single reaction mixture provides compartmentalization, or does not provide compartmentalization. Optionally, the single reaction mixture comprises an emulsion. Optionally, the single reaction mixture can be contained in a single reaction vessel. In some embodiments, the plurality of different discrete supports includes a plurality of different beads. In some embodiments, the plurality of different types of discrete supports includes two, three, four, five, six, seven, eight, nine, ten, eleven, or more different types of discrete supports. In some embodiments, the different amplified populations of the target nucleic acids are formed by conducting any type of nucleic acid amplification reaction, including PCR, isothermal, rolling circle, or emulsion-based amplification. In some embodiments, the different amplified populations of the target nucleic acids are substantially monoclonal. Optionally, the method further comprises sequencing the different amplified populations of the target nucleic acids that are attached to the different types of discrete supports.

In some embodiments, the disclosure relates generally to methods, as well as related, systems, compositions, kits and apparatuses, for synthesizing nucleic acids by (a) providing at least two different populations of target nucleic acids and at least two different populations of discrete supports and (b) forming at least two different amplified populations of the target nucleic acids that are attached to the different types of discrete supports.

In some embodiments, the plurality of different populations of target nucleic acids, can bind the plurality of different types of discrete supports. In some embodiments, the at least two different populations of discrete supports include different types of capture primers. In some embodiments, the at least two different populations of target nucleic acids selectively binds the different types of capture primers. In some embodiments, the plurality of different populations of target nucleic acids, and the plurality of different types of discrete supports, are provided in a single reaction mixture. In some embodiment, the single reaction mixture comprises a nucleic acid amplification reaction mixture. In some embodiments, the single reaction mixture includes any one or any combination of: primers (e.g., capture primer, fusion primer, and/or reverse primers), enzymes (e.g., polymerases), accessory proteins (recombinase, recombinase loading protein, single-stranded binding protein, helicase or topoisomerase), one or more nucleotides, divalent cations, binding partners and/or co-factors. Optionally, the single reaction mixture provides compartmentalization, or does not provide compartmentalization. Optionally, the single reaction mixture comprises an emulsion. Optionally, the single reaction mixture can be contained in a single reaction vessel. In some embodiments, the at least two different populations of discrete supports includes at least two different populations of beads. In some embodiments, the at least two different populations of discrete supports includes two, three, four, five, six, seven, eight, nine, ten, eleven, or more different types of discrete supports. In some embodiments, the at least two different amplified populations of the target nucleic acids are formed by conducting any type of nucleic acid amplification reaction, including PCR, isothermal, rolling circle, or emulsion-based amplification. In some embodiments, the at least two different amplified populations of the target nucleic acids are substantially monoclonal. Optionally, the method further comprises sequencing the at least two different amplified populations of the target nucleic acids that are attached to the different types of discrete supports.

In some embodiments, the disclosure relates generally to methods, as well as related, systems, compositions, kits and apparatuses, for synthesizing nucleic acids by (a) providing a single reaction mixture containing (i) at least a first population of beads, (ii) at least a first population of target nucleic acids, (iii) at least a second population of beads, and (iv) at least a second population of target nucleic acids; and (b) forming a first and a second amplified population of the first and second populations of target nucleic acids that are attached to the first and second population of beads, respectively.

In some embodiments, the at least a first population of target nucleic acids can bind the at least a first population of beads. In some embodiments, the at least a second population of target nucleic acids can bind the at least a second population of beads. In some embodiments, the at least first population of beads includes a first type of capture primers. In some embodiments, the at least second population of beads includes a second type of capture primers. In some embodiments, the at least first population of target nucleic acids selectively binds the first type of capture primers. In some embodiments, the at least second population of target nucleic acids selectively binds the second type of capture primers. In some embodiment, the single reaction mixture comprises a nucleic acid amplification reaction mixture. In some embodiments, the single reaction mixture includes any one or any combination of: primers (e.g., capture primer, fusion primer, and/or reverse primers), enzymes (e.g., polymerases), accessory proteins (recombinase, recombinase loading protein, single-stranded binding protein, helicase or topoisomerase), one or more nucleotides, divalent cations, binding partners and/or co-factors. Optionally, the single reaction mixture provides compartmentalization, or does not provide compartmentalization. Optionally, the single reaction mixture comprises an emulsion. Optionally, the single reaction mixture can be contained in a single reaction vessel. In some embodiments, the single reaction mixture contains two, three, four, five, six, seven, eight, nine, ten, eleven, or more different populations of beads. In some embodiments, the first and the second amplified populations of the first and second populations of target nucleic acids are formed by conducting any type of nucleic acid amplification reaction, including PCR, isothermal, rolling circle, or emulsion-based amplification. In some embodiments, the first amplified population of the first population of target nucleic acids is substantially monoclonal. In some embodiments, the second amplified population of the second population of target nucleic acids is substantially monoclonal. Optionally, the method further comprises sequencing the first and the second amplified populations of target nucleic acids.

In some embodiments, the disclosure relates generally to methods, as well as related, systems, compositions, kits and apparatuses, for synthesizing nucleic acids by (a) providing a single reaction mixture containing (i) a plurality of beads of a first type, (ii) a plurality of beads of a second type, (iii) a first population of target nucleic acids, and (iv) a second population of target nucleic acids; (b) forming a first amplified population of nucleic acids by amplifying one or more target nucleic acids of the first population; and (c) forming a second amplified population of nucleic acids by amplifying one or more target sequences from the second population of target nucleic acids.

In some embodiments, the disclosure relates generally to methods, as well as related, systems, compositions, kits and apparatuses, for synthesizing nucleic acids by (a) providing (i) a single reaction mixture containing a plurality of beads of a first type, the beads of the first type including first capture primers, (ii) a plurality of beads of a second type, the beads of the second type including second capture primers, wherein the first and second capture primers are different, (iii) a first population of target nucleic acids, wherein the first population includes at least one target nucleic acid of a first type that binds to the first capture primers, and (iv) a second population of target nucleic acids, wherein the second population includes at least one target nucleic acid of a second type that binds to the second capture primers; (b) forming a first amplified population of nucleic acids by amplifying one or more target nucleic acids of the first population, wherein the first amplified population is attached to one or more beads of the first type; and (c) forming a second amplified population of nucleic acids by amplifying one or more target sequences from the second population of target nucleic acids, wherein the second amplified population is attached to one or more beads of the second type.

In some embodiments, the disclosure relates generally to methods, as well as related, systems, compositions, kits and apparatuses, for monoclonally amplifying a first target sequence from a first population of target nucleic acids and a first target sequence from a second population of target nucleic acids comprising: (a) providing a single reaction mixture having (i) a plurality of a first type of beads including first capture primers, (ii) a plurality of a second type of beads including second capture primers, (iii) a first population of target nucleic acids, (iv) a first fusion primer that includes a portion that is complementary to the first capture primers, (v) a second population of target nucleic acids, and (vi) a second fusion primer that includes a portion that is complementary to the second capture primers; (b) forming a substantially monoclonal population of the first target sequence from the first population of target nucleic acids on the first type of beads using the first fusion primer; and (c) forming a substantially monoclonal population of the first target sequence from the second population of target nucleic acids on the second type of beads using the second fusion primer. Optionally, the first and second capture primers are different. Optionally, the first population includes at least one target nucleic acid that binds to the first fusion primer. Optionally, the second population includes at least one target nucleic acid that binds to the second fusion primer.

In some embodiments, the disclosure relates generally to methods, as well as related, systems, compositions, kits and apparatuses, for amplifying a plurality of different nucleic acid populations in a single reaction mixture, comprising: (a) providing a single reaction mixture including (i) a first and a second population of nucleic acids, wherein the first population of nucleic acids contain a first primer binding sequence, and wherein the second population of nucleic acids contain a second primer binding sequence, and (ii) a first plurality of beads including a first capture sequence that can bind to the first primer binding sequence, (iii) a second plurality of beads including a second capture sequence that can bind to the second primer binding sequence; and (b) amplifying, within the single reaction mixture, one or more nucleic acids from the first population to form a first amplified population, and one or more nucleic acids from the second population to form a second amplified population.

In some embodiments, the sequences of the first and the second primer binding sequences differ from each other.

In some embodiments, the sequences of the first and second capture sequences are different from each other.

In some embodiments, the first amplified population can be bound to one or more beads of the first type.

In some embodiments, the second amplified population can be bound to one or more beads of the second type.

In some embodiments, the disclosure relates generally to methods, as well as related, systems, compositions, kits and apparatuses, for synthesizing nucleic acids In some embodiments, the plurality of beads of the first type includes one or more first type of capture primers.

In some embodiments, the plurality of beads of the second type includes one or more second type of capture primers.

In some embodiments, the sequences of the one or more first capture primers on the first type of beads are the same or a mixture of different sequences.

In some embodiments, the sequences of the one or more second capture primers on the second type of beads are the same or a mixture of different sequences.

In some embodiments, the sequences of the first capture primers are the same as the sequences of the second capture primers.

In some embodiments, the sequences of the first capture primers are different from the sequences of the second capture primers.

Optionally, the concentration (e.g., density) of the first and the second capture primers is about the same.

In some embodiments, the first population of target nucleic acids can bind the plurality of beads of the first type.

In some embodiments, the first population of target nucleic acids includes at least one target nucleic acid of a first type that binds to the first capture primers.

Optionally, the first population of target nucleic acids includes at least one target nucleic acid of the first type having a sequence that is complementary or identical to the sequence of the first capture primers.

In some embodiments, the first population of target nucleic acids selectively binds the first type of capture primers.

Optionally, the first population of target nucleic acids includes at least one target nucleic acid of the first type that binds the first type of beads by hybridizing to the first capture primers.

In some embodiments, the second population of target nucleic acids can bind the plurality of beads of the second type.

In some embodiments, the second population of target nucleic acids includes at least one target nucleic acid of a second type that binds to the second capture primers.

Optionally, the second population of target nucleic acids includes at least one target nucleic acid of the second type having a sequence that is complementary or identical to the sequence of the second capture primers.

Optionally, the second population of target nucleic acids binds the second capture primers selectively.

Optionally, the second population of target nucleic acids includes at least one target nucleic acid of the second type that binds the second type of beads by hybridizing to the second capture primers.

In some embodiment, the single reaction mixture comprises a nucleic acid amplification reaction mixture.

In some embodiments, the single reaction mixture includes any one or any combination of: primers (e.g., capture primer, fusion primer, and/or reverse primers), enzymes (e.g., polymerases), accessory proteins (recombinase, recombinase loading protein, single-stranded binding protein, helicase or topoisomerase), one or more nucleotides, divalent cations, binding partners and/or co-factors.

Optionally, the single reaction mixture provides compartmentalization, or does not provide compartmentalization.

Optionally, the single reaction mixture comprises an emulsion. Optionally, the emulsion comprises a water-in-oil emulsion.

Optionally, the single reaction mixture can be contained in a single reaction vessel.

In some embodiments, the single reaction mixture contains two, three, four, five, six, seven, eight, nine, ten, eleven, or more different types of beads, where each different type of beads includes a different type of capture primer.

In some embodiments, the first amplified population of nucleic acids is formed by amplifying one or more target nucleic acids of the first population.

In some embodiments, the forming the first amplified population of nucleic acids includes hybridizing at least one target nucleic acid from the first population of target nucleic acids to the first capture primer on the first type of beads.

Optionally, the forming the first amplified population of nucleic acids further includes extending the first capture primer in a template-dependent primer extension reaction.

In some embodiments, the first amplified population of nucleic acids is covalently attached to one or more beads of the first type.

In some embodiments, the first amplified population of nucleic acids is formed by conducting any type of nucleic acid amplification reaction, including PCR, isothermal, rolling circle, or emulsion-based amplification.

In some embodiments, the first amplified population of nucleic acids is substantially monoclonal.

In some embodiments, the second amplified population of nucleic acids is formed by amplifying one or more target nucleic acids of the second population.

In some embodiments, the forming the second amplified population of nucleic acids includes hybridizing at least one target nucleic acid from the second population of target nucleic acids to the second capture primer on the second type of beads.

Optionally, the forming the second amplified population of nucleic acids further includes extending the second capture primer in a template-dependent primer extension reaction.

In some embodiments, the second amplified population of nucleic acids is covalently attached to one or more beads of the second type.

In some embodiments, the second amplified population of nucleic acids is formed by conducting any type of nucleic acid amplification reaction, including PCR, isothermal, rolling circle, or emulsion-based amplification.

In some embodiments, the second amplified population of nucleic acids is substantially monoclonal.

In some embodiments, the first and the second amplified populations of nucleic acids are both substantially monoclonal.

Optionally, the method further comprises sequencing the first amplified population of nucleic acids. Optionally, the method further comprises sequencing the second amplified population of nucleic acids. Optionally, the first and the second amplified populations of nucleic acids are sequenced in parallel. Optionally, the sequencing includes detecting one or more nucleotide incorporation byproducts. Optionally, the sequencing includes detecting hydrogen ions or pyrophosphate.

In some embodiments, the disclosure relates generally to methods, as well as related, systems, compositions, kits and apparatuses, for synthesizing nucleic acids by (a) providing a single reaction mixture containing (i) a plurality of beads of a first type, (ii) a plurality of beads of a second type, (iii) a first population of target nucleic acids, and (iv) a second population of target nucleic acids; (b) forming a first amplified population of nucleic acids by amplifying one or more target nucleic acids of the first population; and (c) forming a second amplified population of nucleic acids by amplifying one or more target sequences from the second population of target nucleic acids, where the single reaction mixture does not provide compartmentalization or partitioning.

In some embodiments, the disclosure relates generally to methods, as well as related, systems, compositions, kits and apparatuses, for synthesizing nucleic acids by (a) providing a single reaction mixture containing (i) a plurality of beads of a first type, (ii) a plurality of beads of a second type, (iii) a first population of target nucleic acids, and (iv) a second population of target nucleic acids; (b) forming a first amplified population of nucleic acids by amplifying one or more target nucleic acids of the first population; and (c) forming a second amplified population of nucleic acids by amplifying one or more target sequences from the second population of target nucleic acids, where the single reaction mixture does not provide compartmentalization or partitioning, and optionally, where the single reaction mixture also includes one or more accessory proteins including recombinase, recombinase loading protein, single-stranded binding protein, helicase or topoisomerase.

In some embodiments, the disclosure relates generally to methods, as well as related, systems, compositions, kits and apparatuses, for synthesizing nucleic acids by (a) providing a single reaction mixture containing (i) a plurality of beads of a first type, the beads of the first type being attached to one or more first capture primers, (ii) a plurality of beads of a second type, the beads of the second type being attached to one or more second capture primers, wherein the first and second capture primers are different, (iii) a first population of target nucleic acids, wherein the first population includes at least two different target nucleic acids that can each bind independently to a first capture primer, and (iv) a second population of target nucleic acids, wherein the second population includes at least two different target nucleic acids that can each bind independently to a second capture primer; (b) forming a first amplified population of nucleic acids by amplifying one or more target nucleic acids of the first population; and (c) forming a second amplified population of nucleic acids by amplifying one or more target sequences from the second population of target nucleic acids, where the single reaction mixture does not provide compartmentalization or partitioning, and optionally, where the single reaction mixture also includes one or more accessory proteins including recombinase, recombinase loading protein, single-stranded binding protein, helicase or topoisomerase.

In some embodiments, in the methods for synthesizing nucleic acids, the single reaction mixture comprises a single continuous liquid phase. In some embodiments, the single continuous liquid phase comprises an aqueous phase liquid. In some embodiments, the single continuous liquid phase lacks a hydrophobic phase.

In some embodiments, the single continuous liquid phase does not partition the first type of beads from the second type of beads. In some embodiments, the single continuous liquid phase does not partition the first population of target nucleic acids from the second population of target nucleic acids. In some embodiments, the single continuous liquid phase does not partition any of the types of beads from any of the types of target nucleic acids.

In some embodiments, a single reaction vessel contains a single reaction mixture which includes at least two different types of beads and at least two different types of target nucleic acids, where the single reaction mixture does not provide compartmentalization or partitioning.

In some embodiments, the single reaction mixture does not provide compartmentalization, and the first population of target nucleic acids contains target nucleic acids having the same sequence or a mixture of different sequences.

Optionally, the first population of target nucleic acids contains two or more target nucleic acids that can bind the first plurality of beads.

Optionally, the binding between the first plurality of beads and the first population of target nucleic acids comprise selective binding.

Optionally, one or more first type of capture primers are attached to the first plurality of beads.

Optionally, the first population of target nucleic acids contains two or more different target nucleic acids that can bind independently to first capture primers.

Optionally, first plurality of beads is attached with one or more of a first type of capture primers having the same sequence or a mixture of different sequences.

Optionally, the first type of capture primers are attached covalently to the first plurality of beads.

Optionally, the first plurality of beads is attached with one type of capture primers having the same sequence.

Optionally, the first plurality of beads do not include any second capture primers.

Optionally, the first type of capture primers include at least one unique identifier sequence.

Optionally, the target nucleic acids in the first population of target nucleic acids are bound to the first plurality of beads.

Optionally, the target nucleic acids of the first population of target nucleic acids are bound to the first plurality of beads by hybridization.

Optionally, at least two different target nucleic acids from the first population of target nucleic acids are each hybridized to a first capture primer.

Optionally, at least one region of a target nucleic acid in the first population of target nucleic acids has a sequence that is complementary to at least a region of a first or second capture primer.

Optionally, at least one region of a target nucleic acid in the first population of target nucleic acids has an identical sequence to at least a region of a first or second capture primer.

In some embodiments, the single reaction mixture does not provide compartmentalization, and the second population of target nucleic acids contains target nucleic acids having the same sequence or a mixture of different sequences.

Optionally, the second population of target nucleic acids contains two or more target nucleic acids that can bind the second plurality of beads.

Optionally, the binding between the second plurality of beads and the second population of target nucleic acids comprise selective binding.

Optionally, one or more second type of capture primers are attached to the second plurality of beads.

Optionally, the second population of target nucleic acids contains two or more different target nucleic acids that can bind independently to second capture primers.

Optionally, second plurality of beads is attached with one or more of a second type of capture primers having the same sequence or a mixture of different sequences.

Optionally, the second type of capture primers are attached covalently to the second plurality of beads.

Optionally, the second plurality of beads is attached with one type of capture primers having the same sequence.

Optionally, the second plurality of beads do not include any first capture primers.

Optionally, the second type of capture primers include at least one unique identifier sequence.

Optionally, the target nucleic acids in the second population of target nucleic acids are bound to the second plurality of beads.

Optionally, the target nucleic acids of the second population of target nucleic acids are bound to the second plurality of beads by hybridization.

Optionally, at least two different target nucleic acids from the second population of target nucleic acids are each hybridized to a second capture primer.

Optionally, at least one region of a target nucleic acid in the second population of target nucleic acids has a sequence that is complementary to at least a region of a first or second capture primer.

Optionally, at least one region of a target nucleic acid in the second population of target nucleic acids has an identical sequence to at least a region of a first or second capture primer.

Optionally, the target nucleic acids in the first population of target nucleic acids can have the same sequence or a mixture of different sequences.

Optionally, the target nucleic acids in the second population of target nucleic acids can have the same sequence or a mixture of different sequences.

Optionally, at least one target nucleic acid from the first population of target nucleic acids and at least one target nucleic acid from the second population of target nucleic have the same sequence.

Optionally, the first population of target nucleic acids and the second population of target nucleic acids do not contain any target nucleic acids with the same sequence.

Optionally, the first plurality of beads is attached with a first type of capture primers, and the second plurality of beads is attached with a second type of capture primers, and the sequences of the first type of capture primers and the second type of capture primers are the same or differ.

Optionally, the first plurality of beads includes only capture primers of the first type.

Optionally, the second plurality of beads includes only capture primers of the second type.

Optionally, the first population of beads binds selectively, via hybridization, to the first population of target nucleic acids.

Optionally, the second population of beads binds selectively, via hybridization, to the second population of target nucleic acids.

Optionally, the selective binding between the first population of beads and the first population of target nucleic acids, and between the second population of beads and the second population of target nucleic acids, occurs in a single reaction mixture.

Optionally, the selective binding between the first population of beads and the first population of target nucleic acids, and between the second population of beads and the second population of target nucleic acids, occurs in a single reaction mixture that provides no compartmentalization.

In some embodiments, the methods (and related compositions, systems, kits and apparatuses) which comprise a single reaction mixture (e.g., that does not provide compartmentalization), further includes additional primer types, including third, fourth, fifth, or more different primer types.

In some embodiments, the methods (and related compositions, systems, kits and apparatuses) which comprise a single reaction mixture (e.g., that does not provide compartmentalization, further includes any one or any combination of: additional primers (e.g., capture primer, fusion primer, and/or reverse primers), enzymes (e.g., polymerases), accessory proteins (recombinase, recombinase loading protein, single-stranded binding protein, helicase or topoisomerase), one or more nucleotides, divalent cations, binding partners and/or co-factors.

Optionally, the enzymes catalyze nucleotide incorporation (e.g., polymerase).

Optionally, the enzymes comprise accessory proteins.

Optionally, the additional primers include primers in solution or attached to a support (e.g., a bead or particle).

Optionally, the nucleotides comprise natural nucleotides or analogs thereof.

Optionally, the binding partners comprise biotin.

Optionally, the co-factors include salts, cations, ATP, phosphocreatine, magnesium, manganese, and calcium.

Optionally, the first plurality of beads of a first type, the first population of target nucleic acids, the second plurality of beads of a second type, and the second population of target nucleic acids, are contained in a single reaction mixture.

Optionally, the single reaction mixture comprises an amplification reaction mixture.

Optionally, the first plurality of beads of a first type, the first population of target nucleic acids, the second plurality of beads of a second type, and the second population of target nucleic acids, are contained in a single reaction vessel.

In some embodiments, the disclosure relates generally to methods, as well as related, systems, compositions, kits and apparatuses, for synthesizing nucleic acids by (a) providing a single reaction mixture containing (i) a plurality of beads of a first type, (ii) a plurality of beads of a second type, (iii) a first population of target nucleic acids, and (iv) a second population of target nucleic acids; (b) forming a first amplified population of nucleic acids by amplifying one or more target nucleic acids of the first population; and (c) forming a second amplified population of nucleic acids by amplifying one or more target sequences from the second population of target nucleic acids, where the single reaction mixture provides compartmentalization or partitioning.

In some embodiments, the disclosure relates generally to methods, as well as related, systems, compositions, kits and apparatuses, for synthesizing nucleic acids by (a) providing a single reaction mixture that includes an emulsion, the single reaction mixture containing (i) a plurality of beads of a first type, (ii) a plurality of beads of a second type, (iii) a first population of target nucleic acids, and (iv) a second population of target nucleic acids; (b) forming a first amplified population of nucleic acids by amplifying one or more target nucleic acids of the first population; and (c) forming a second amplified population of nucleic acids by amplifying one or more target sequences from the second population of target nucleic acids.

In some embodiments, the single reaction mixture provides at least one compartment that contains at least two different types of beads and at least two different types of target nucleic acids. For example, the single reaction mixture has at least one compartment that contains (1) a first plurality of beads of a first type and a second plurality of beads of a second type, and (2) a first population of target nucleic acids and a second population of target nucleic acids. Optionally, the at least one compartment can contain additional different types of beads and additional different types of target nucleic acids.

In some embodiments, in the methods for synthesizing nucleic acids, the single reaction mixture contains an emulsion that provides compartmentalization or partitioning.

Optionally, the emulsion comprises a discontinuous hydrophilic phase and a continuous hydrophobic phase.

Optionally, the discontinuous hydrophilic phase is surrounded by the continuous hydrophobic phase.

Optionally, the emulsion comprises at least one hydrophilic phase compartment (e.g., droplet or micro-reactor) surrounded by a continuous hydrophobic phase.

Optionally, the discontinuous hydrophilic phase provides a compartment.

Optionally, the emulsion comprises a plurality of hydrophilic phase droplets and a continuous hydrophobic phase.

Optionally, the emulsion comprises a plurality of aqueous droplets and a continuous hydrophobic phase.

Optionally, the emulsion comprises at least one aqueous droplet.

Optionally, the at least one aqueous droplet includes one or more beads.

Optionally, the at least one aqueous droplet includes one or more different target nucleic acids.

Optionally, the emulsion includes at least one aqueous droplet that includes one or more beads of the first type, the second type, or beads of both the first and second type.

Optionally, the emulsion includes at least one aqueous droplet that includes one or more different target nucleic acids, including the first population, the second population, or both the first and second populations of target nucleic acids.

In some embodiments, the emulsion comprises two immiscible liquid phases. In some embodiments, two immiscible liquid phases are mixed together to make the emulsion. In some embodiments, one of the liquid phases is dispersed in the other. Optionally, the emulsion comprises a mixture of an aqueous liquid and a water-immiscible organic liquid. Optionally, the emulsion comprises at least one anionic, cationic or non-ionic surfactant. Optionally, the emulsion can have a droplet-type dispersion comprising oil-in-water, water-in-oil, or a bicontinuous microemulsion.

In some embodiments, the water immiscible organic liquid comprises an oil. In some embodiments, the oil can be from a natural source, including animal (e.g., tallow or lard), fish (e.g., fish oil), shark, seeds, nuts or plants (e.g., vegetable oils). Optionally, the oil can be from derived from petroleum, including mineral oils. Optionally, the oil comprises a fluorochemical oil, polyalphaolefin or ester oil.

In some embodiments, the surfactant includes small molecule surfactants, polymeric surfactants, triblock co-polymer surfactants or non-ionic block copolymer surfactants. Optionally, the surfactant comprises a sorbitan oleate or a silicone surfactant.

Optionally, the hydrophilic phase compartment can contain at least two different types of beads. Optionally, the hydrophilic phase compartment can contain at least two different types of target nucleic acids.

Optionally, at least one hydrophilic phase compartment can contain (i) a first plurality of beads of a first type, (ii) a first population of target nucleic acids, (iii) a second plurality of beads of a second type, and (iv) a second population of target nucleic acids. Optionally, the at least one hydrophilic phase compartment can contain additional different types of beads and additional different types of target nucleic acids. Optionally, the hydrophilic phase compartment can further contain any one or any combination of: primers (e.g., capture primer, fusion primer, and/or reverse primers), enzymes (e.g., polymerases), accessory proteins (recombinase, recombinase loading protein, single-stranded binding protein, helicase or topoisomerase), one or more nucleotides, divalent cations, binding partners and/or co-factors.

Optionally, the at least one compartment (e.g., hydrophilic phase compartment) contains the first population of target nucleic acids which include target nucleic acids having the same sequence or a mixture of different sequences.

Optionally, the first population of target nucleic acids contains two or more target nucleic acids that can bind the first plurality of beads.

Optionally, the binding between the first plurality of beads and the first population of target nucleic acids comprise selective binding.

Optionally, the first plurality of beads is attached to one or more first type of capture primers.

Optionally, the first population of target nucleic acids contains two or more different target nucleic acids that can bind independently to first capture primers.

Optionally, first plurality of beads is attached with one or more of a first type of capture primers having the same sequence or a mixture of different sequences.

Optionally, the first type of capture primers are attached covalently to the first plurality of beads.

Optionally, the first plurality of beads is attached with one type of capture primers having the same sequence.

Optionally, the first plurality of beads do not include any second capture primers.

Optionally, the first type of capture primers include at least one unique identifier sequence.

Optionally, the target nucleic acids in the first population of target nucleic acids are bound to the first plurality of beads.

Optionally, the target nucleic acids of the first population of target nucleic acids are bound to the first plurality of beads by hybridization.

Optionally, at least two different target nucleic acids from the first population of target nucleic acids are each hybridized to a first capture primer.

Optionally, at least one region of a target nucleic acid in the first population of target nucleic acids is complementary to at least a region of a first or second capture primer.

Optionally, at least one region of a target nucleic acid in the first population of target nucleic acids has an identical sequence to at least a region of a first or second capture primer.

Optionally, the at least one compartment (e.g., hydrophilic phase compartment) contains the second population of target nucleic acids which include target nucleic acids having the same sequence or a mixture of different sequences.

Optionally, the second population of target nucleic acids contains two or more target nucleic acids that can bind the second plurality of beads.

Optionally, the binding between the second plurality of beads and the second population of target nucleic acids comprise selective binding.

In some embodiments, one or more second type of capture primers are attached to the second plurality of beads.

Optionally, the second population of target nucleic acids contains two or more different target nucleic acids that can bind independently to second capture primers.

Optionally, second plurality of beads is attached with one or more of a second type of capture primers having the same sequence or a mixture of different sequences.

Optionally, the second type of capture primers are attached covalently to the second plurality of beads.

Optionally, the second plurality of beads is attached with one type of capture primers having the same sequence.

Optionally, the second plurality of beads do not include any first capture primers.

Optionally, the second type of capture primers include at least one unique identifier sequence.

Optionally, the target nucleic acids in the second population of target nucleic acids are bound to the second plurality of beads.

Optionally, the target nucleic acids of the second population of target nucleic acids are bound to the second plurality of beads by hybridization.

Optionally, at least two different target nucleic acids from the second population of target nucleic acids are each hybridized to a second capture primer.

Optionally, at least one region of a target nucleic acid in the second population of target nucleic acids is complementary to at least a region of a first or second capture primer.

Optionally, at least one region of a target nucleic acid in the second population of target nucleic acids has an identical sequence to at least a region of a first or second capture primer.

Optionally, the at least one compartment (e.g., hydrophilic phase compartment) contains at least one target nucleic acid from the first population of target nucleic acids and at least one target nucleic acid from the second population of target nucleic with the same sequence.

Optionally, the at least one compartment (e.g., hydrophilic phase compartment) contains the first population of target nucleic acids and the second population of target nucleic acids which do not include any target nucleic acids with the same sequence.

Optionally, the first plurality of beads is attached with a first type of capture primers, and the second plurality of beads is attached with a second type of capture primers, and the sequences of the first type of capture primers and the second type of capture primers are the same or different.

Optionally, the first plurality of beads includes only capture primers of the first type.

Optionally, the second plurality of beads includes only capture primers of the second type.

Optionally, the first population of beads binds selectively, via hybridization, to the first population of target nucleic acids.

Optionally, the second population of beads binds selectively, via hybridization, to the second population of target nucleic acids.

Optionally, the selective binding occurs in the at least one compartment (e.g., hydrophilic phase compartment).

Optionally, the at least one compartment (e.g., hydrophilic phase compartment) contains additional primers, including third, fourth, fifth, or more different primer types.

In some embodiments, the disclosure relates generally to methods, as well as related, systems, compositions, kits and apparatuses, for synthesizing nucleic acids by (a) providing a single reaction mixture containing (i) a plurality of beads of a first type, (ii) a plurality of beads of a second type, (iii) a first population of target nucleic acids, (iv) a second population of target nucleic acids, and (v) any one or any combination of: additional primers (e.g., capture primer, fusion primer, and/or reverse primers), enzymes (e.g., polymerases), accessory proteins (recombinase, recombinase loading protein, single-stranded binding protein, helicase or topoisomerase), one or more nucleotides, divalent cations, binding partners and/or co-factors; (b) forming a first amplified population of nucleic acids by amplifying one or more target nucleic acids of the first population; and (c) forming a second amplified population of nucleic acids by amplifying one or more target sequences from the second population of target nucleic acids, where the single reaction mixture provides compartmentalization or partitioning.

Optionally, the enzymes catalyze nucleotide incorporation (e.g., polymerase).

Optionally, the enzymes comprise accessory proteins (e.g., recombinase, recombinase loading protein, single-stranded binding protein, helicase or topoisomerase).

Optionally, the additional primers include primers in solution or attached to at least one discrete support.

Optionally, the nucleotides comprise natural nucleotides or analogs thereof.

Optionally, the binding partners comprise biotin.

Optionally, the co-factors include salts, cations, ATP, phosphocreatine, magnesium, manganese, and calcium.

Optionally, the single reaction mixture comprises an amplification reaction mixture.

Optionally, the first plurality of beads of a first type, the first population of target nucleic acids, the second plurality of beads of a second type, and the second population of target nucleic acids, are contained in a single reaction vessel.

In some embodiments, the disclosure relates generally to methods, as well as related, systems, compositions, kits and apparatuses, for synthesizing nucleic acids comprising (a) providing a reaction mixture containing a plurality of different template nucleic acids with a plurality of different discrete supports, where the reaction mixture includes a ratio of beads-to-target nucleic acids in a volume of the reaction mixture, and (b) amplifying different target nucleic acids with different discrete supports. Optionally, the reaction mixture contains a ratio of beads-to-target nucleic acids in a reaction mixture that includes or lacks compartmentalization. Optionally, the reaction mixture is a single reaction mixture.

In some embodiments, the disclosure relates generally to methods, as well as related, systems, compositions, kits and apparatuses, where the reaction mixture contains a ratio of beads-to-target nucleic acids in a volume that includes from about an average of 1 discrete support and an average of 1 target nucleic acid per 1 mL reaction mixture to an average of about 2 discrete supports: an average of 1 target nucleic acid per 1 mL reaction mixture, or about an average of 2 discrete support and an average of 1 target nucleic acid per 1 mL reaction mixture to an average of about 5 discrete supports: an average of 1 target nucleic acid per 1 mL reaction mixture. In some embodiments, the reaction mixture includes an average beads-to-target nucleic acid ratio, which can be the average number of beads divided by the average number of nucleic acids present in a defined volume of the reaction mixture. For example, the reaction mixture optionally includes a ratio of an average of 5 discrete supports to an average of 1 target nucleic acid per 1 mL reaction mixture ("5:1 average beads-to-target nucleic acid ratio"), or a ratio of an average of 7 discrete supports to an average of 1 target nucleic acid per 1 mL ("7:1 average beads-to-target nucleic acid ratio"), or a ratio of an average of 10 discrete supports to an average of 1 target nucleic acid per 1 mL of reaction mixture ("10:1 average beads-to-target nucleic acid ratio"). In some embodiments, the reaction mixture includes an average bead-to-target nucleic acid ratio of about 1, about 5, or about 7, or about 10, or about 15, or about 25. In some embodiments, the reaction mixture includes an average bead-to-target nucleic acid ratio of from about 1 to about 10, or from 1 to 10, from 1 to 15, or from 1 to 25, or from about 1 to about 5, or from 1 to 5, or from 5 to 25, or from 5 to 15, or from 5 to 10, or from 5 to 7, or from 7 to 15, or from 7 to 10, or from 7 to 25, or from 15 to 25.

In some embodiments, the reaction mixture includes a ratio of about 10 discrete supports:1 target nucleic acid per 1 mL of reaction mixture to about 15 discrete supports:1 nucleic acid per 1 mL, or a ratio of about 15 discrete supports:1 nucleic acid per 1 mL to about 20 discrete supports:1 nucleic acid per 1 mL, or a ratio of about 20 discrete supports:1 nucleic acid per 1 mL to about 25 discrete supports:1 target nucleic acid per 1 mL, or a ratio of about 25 discrete supports:1 target nucleic acid per 1 mL to about 30 discrete supports:1 nucleic acid per 1 mL, or a ratio of about 30 discrete supports:1 target nucleic acid per 1 mL to about 50 discrete supports:1 target nucleic acid per 1 mL of reaction mixture.

Optionally, the reaction mixture contains a volume of reaction mixture and a ratio of beads-to-target nucleic acids that includes about 0.5 billion discrete supports and about 50 million target nucleic acids per 1 mL reaction mixture.

Optionally, the reaction mixture contains a volume of reaction mixture and a ratio of beads-to-target nucleic acids that includes about 1 billion discrete supports and about 100 million target nucleic acids per 1 mL reaction mixture.

Optionally, the ratio of the discrete supports to the target nucleic acids can be increased or decreased per 1 mL reaction mixture.

Optionally, the amount of discrete supports can be increased about 2- to 10-fold per 1 mL reaction mixture (e.g., increased to about 1-5 billion discrete supports per 1 mL reaction mixture).

Optionally, the amount of discrete supports can be increased about 2- to 10-fold per 1 mL reaction mixture (e.g., increased to about 2-10 billion discrete supports per 1 mL reaction mixture), or increased about 10- to 20-fold per 1 mL reaction mixture (e.g., increased to about 10-20 billion discrete supports per 1 mL reaction mixture), or increased about 20- to 30-fold per 1 mL reaction mixture (e.g., increased to about 20-30 billion discrete supports per 1 mL reaction mixture), or increased about 30- to 40-fold per 1 mL reaction mixture (e.g., increased to about 30-40 billion discrete supports per 1 mL reaction mixture), or increased about 40- to 50-fold or more per 1 mL reaction mixture (e.g., increase to about 40-50 billion discrete supports or more per 1 mL reaction mixture).

Optionally, the amount of discrete supports can be decreased about 2- to 10-fold per 1 mL reaction mixture, or decreased about 10- to 25-fold per 1 mL reaction mixture, or decreased about 25- to 50-fold per 1 mL reaction mixture.

Optionally, the amount of target nucleic acids can be increased about 2- to about 5-fold per 1 mL reaction mixture (e.g., increased to about 100-250 million target nucleic acids per 1 mL reaction mixture).

Optionally, the amount of target nucleic acids can be increased about 2- to about 5-fold per 1 mL reaction mixture (e.g., increased to about 200-500 million target nucleic acids per 1 mL reaction mixture), or increased about 5- to about 10-fold per 1 mL reaction mixture (e.g., increased to about 500-1000 million target nucleic acids per 1 mL reaction mixture), or increased about 10- to about 20-fold per 1 mL reaction mixture (e.g., increased to about 1000-2000 million target nucleic acids per 1 mL reaction mixture), or increased about 20- to about 50-fold per 1 mL reaction mixture (e.g., increased to about 2000-5000 million target nucleic acids per 1 mL reaction mixture).

Optionally, the amount of target nucleic acids can be increased up to 100-fold or more per 1 mL reaction mixture (e.g., increased to about 10,000 million target nucleic acids or more per 1 mL reaction mixture).

Optionally, the amount of target nucleic acids can be decreased about 2- to 10-fold per 1 mL reaction mixture, or decreased about 10- to 25-fold per 1 mL reaction mixture, or decreased about 25- to 50-fold per 1 mL reaction mixture.

In some embodiments, the disclosure relates generally to methods, as well as related, systems, compositions, kits and apparatuses, for synthesizing nucleic acids comprising (a) providing a single reaction mixture containing about 6 billion discrete supports and about 300-800 million target nucleic acids in about 2.4 mL reaction mixture, and (b) amplifying at least some portion of the target nucleic acids by subjecting the reaction mixture to amplification conditions. Optionally, the ratio of beads-to-target nucleic acids in the reaction mixture includes or lacks compartmentalization.

In some embodiments, the disclosure relates generally to methods, as well as related, systems, compositions, kits and apparatuses, for synthesizing nucleic acids comprising (a) providing a single reaction mixture containing between 18-24 billion discrete supports and about 1800 million target nucleic acids in a defined volume, and (b) amplifying the target nucleic acids in the reaction mixture by subjecting the reaction mixture to amplification conditions. Optionally, the defined volume of the reaction mixture is between 1 mL and 5 mL, typically between 2 and 4 mL, more typically between 2 and 3 mL. In some embodiments, the defined volume is 2.4 mL. Optionally, the reaction mixture includes or lacks compartmentalization.

In some embodiments, the disclosure relates generally to compositions, as well as related, systems, methods, kits and apparatuses, comprising at least a first plurality of beads of first type and a second plurality of beads of a second type. One skilled in the art will appreciate that the compositions, as well as related, systems, methods, kits and apparatuses, can include a third, fourth, fifth, sixth, seventh, eighth, ninth, tenth, eleventh, or more different plurality of beads.

In some embodiments, the plurality of beads can be solid, or can have an outer surface and an interior surface. The plurality of beads can be porous, semi porous or non-porous. The plurality of beads can have cavitation or pores, or can include three-dimensional scaffolds. In some embodiments, the plurality of beads can be Ion Sphere™ particles (from Ion Torrent, part of Life Technologies, Carlsbad, Calif.).

In some embodiments, the plurality of beads comprises a polymer material. For example, the plurality of beads comprise a gel, hydrogel or acrylamide polymers. In some embodiments, the plurality of beads can have any shape that is spherical, hemispherical, cylindrical, barrel-shaped, toroidal, rod-like, disc-like, conical, triangular, cubical, polygonal, tubular, wire-like or irregular.

In some embodiments, the beads can be any size that can fit into a reaction chamber. For example, the beads can be small enough to fit one bead in a reaction chamber. In some embodiments, the beads can be small enough so that more than one bead can fit in a reaction chamber. In some embodiments, the smallest cross-sectional length of a bead (e.g., diameter) can be about 50 microns or less, or about 10 microns or less, or about 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers).

In some embodiments, the beads can be attached with one or more different capture primers (e.g., oligonucleotides). In some embodiments, the beads can be attached with a plurality of one capture primers having the same sequence, or can be attached a plurality of two or more different capture primers having different sequences. In some embodiments, the beads can be attached with a plurality of at least 1,000 oligonucleotide primers, or about 1,000-10,000 oligonucleotide primers, or about, 10,000-50,000 oligonucleotide primers, or about 50,000-75,000 oligonucleotide primers, or about 75,000-100,000 oligonucleotide primers, or more.

In some embodiments, the exterior bead surface can be attached with one or more capture primers. In some embodiments, the exterior bead surface and interior scaffolds of the beads, can be attached with one or more capture primers. A bead surface (including the interior scaffold) can be coated with an acrylamide, carboxylic or amine compound for attaching a nucleic acid (e.g., capture primer). In some embodiments, an amino-modified capture primer can be attached to a bead surface that is coated with a carboxylic acid. In some embodiments, an amino-modified capture primer can be reacted with ethyl (dimethylaminopropyl) carbodiimide (EDC) or EDAC for attachment to a carboxylic acid coated surface (with or without N-hydroxysuccinimide (NETS)). A capture primer can be immobilized to an acrylamide compound coating on a bead surface. Beads can be coated with an avidin-like compound (e.g., streptavidin) for binding biotinylated capture primers.

In some embodiments, the disclosure relates generally to compositions, as well as related, systems, methods, kits and apparatuses, comprising one or more capture primers attached to a bead. In some embodiments, the compositions, as well as related, systems, methods, kits and apparatuses, comprise a first and second capture primer. In some embodiments, the compositions, as well as related, systems, methods, kits and apparatuses, comprise additional capture primers, including a third, fourth, fifth, sixth, seventh, eighth, ninth, tenth, eleventh, or more different capture primers. In some embodiments, the different capture primers have different nucleotide sequences. In some embodiments, the capture primers comprise polymers of deoxyribonucleotides, ribonucleotides, and/or analogs thereof. In some embodiments, the capture primers comprise naturally-occurring, synthetic, recombinant, cloned, amplified, or unamplified forms. In some embodiments, the capture primers comprise DNA, cDNA, RNA, chimeric RNA/DNA, or nucleic acid analogs. In some embodiments, the capture primers comprise a random or degenerate sequence. In some embodiments, at least one portion of the capture primers comprises a sequence that can hybridize with at least one portion of a target nucleic acid, or an adaptor joined to a target nucleic acid. In some embodiments, at least one portion of the capture primers comprises a sequence that can hybridize with at least one portion of a fusion primer. In some embodiments, at least one portion of the capture primers comprises a sequence that is identical or is complementary to a portion of a target nucleic acid, an adaptor, or a fusion primer. In some embodiments, the capture primers comprise single-stranded oligonucleotides. In some embodiments, the 5' or 3' end of the one or more capture primers can be attached to the bead.

In some embodiments, the 3' end of the capture primer is extendible in a primer extension reaction. Optionally, the 3' end of the capture primer includes a 3'OH group. In some embodiments, the capture primer has a blocking moiety that prevents extension in a primer extension reaction.

In some embodiments, the capture primers can be any length, including about 2-100 nucleotides, or about 5-10 nucleotides, or about 10-25 nucleotides, or about 25-40 nucleotides, or about 40-55 nucleotides, or about 55-70 nucleotides, or about 70-85 nucleotides, or about 85-100 nucleotides, or longer.

In some embodiments, the capture primers include at least one linkage or base that is resistant to degradation by an exonuclease or endonuclease. For example, the fusion primers and reverse amplification primers can include at least one phosphorothioate linkage or a 3'-3' end linkage for exonuclease resistance, or at least one 2' fluoro or 2'O-methyl modification for endonuclease resistance.

In some embodiments, the disclosure relates generally to compositions, and related methods, systems, kits and apparatuses, that also include at least one third primer. At least one portion of the third primer includes a sequence that can hybridize to at least one region of the target nucleic acids in the first population of target nucleic acids, or can hybridize to at least one region of a complementary sequence of the target nucleic acids in the first population of target nucleic acids. In some embodiments, the third primer includes a sequence that can hybridize to at least one region of the target nucleic acids in the second population of target nucleic acids, or can hybridize to at least one region of a complementary sequence of the target nucleic acids in the second population of target nucleic acids.

Optionally, the third primer is attached to a bead of the first type or the second type, or is attached to any bead. Optionally, the attachment is covalent.

Optionally, the third primer is a solution phase primer (e.g., is not attached to any bead).

Optionally, the third primer comprises a reverse primer (see 150 in FIG. 1).

Optionally, the third primer comprises a reverse amplification primer.

Optionally, the third primer includes a universal priming sequence or site.

Optionally, the third primer includes at least one unique identifier sequence.

Optionally, the third primer includes a binding partner.

Optionally, the binding partner comprises biotin.

Optionally, the 5' end of the third primer can include a sequence that is not contained in, or is not complementary to, a sequence in the target nucleic acids in the first or the second population of target nucleic acids. For example, the third primer can be a tailed primer.

In some embodiments, the third primer comprises polymers of deoxyribonucleotides, ribonucleotides, and/or analogs thereof. In some embodiments, the third primer comprises naturally-occurring, synthetic, recombinant, cloned, amplified, or unamplified forms. In some embodiments, the third primer comprises DNA, cDNA, RNA, chimeric RNA/DNA, or nucleic acid analogs. In some embodiments, the third primer comprises a random or degenerate sequence. In some embodiments, at least one portion of a third primer comprises a sequence that can hybridize with at least one portion of a target nucleic acid, or an adaptor joined to a target nucleic acid, a capture primer, or a fusion primer. In some embodiments, at least one portion of the third primer comprises a sequence that is identical or is complementary to a portion of a target nucleic acid, an adaptor, a capture primer, or a fusion primer. In some embodiments, the third primer comprises single-stranded oligonucleotides.

In some embodiments, the 3' end of the third primers is extendible in a primer extension reaction. Optionally, the 3' end of the third primer includes a 3'OH group. In some embodiments, the third primer has a blocking moiety that prevents extension in a primer extension reaction.

In some embodiments, the third primer can be any length, including about 2-100 nucleotides, or about 5-10 nucleotides, or about 10-25 nucleotides, or about 25-40 nucleotides, or about 40-55 nucleotides, or about 55-70 nucleotides, or about 70-85 nucleotides, or about 85-100 nucleotides, or longer.

In some embodiments, the third primers include at least one linkage or base that is resistant to degradation by an exonuclease or endonuclease. For example, the fusion primers and reverse amplification primers can include at least one phosphorothioate linkage or a 3'-3' end linkage for exonuclease resistance, or at least one 2' fluoro or 2'O-methyl modification for endonuclease resistance.

In some embodiments, the disclosure relates generally to compositions, and related methods, systems, kits and apparatuses, that also include a plurality of different fusion primers that comprise complementary or identical sequences of a capture primer (or a portion thereof) and a target nucleic acid (or a portion thereof). For example, the compositions (and related methods, systems, kits and apparatuses) includes a plurality of a first fusion primer (see 160 of FIG. 2) comprising sequences that are complementary or identical to at least a portion of a first capture primer (see 110 of FIG. 2), and at least a portion of a first target nucleic acid (see 120 and 140 of FIG. 2). The compositions (and related methods, systems, kits and apparatuses) includes a plurality of a second fusion primer (see 260 of FIG. 2) comprising sequences that are complementary or identical to at least a portion of a second capture primer (see 210 of FIG. 2), and at least a portion of a second target nucleic acid (see 220 and 240 of FIG. 2).

The compositions (and related methods, systems, kits and apparatuses) can further include a plurality of a third, fourth, fifth, sixth, seventh, eighth, ninth, tenth, eleventh, or more different fusion primers.

In some embodiments, the fusion primers comprise polymers of deoxyribonucleotides, ribonucleotides, and/or analogs thereof. In some embodiments, the fusion primers comprise naturally-occurring, synthetic, recombinant, cloned, amplified, or unamplified forms. In some embodiments, the fusion primers comprise DNA, cDNA, RNA, chimeric RNA/DNA, or nucleic acid analogs. In some embodiments, the fusion primers comprise a random or degenerate sequence. In some embodiments, at least one portion of the fusion primers have nucleotide sequences that are different compared to other fusion primers. In some embodiments, at least one portion of a fusion primer comprises a sequence that can hybridize with at least one portion of a target nucleic acid, or an adaptor joined to a target nucleic acid, or a capture primer. In some embodiments, at least one portion of the capture primers comprises a sequence that is identical or is complementary to a portion of a target nucleic acid, an adaptor, or a capture primer. In some embodiments, the fusion primers comprise single-stranded oligonucleotides.

In some embodiments, the fusion primers can be any length, including about 2-100 nucleotides, or about 5-10 nucleotides, or about 10-25 nucleotides, or about 25-40 nucleotides, or about 40-55 nucleotides, or about 55-70 nucleotides, or about 70-85 nucleotides, or about 85-100 nucleotides, or longer.

In some embodiments, the plurality of first fusion primers, comprise a first sequence that is complementary or identical to at least a region/portion of the first capture primers.

Figure 2:
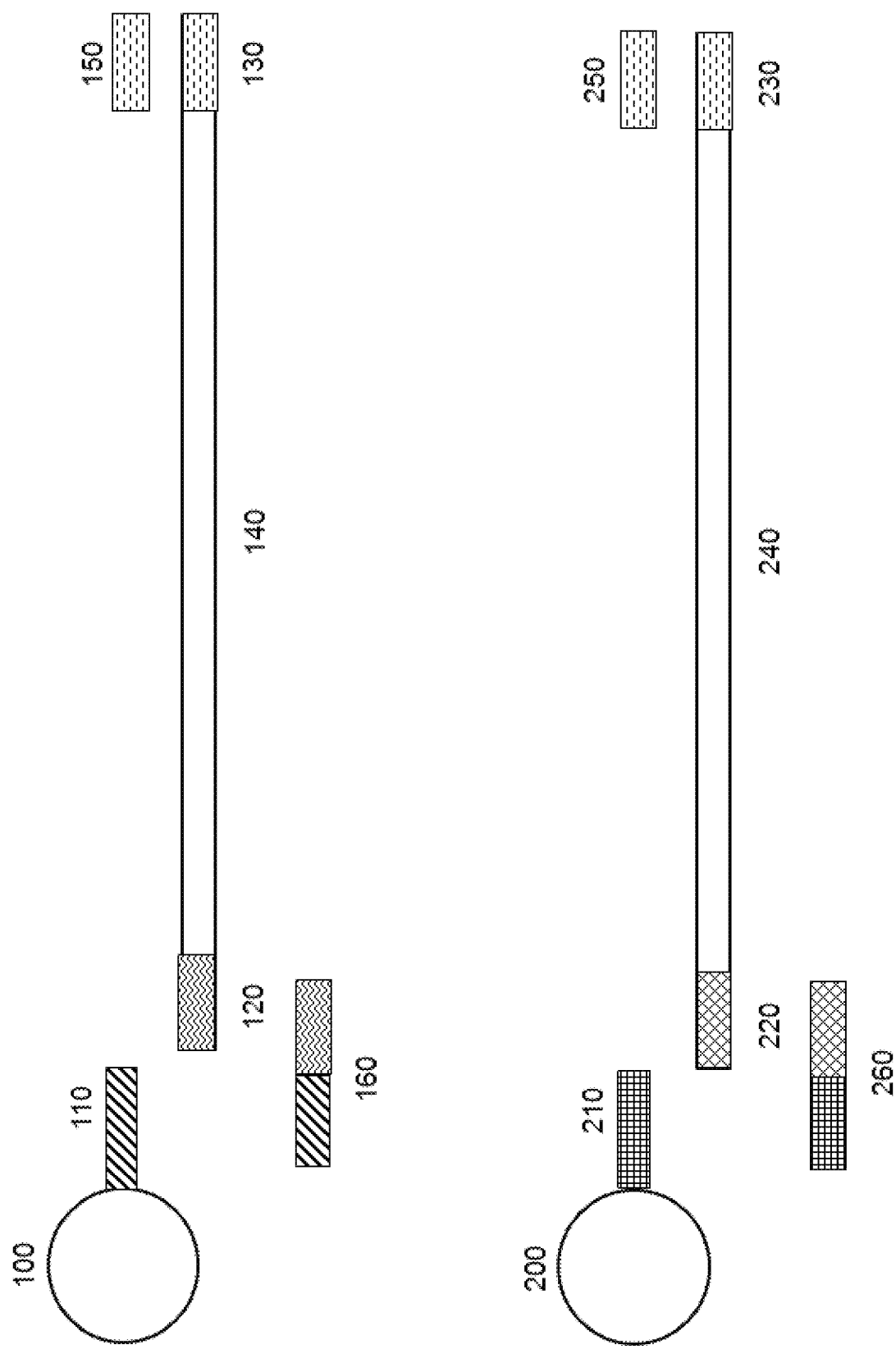
FIG. 2 is a schematic that depicts one embodiment of the compositions, as well as related, systems, methods, kits and apparatuses for nucleic acid synthesis. One bead from a first plurality of first types of beads (100) attached with a first capture primer (110), one target nucleic acid from a first population of target nucleic acids (140) that includes a first adaptor (120) and a second adaptor (130), a first reverse primer (150), and a first fusion primer (160).

Optionally, the plurality of first fusion primers further include a second sequence that is complementary or identical to at least a region/portion of a target nucleic acid in the first population of target nucleic acids (see 160 of FIG. 2).

Optionally, the second sequence that is included in the plurality of first fusion primers is complementary to at least one adaptor on a target nucleic acid (see 160 of FIG. 2).

Optionally, the first fusion primer includes at least one unique identifier sequence.

Optionally, the first fusion primer is attached to a bead. Optionally, the attachment is covalent.

Optionally, the first fusion primer is a solution phase primer (e.g., is not attached to any bead).

Optionally, the first fusion primer can include a sequence that is complementary to a capture primer and a sequence that is complementary to a portion of a target nucleic acid (e.g., an adaptor sequence) (see 160 of FIG. 2). The first fusion primer can be employed to amplify a target nucleic acid that lacks a sequence that will bind a capture primer on a bead. Optionally, the first fusion primer is a soluble primer and is not attached to a support.

In some embodiments, the compositions (and related methods, systems, kits and apparatuses) also includes a second fusion primer, comprising a first sequence that is complementary or identical to at least a region/portion of the second capture primers.

Optionally, the second fusion primer further includes a second sequence that is complementary or identical to at least a region/portion of a target nucleic acid in the second population of target nucleic acids (see 260 of FIG. 2).

Optionally, the second sequence that is included in the plurality of second fusion primers is complementary to at least one adaptor on a target nucleic acid (see 160 of FIG. 2).

Optionally, the second fusion primer includes at least one unique identifier sequence.

Optionally, the second fusion primer is attached to a bead. Optionally, the attachment is covalent.

Optionally, the second fusion primer is a solution phase primer (e.g., is not attached to any bead).

Optionally, the second fusion primer can include a sequence that is complementary to a capture primer and a sequence that is complementary to a portion of a target nucleic acid (e.g., an adaptor sequence) (see 260 of FIG. 2). The second fusion primer can be employed to amplify a target nucleic acid that lacks a sequence that will bind a capture primer on a bead. Optionally, the second fusion primer is a soluble primer and is not attached to a support.

In some embodiments, the fusion primers include at least one linkage or base that is resistant to degradation by an exonuclease or endonuclease. For example, the fusion primers and reverse amplification primers can include at least one phosphorothioate linkage or a 3'-3' end linkage for exonuclease resistance, or at least one 2' fluoro or 2'O-methyl modification for endonuclease resistance.

In some embodiments, the disclosure relates generally to compositions, as well as related, systems, methods, kits and apparatuses, comprising at least a first population of target nucleic acids and a second population of target nucleic acids. One skilled in the art will appreciate that the compositions, as well as related, systems, methods, kits and apparatuses, can include a third, fourth, fifth, sixth, seventh, eighth, ninth, tenth, eleventh, or more different populations of nucleic acids. In some embodiments, the target nucleic acids comprise single-stranded or double-stranded polynucleotides, or a mixture of both. In some embodiments, the target nucleic acids in a population of target nucleic acids, include polynucleotides having the same or different sequences. In some embodiments, the target nucleic acids in a population of target nucleic acids includes polynucleotides having the same or different lengths. In some embodiments, a population of target nucleic acids can have about 2-10, or about 10-50, or about 50-100, or about 100-500, or about 500-1,000, or about 1,000-5,000, or about $10^3$-$10^6$, or about $10^6$-$10^{10}$ or more different target nucleic acid molecules. In some embodiments, the target nucleic acids comprise polymers of deoxyribonucleotides, ribonucleotides, and/or analogs thereof. In some embodiments, the target nucleic acids comprise naturally-occurring, synthetic, recombinant, cloned, amplified, unamplified or archived (e.g., preserved) forms. In some embodiments, the target nucleic acids comprise DNA, cDNA, RNA, RNA/DNA, and nucleic acid analogs.

In some embodiments, two or more target nucleic acids in a population of target nucleic acids comprise nucleic acids having one or both ends joined to a nucleic acid adaptor. For example, the first end of a target nucleic acid can be joined to a first nucleic acid adaptor. Optionally, the second end of the target nucleic acid can be joined to a second nucleic acid adaptor. The first and second adaptors can have the same or different sequence. In some embodiments, at least a portion of the first or second nucleic acid adaptor can hybridize to the capture primer, fusion primer, reverse primer, amplification primer or sequencing primers.

In some embodiments, target nucleic acids in the population of target nucleic acids can be compatible for use in any type of sequencing platform including chemical degradation, chain-termination, sequence-by-synthesis, pyrophosphate, massively parallel, ion-sensitive, and single molecule sequencing platforms.

In some embodiments, at least one target nucleic acid in the first and the second population of target nucleic acids include one or more adaptor sequences.

In some embodiments, the target nucleic acids in the first population of target nucleic acids include a first adaptor sequence.

Optionally, at least a portion of the first adaptor sequence (see 120 of FIG. 1) is complementary or identical to a sequence within the first type of capture primer (see 110 of FIG. 1).

Optionally, the target nucleic acids in the first population of target nucleic acids further include a second adaptor sequence.

Optionally, at least a portion of the second adaptor sequence (see 130 of FIG. 1) is complementary or identical to the third primer (e.g., reverse primer) (see 150 of FIG. 1).

Optionally, the target nucleic acids in the first population of target nucleic acids include a first adaptor and a second adaptor having the same or different sequences.

In some embodiments, the target nucleic acids in the second population of target nucleic acids include a third adaptor sequence.

Optionally, at least a portion of the third adaptor sequence (see 220 of FIG. 1) is complementary or identical to a sequence within the second type of capture primer (see 210 of FIG. 1).

Optionally, the target nucleic acids in the second population of target nucleic acids further include a fourth adaptor sequence.

Optionally, at least a portion of the fourth adaptor sequence (see 230 of FIG. 1) is complementary or identical to the third primer (e.g., reverse primer) (see 250 of FIG. 1).

Optionally, the target nucleic acids in the second population of target nucleic acids include a third adaptor and a fourth adaptor having the same or different sequences.

Optionally, the first adaptors of the first population of target nucleic acids and the third adaptors of the second population of target nucleic acids have the same or different sequences.

Optionally, the second adaptors of the first population of target nucleic acids and the fourth adaptors of the second population of target nucleic acids have the same or different sequences.

Optionally, the second and fourth adaptors comprise a sequence that is a universal sequence among the first and second populations of target nucleic acids.

Optionally, any one or any combination of the first, second, third and/or fourth adaptors include at least one unique identifier sequence.

Optionally, any one or any combination of the first, second, third and/or fourth adaptors include a sequence that is identical or complementary to an amplification primer binding sequence.

Optionally, any one or any combination of the first, second, third and/or fourth adaptors include a sequence that is identical or complementary to a sequencing primer binding sequence Optionally, any one or any combination of the first, second, third and/or fourth adaptors include a binding partner.

Optionally, any one or any combination of the first, second, third and/or fourth adaptors include a sequence that is identical or complementary to an amplification primer binding sequence.

Optionally, any one or any combination of the first, second, third and/or fourth adaptors include a sequence that is identical or complementary to a sequencing primer binding sequence.

Optionally, any one or any combination of the first capture primer, second capture primer, first fusion primer, second fusion primer and/or third primer (e.g., reverse primer) includes a sequence that is identical or complementary to an amplification primer binding sequence.

Optionally, any one or any combination of the first capture primer, second capture primer, first fusion primer, second fusion primer and/or third primer (e.g., reverse primer) includes a sequence that is identical or complementary to a sequencing primer binding sequence.

In some embodiments, the disclosure relates generally to compositions, as well as related, systems, methods, kits and apparatuses, comprising target nucleic acids and at least one adaptor.

Figure 3A:
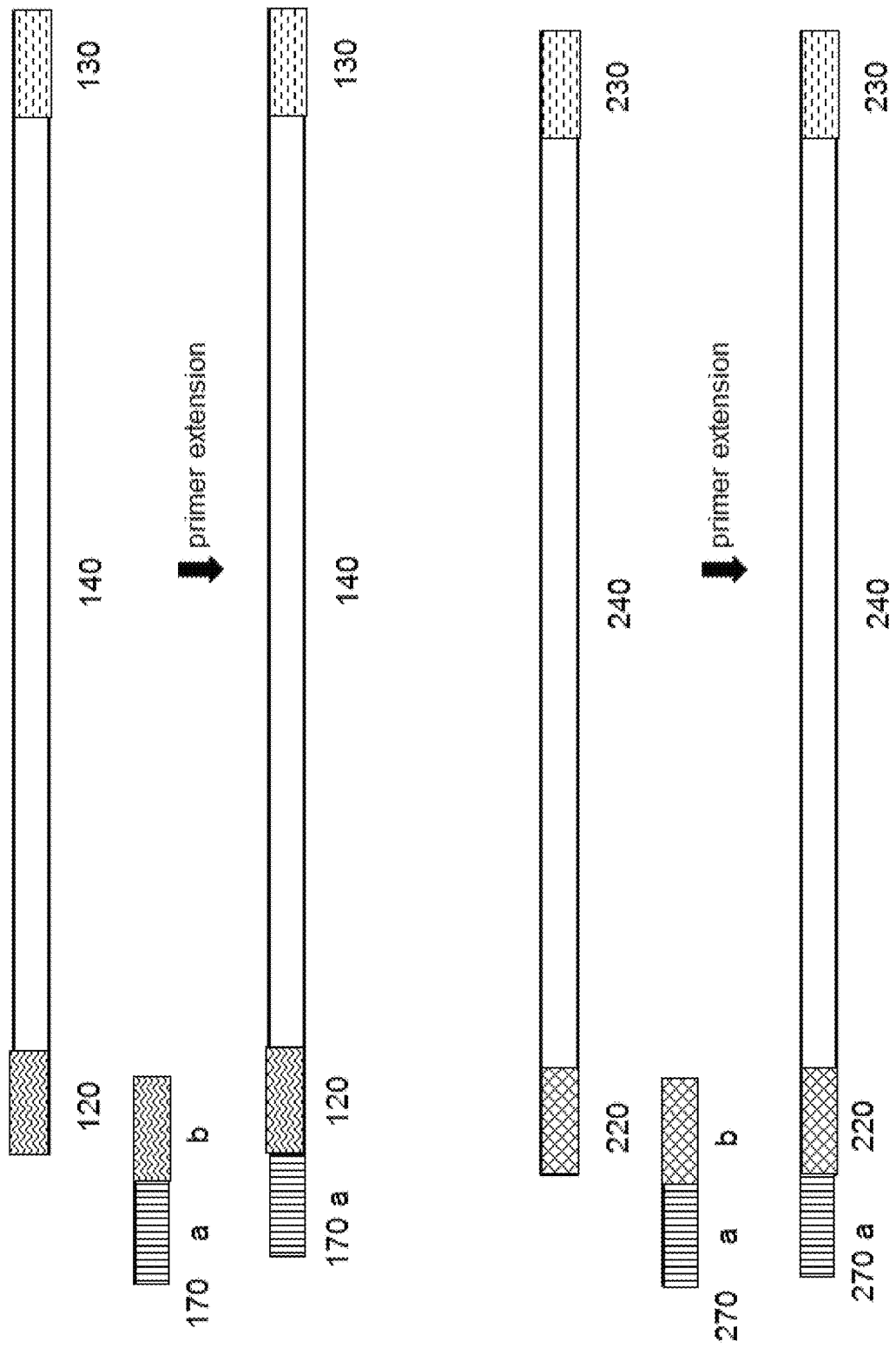
FIG. 3A is a schematic that depicts one embodiment of the compositions, as well as related, systems, methods, kits and apparatuses for nucleic acid synthesis. One target nucleic acid from a first population of target nucleic acids (140) that includes a first adaptor (120) and a second adaptor (130), and a first conversion primer (170 *a/b*) which can be a fusion primer. Optionally, the first conversion primer (170 *a/b*) includes a sequence (170*a*) that is not contained in, or is not complementary to, a portion of the first adaptor (120). In one exemplary embodiment, the first conversion primer (170 *a/b*) can be used in a primer extension reaction to append a conversion adaptor (170*a*) to the first adaptor (120) to yield a first nucleic acid molecule having sequences 170*a*, 120, 140 and 130.

In some embodiments, one or more adaptors can be joined to the target nucleic acid by ligation. In some embodiments, a tailed amplification primer can be used in a primer extension reaction (e.g., PCR reaction) to append one or more adaptors to a target nucleic acid, where the tailed amplification primer includes the sequence of one or more adaptors. For example, a tailed primer includes a first or second conversion primer (see 170 *a/b* and 270 *a/b* in FIG. 3A) which includes at least one portion having a sequence that is complementary or identical to a portion of an adaptor (e.g., see 120 and 220 in FIG. 3A) that is joined to a target nucleic acid (e.g., see 140 and 240 in FIG. 3A). Optionally, a first or second conversion primer can be used in a primer extension reaction to append a portion of the conversion primer to the target nucleic acid, or to the first or third adaptor. In another example, a tailed primer includes a first or second fusion primer (see 160 and 260 in FIGS. 2 and 3B) which includes at least one portion having a sequence that is complementary or identical to a portion of an adaptor (e.g., see 120 and 220 in FIG. 2, or 170*a* and 270*a* in FIG. 3B) that is joined to a target nucleic acid (e.g., see 140 and 240 in FIGS. 2 and 3B). In some embodiments, a tailed primer includes a first or second fusion primer (see 160 and 260 in FIGS. 2 and 3B) which includes at least one portion having a sequence that is not complementary or is not identical to a portion of an adaptor (e.g., see 120 and 220 in FIG. 2, or 170*a* and 270*a* in FIG. 3B) that is joined to a target nucleic acid (e.g., see 140 and 240 in FIGS. 2 and 3B). Optionally, a first or second fusion primer can be used in a primer extension reaction to append a portion of the fusion primer to the target nucleic acid, or to the first or third adaptor.

In some embodiments, the adaptor comprises a nucleic acid, including DNA, RNA, RNA/DNA molecules, or analogs thereof. In some embodiments, the adaptor can include one or more deoxyribonucleoside or ribonucleoside residues. In some embodiments, the adaptor can be single-stranded or double-stranded nucleic acids, or can include single-stranded and/or double-stranded portions. In some embodiments, the adaptor can have any structure, including linear, hairpin, forked (Y-shaped), or stem-loop.

In some embodiments, the adaptor can have any length, including fewer than 10 bases in length, or about 10-20 bases in length, or about 20-50 bases in length, or about 50-100 bases in length, or longer.

In some embodiments, the adaptor can have any combination of blunt end(s) and/or sticky end(s). In some embodiments, at least one end of the adaptor can be compatible with at least one end of a nucleic acid fragment. In some embodiments, a compatible end of the adaptor can be joined to a compatible end of a nucleic acid fragment. In some embodiments, the adaptor can have a 5' or 3' overhang end.

In some embodiments, the adaptor can have a 5' or 3' overhang tail. In some embodiments, the tail can be any length, including 1-50 or more nucleotides in length.

In some embodiments, the adaptor can include an internal nick. In some embodiments, the adaptor can have at least one strand that lacks a terminal 5' phosphate residue. In some embodiments, the adaptor lacking a terminal 5' phosphate residue can be joined to a nucleic acid fragment to introduce a nick at the junction between the adaptor and the nucleic acid fragment.

In some embodiments, the adaptor can include a nucleotide sequence that is identical or complementary to any portion of a capture primer, fusion primer, reverse primer, amplification primer, or a sequencing primer.

In some embodiments, the adaptor can include identification sequences, such as for example, a uniquely identifiable sequence (e.g., barcode sequence). In some embodiments, a barcoded adaptor can be used for constructing a multiplex library of target nucleic acids. In some embodiments, the barcoded adaptors can be appended to a target nucleic acid and used for sorting or tracking the source of the target nucleic acid. In some embodiments, one or more barcode sequences can allow identification of a particular adaptor among a mixture of different adaptors having different barcodes sequences. For example, a mixture can include 2, 3, 4, 5, 6, 7-10, 10-50, 50-100, 100-200, 200-500, 500-1000, or more different adaptors having unique barcode sequences.

In some embodiments, the adaptor can include degenerate sequences. In some embodiments, the adaptor can include one or more inosine residues.

In some embodiments, the adaptor can include at least one scissile linkage. In some embodiments, the scissile linkage can be susceptible to cleavage or degradation by an enzyme or chemical compound. In some embodiments, the adaptor can include at least one phosphorothiolate, phosphorothioate, and/or phosphoramidate linkage.

In some embodiments, the adaptor can include any type of restriction enzyme recognition sequence, including type I, type II, type IIs, type IIB, type III, type IV restriction enzyme recognition sequences, or recognition sequences having palindromic or non-palindromic recognition sequences.

In some embodiments, the adaptor can include a cell regulation sequences, including a promoter (inducible or constitutive), enhancers, transcription or translation initiation sequence, transcription or translation termination sequence, secretion signals, Kozak sequence, cellular protein binding sequence, and the like.

In some embodiments, the disclosure relates generally to compositions, as well as related, systems, methods, kits and apparatuses, comprising one or more polymerases. In some embodiments, the compositions (and related methods, systems, kits and apparatuses) includes one type, or a mixture of different types of polymerases. In some embodiments, the polymerase includes any enzyme, or fragment or subunit of thereof, that can catalyze polymerization of nucleotides and/or nucleotide analogs. In some embodiments, the polymerase requires a nucleic acid having an extendible 3' end. For example, the polymerase can require a terminal 3' OH of a nucleic acid primer to initiate nucleotide polymerization.

The polymerase comprises any enzyme that can catalyze the polymerization of nucleotides (including analogs thereof) into a nucleic acid strand. Typically but not necessarily such nucleotide polymerization can occur in a template-dependent fashion. In some embodiments, the polymerase can be a high fidelity polymerase. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide, such as, for example, a reporter enzyme or a processivity-enhancing domain. Typically, the polymerase comprises one or more active sites at which nucleotide binding and/or catalysis of nucleotide polymerization can occur. In some embodiments, the polymerase includes or lacks other enzymatic activities, such as for example, 3' to 5' exonuclease activity or 5' to 3' exonuclease activity. In some embodiments, the polymerase can be isolated from a cell, or generated using recombinant DNA technology or chemical synthesis methods. In some embodiments, the polymerase can be expressed in prokaryote, eukaryote, viral, or phage organisms. In some embodiments, the polymerase can be post-translationally modified proteins or fragments thereof.

In some embodiments, the polymerase can be a DNA polymerase and include without limitation bacterial DNA polymerases, eukaryotic DNA polymerases, archaeal DNA polymerases, viral DNA polymerases and phage DNA polymerases.

In some embodiments, the polymerase can be a replicase, DNA-dependent polymerase, primases, RNA-dependent polymerase (including RNA-dependent DNA polymerases such as, for example, reverse transcriptases), a thermo-labile polymerase, or a thermo-stable polymerase. In some embodiments, the polymerase can be any Family A or B type polymerase. Many types of Family A (e.g., *E. coli* Pol I), B (e.g., *E. coli* Pol II), C (e.g., *E. coli* Pol III), D (e.g., Euryarchaeotic Pol II), X (e.g., human Pol beta), and Y (e.g., *E. coli* UmuC/DinB and eukaryotic RAD30/xeroderma pigmentosum variants) polymerases are described in Rothwell and Watsman 2005 Advances in Protein Chemistry 71:401-440. In some embodiments, a polymerase can be a T3, T5, T7, or SP6 RNA polymerase.

In some embodiments, the polymerase comprises a heat-stable or heat-labile polymerase. In some embodiments, the polymerase comprises a low fidelity or high fidelity polymerase.

In some embodiment, the polymerase can lack 5'-3' exonuclease activity. In some embodiments, the polymerase can have strand-displacement activity.

In some embodiments, the archaeal DNA polymerase, can be, without limitation, a thermostable or thermophilic DNA polymerase such as, for example: a *Bacillus subtilis* (Bsu) DNA polymerase I large fragment; a *Thermus aquaticus* (Taq) DNA polymerase; a *Thermus filiformis* (Tfi) DNA polymerase; a Phi29 DNA polymerase; a *Bacillus stearothermophilus* (Bst) DNA polymerase; a *Thermococcus* sp. 9° N-7 DNA polymerase; a *Bacillus smithii* (Bsm) DNA polymerase large fragment; a *Thermococcus litoralis* (Tli) DNA polymerase or Vent™ (exo-) DNA polymerase (from New England Biolabs); or "Deep Vent" (exo-) DNA polymerase (New England Biolabs). In some embodiments, the polymerase comprises *E. coli* large fragment DNA polymerase I (e.g., Klenow).

In some embodiments, the disclosure relates generally to compositions, as well as related, systems, methods, kits and apparatuses, comprising at least one accessory protein. In some embodiments, the accessory protein can bind single-stranded or double-stranded nucleic acids. Optionally, the accessory protein can mediate loading other proteins (e.g., recombinase) onto a nucleic acid. Optionally, the accessory protein can unwind nucleic acid substrates, relax nucleic acids, resolve nucleic acid structures, hydrolyze nucleic acids (e.g., nuclease), disassemble complexes of nucleic acids and proteins, or disassemble nucleic acid structures. Optionally, the accessory protein can partially or fully denature a double-stranded first or second target nucleic acid. Optionally, the accessory protein can catalyze strand invasion or unwinding. Optionally, the accessory protein comprises a sliding clamp protein. Optionally, the accessory protein can mediate or catalyze its respective activity in a sequence-specific or sequence-independent manner.

In some embodiments, an accessory protein comprises a multimeric protein complex. Optionally, the multimeric protein complex comprises 2, 3, 4, 5, 6, 7, 8, or more subunits. Optionally, the multimeric accessory protein complex comprises a homo-meric or hetero-merit protein complex.

In some embodiments, the accessory protein comprises wild-type, mutant, recombinant, fusion, or fragments thereof.

In some embodiments, the accessory proteins can originate from any bacteriophage including a myoviral phage. The accessory proteins can originate from bacteriophage T2, T4, T5 or T7. The accessory proteins can originate from any prokaryote, bacteria (e.g., *E. coli*), eukaryote, or mammal (e.g., human).

In some embodiments, the accessory proteins comprise a single-stranded binding protein including myoviral gp32 (e.g., T4 or RB69), Sso SSB from *Sulfolobus solfataricus*, MjA SSB from *Methanococcus jannaschii*, or *E. coli* SSB protein.

In some embodiments, the single reaction mixture comprises a mixture of different accessory proteins that originate from the same or different species. Optionally, the single reaction mixture comprises a mixture of different accessory proteins that originate from the same or different species as a recombinase enzyme.

In some embodiment, the accessory protein comprises a single-stranded binding protein (e.g., SSB or gp32 protein), recombinase (e.g., recA or uvsX), recombinase loading protein (e.g., uvsY protein), helicase (e.g., uvsW protein), or topoisomerase.

In some embodiments, the disclosure relates generally to compositions, as well as related, systems, methods, kits and apparatuses, comprising at least one accessory protein. In some embodiments, the accessory protein comprises an enzyme that catalyzes homologous recombination. Optionally, the enzyme that catalyzes homologous recombination can form a nucleoprotein complex by binding a single-stranded oligonucleotide (e.g., a primer). Optionally, as part of a nucleoprotein complex, the homologous recombination enzyme can bind a homologous portion of at least one strand of a double-stranded target nucleic acid. Optionally, the homologous recombination enzyme can catalyze strand unwinding. Optionally, the homologous portion of the target nucleic acid can hybridize to at least a portion of the single-stranded oligonucleotide. Optionally, the homologous portion of the target nucleic acid can be partially or completely complementary to at least a portion of the single-stranded oligonucleotide.

In some embodiments, the accessory protein can catalyze strand invasion by forming a nucleoprotein complex and binding to a homologous portion of a double-stranded target nucleic acid to form a recombination intermediate having a triple-strand structure (e.g., D-loop formation).

In some embodiments, the accessory protein comprises a recombinase enzyme.

In some embodiments, the recombinase can form a nucleoprotein complex by binding a first primer (e.g., first capture primer). Optionally, the nucleoprotein complex further includes a first target nucleic acid, where a portion of the first primer hybridizes to a portion of the first target nucleic acid. Optionally, the first target nucleic acid comprises a double-stranded polynucleotide molecule. Optionally, the recombinase can partially or fully denature the double-stranded first target nucleic acid.

In some embodiments, the recombinase can form a nucleoprotein complex by binding a second primer (e.g., second capture primer). Optionally, the nucleoprotein complex further includes a second target nucleic acid, where a portion of the second primer hybridizes to a portion of the second target nucleic acid. Optionally, the second target nucleic acid comprises a double-stranded polynucleotide molecule. Optionally, the recombinase can partially or fully denature the double-stranded second target nucleic acid.

In some embodiments, the recombination enzyme comprises at least a portion of a recombinase enzyme from any organism, including bacteriophage T4 (e.g., usvX), *Escherichia coli* (e.g., recA), or human (e.g., RAD51) (U.S. Pat. No. 5,223,414 to Zarling, U.S. Pat. Nos. 5,273,881 and 5,670,316 both to Sena, and U.S. Pat. Nos. 7,270,981, 7,399,590, 7,435,561, 7,666,598, 7,763,427, 8,017,339, 8,030,000, 8,062,850, and 8,071,308).

In some embodiments, the disclosure relates generally to compositions, as well as related, systems, methods, kits and apparatuses, comprising one or more nucleotides. In some embodiments, the compositions (and related methods, systems, kits and apparatuses) includes one type, or a mixture of different types of nucleotides. A nucleotide comprises any compound that can bind selectively to, or can be polymerized by, a polymerase. Typically, but not necessarily, selective binding of the nucleotide to the polymerase is followed by polymerization of the nucleotide into a nucleic acid strand by the polymerase. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In some embodiments, one or more phosphorus atoms in the chain can be part of a phosphate group having P and O. In some embodiments, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In some embodiments, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281.

Some examples of nucleotides that can be used in the disclosed compositions (and related methods, systems, kits and apparatuses) include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof. In some embodiments, a nucleotide can include a purine or pyrimidine base, including adenine, guanine, cytosine, thymine or uracil. In some embodiments, a nucleotide includes dATP, dGTP, dCTP, dTTP and dUTP.

In some embodiments, the nucleotide is unlabeled. In some embodiments, the nucleotide comprises a label and referred to herein as a "labeled nucleotide". In some embodiments, the label can be in the form of a fluorescent dye attached to any portion of a nucleotide including a base, sugar or any intervening phosphate group or a terminal phosphate group, i.e., the phosphate group most distal from the sugar.

In some embodiments, the disclosure relates generally to compositions, as well as related, systems, methods, kits and apparatuses, comprising any one or any combination of capture primers, reverse primers, fusion primers, target nucleic acids and/or nucleotides that are non-labeled or attached to at least one label. In some embodiments, the label comprises a detectable moiety. In some embodiments, the label can generate, or cause to generate, a detectable signal. In some embodiments, the detectable signal can be generated from a chemical or physical change (e.g., heat, light, electrical, pH, salt concentration, enzymatic activity, or proximity events). For example, a proximity event can include two reporter moieties approaching each other, or associating with each other, or binding each other. In some embodiments, the detectable signal can be detected optically, electrically, chemically, enzymatically, thermally, or via mass spectroscopy or Raman spectroscopy. In some embodiments, the label can include compounds that are luminescent, photoluminescent, electroluminescent, bioluminescent, chemiluminescent, fluorescent, phosphorescent or electrochemical. In some embodiments, the label can include compounds that are fluorophores, chromophores, radioisotopes, haptens, affinity tags, atoms or enzymes. In some embodiments, the label comprises a moiety not typically present in naturally occurring nucleotides. For example, the label can include fluorescent, luminescent or radioactive moieties.

In some embodiments, the disclosure relates generally to compositions, as well as related, systems, methods, kits and apparatuses, comprising at least one member of a binding partner. In some embodiments, a binding partners includes two molecules, or portions thereof, which have a specific binding affinity for one another and typically will bind to each other in preference to binding to other molecules. In some embodiments, binding partners include an "affinity moiety" and a "receptor moiety". Typically but not necessarily some or all of the structure of one member of a specific binding pair is complementary to some or all of the structure possessed by the other member, with the two members being able to bind together specifically by way of a bond between the complementary structures, optionally by virtue of multiple non-covalent attractions.

In some embodiments, molecules that function as binding partners include: biotin (and its derivatives) and its binding partners avidin, streptavidin and their derivatives; His-tags which bind nickel, cobalt or copper; cysteine, histidine, or histidine patch which bind Ni-NTA; maltose which binds with maltose binding protein (MBP); lectin-carbohydrate binding partners; calcium-calcium binding protein (CBP); acetylcholine and receptor-acetylcholine; protein A and binding partner anti-FLAG antibody; GST and binding partner glutathione; uracil DNA glycosylase (UDG) and ugi (uracil-DNA glycosylase inhibitor) protein; antigen or epitope tags which bind to antibody or antibody fragments, particularly antigens such as digoxigenin, fluorescein, dinitrophenol or bromodeoxyuridine and their respective antibodies; mouse immunoglobulin and goat anti-mouse immunoglobulin; IgG bound and protein A; receptor-receptor agonist or receptor antagonist; enzyme-enzyme cofactors; enzyme-enzyme inhibitors; and thyroxine-cortisol. Another binding partner for biotin can be a biotin-binding protein from chicken (Hytonen, et al., BMC Structural Biology 7:8).

In some embodiments, an avidin moiety can include an avidin protein, as well as any derivatives, analogs and other non-native forms of avidin that can bind to biotin moieties. Other forms of avidin moieties include native and recombinant avidin and streptavidin as well as derivatized molecules, e.g. nonglycosylated avidins, N-acyl avidins and truncated streptavidins. For example, avidin moiety includes deglycosylated forms of avidin, bacterial streptavidins produced by *Streptomyces* (e.g., *Streptomyces avidinii*), truncated streptavidins, recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin™, Captavidin™, Neutravidin™ and Neutralite Avidin™.

In some embodiments, the disclosure relates generally to compositions, and related methods, systems, kits and apparatuses, comprising a single reaction mixture, which can be used for a nucleic acid synthesis or amplification reaction. The single reaction mixture can include primers (e.g., capture primer, fusion primer, reverse primers, and other additional primers), enzymes (e.g., polymerases), accessory proteins (e.g., recombinase, recombinase loading protein, single-stranded binding protein, helicase or topoisomerase), nucleotides, divalent cations, binding partners, co-factors and/or buffer. Optionally, the primers include any one or any combination of primers attached to a bead (e.g., immobilized primers) and/or soluble primers. Optionally, the enzymes comprise polymerases which include recombinant, fusion, mutant, heat-stable or heat labile forms. Optionally, the accessory proteins include any one or any combination of a single-stranded binding protein (e.g., SSB or gp32 protein), recombinase (e.g., recA or uvsX), recombinase loading protein (e.g., uvsY protein), helicase (e.g., uvsW protein), or topoisomerase. Optionally, the nucleotides can include compounds having structures the same as or similar to naturally-occurring nucleotides, or nucleotide analogs having derivatized base, sugar and/or phosphate groups, or labeled or non-labeled nucleotides. Optionally, the divalent cations include magnesium, manganese and/or calcium. Optionally, the binding partners include biotin and avidin-like compounds, such as avidin or streptavidin. Optionally, the buffer comprises a source of ions, such as KCl, K-acetate, $NH_4$-acetate, K-glutamate, $NH_4Cl$, or ammonium sulfate. Optionally, the buffer includes Tris, Tricine, HEPES, MOPS, ACES, MES, or inorganic buffers such as phosphate or acetate-based buffers which can provide a pH range of about 4-12. Optionally, the buffer includes chelating agents such as EDTA or EGTA. Optionally, the buffer includes dithiothreitol (DTT), glycerol, spermidine, and/or BSA (bovine serum albumin). Optionally, the buffer includes ATP.

In some embodiments, the disclosure relates generally to compositions, and related methods, systems, kits and apparatuses, comprising a nucleic acid synthesis or nucleic acid amplification reaction that can be conducted under thermocycling or isothermal conditions, or a combination of both types of conditions.

In some embodiments thermo-cycling amplification conditions comprise a nucleic acid amplification reaction mixture that is subjected to an elevated temperature for a period of time that is sufficient to denature at least about 30-95% of the double-stranded target nucleic acids, and then subjected to a lower temperature for a period of time that is sufficient to permit hybridization between the single-stranded target nucleic acids and any of the primers (e.g., capture primer, reverse primer, or fusion primer).

In some embodiments isothermal amplification conditions comprise a nucleic acid amplification reaction mixture that is subjected to a temperature variation which is constrained within a limited range during at least some portion of the amplification, including for example a temperature variation is within about 20° C., or about 10° C., or about 5° C., or about 1-5° C., or about 0.1-1° C., or less than about 0.1° C.

In some embodiments, an isothermal nucleic acid amplification reaction can be conducted for about 2, 5, 10, 15, 20, 30, 40, 50, 60 or 120 minutes, or longer.

In some embodiments, an isothermal nucleic acid amplification reaction can be conducted at about 15-30° C., or about 30-45° C., or about 45-60° C., or about 60-75° C., or about 75-90° C., or about 90-93° C., or about 93-99° C.

In some embodiments, the disclosure relates generally to methods, and related compositions, systems, kits and apparatuses, that further include an enrichment step. In some embodiments, an amplified population of nucleic acids can include an affinity moiety. For example, in conducting any of the nucleic acid synthesis methods according to the present teachings, a reverse primer that is attached to an affinity moiety (e.g., biotin) can be used to conduct an amplification reaction to produce an amplified population of nucleic acids that are attached to the affinity moiety. In some embodiments, the enrichment step comprises forming a enrichment complex by binding the affinity moiety (which is attached to the amplified population of nucleic acids) with a purification bead (e.g., paramagnetic bead) that is attached to a receptor moiety (e.g., streptavidin). An example of purification beads include MyOne™ Beads from Dynabeads, which are paramagnetic beads attached to streptavidin. In some embodiments, a magnet can be used to separate/remove the enrichment complex from amplified population of nucleic acids that lack the affinity moiety.

In some embodiments, the disclosure relates generally to methods, and related compositions, systems, kits and apparatuses that further include at least one washing step. The washing step can be conducted at any time during the method for nucleic acid synthesis. In some embodiments, a washing step can remove excess or unreacted components of the nucleic acid synthesis (e.g., amplification) or enrichment reactions.

In some embodiments, any of the nucleic acid synthesis or amplification methods, or enrichment steps, according to the present teachings, can be conducted manually or by automation. In some embodiments, the steps of (1) providing a single reaction mixture, (2) forming any of the amplified populations of nucleic acids, (3) enriching and/or (4) washing, can be conducted manually or by automation. For example, any reagents for a nucleic acid synthesis (e.g., amplification), enrichment or washing, can be deposited into, or removed from, a reaction vessel via manual or automated modes. In some embodiments, reagents for nucleic acid synthesis include, but are not limited to: beads, capture primers, reverse primers, fusion primers, target nucleic acids, enzymes, polymerases, accessory proteins, recombinases, one or more nucleotides, labels, binding partners, divalent cations, and/or co-factors.

In some embodiments, the disclosure relates generally to compositions, and related methods, systems, kits and apparatuses, comprising a single reaction vessel containing (i) a first plurality of beads of a first type, (ii) a first population of target nucleic acids, (iii) a second plurality of beads of a second type, and (iv) a second population of target nucleic acids.

In some embodiments, the compositions (and related methods, systems, kits and apparatuses), comprise (i) a first plurality of beads of a first type, (ii) a first population of target nucleic acids, (iii) a second plurality of beads of a second type, and (iv) a second population of target nucleic acids, where items (i)-(iv) are deposited into a first reaction vessel.

In some embodiments, the compositions (and related methods, systems, kits and apparatuses), further comprise (i) a third plurality of beads of a first type, (ii) a third population of target nucleic acids, (iii) a fourth plurality of beads of a second type, and (iv) a fourth population of target nucleic acids, where items (i)-(iv) are deposited into a second reaction vessel.

In some embodiments, the compositions (and related methods, systems, kits and apparatuses), comprise (i) at least two different plurality of beads of two different type, and (ii) at least two different populations of target nucleic acids, are deposited into two or more different reaction vessels.

In some embodiments, the reaction vessel includes a tube (e.g., Eppendorf™ tube), inner wall of a tube, well, reaction chamber, groove, channel reservoir, flowcell, In some embodiments, two or more reaction vessels can be two or more reaction chambers arranged in an array. In some embodiments, the array can include one or more reaction chambers a solid surface. A reaction chamber can have walls that define width and depth. The dimensions of a reaction chamber can be sufficient to permit deposition of reagents or for conducting reactions. A reaction chamber can have any shape including cylindrical, polygonal or a combination of different shapes. Any wall of a reaction chamber can have a smooth or irregular surface. A reaction chamber can have a bottom with a planar, concave or convex surface. The bottom and side walls of a reaction chamber can comprise the same or different material and/or can be coated with a chemical group that can react with a biomolecule such as nucleic acids, proteins or enzymes.

In some embodiments, the reaction chamber can be one of multiple reaction chambers arranged in a grid or array. An array can include two or more reaction chambers. Multiple reaction chambers can be arranged randomly or in an ordered array. An ordered array can include reaction chambers arranged in a row, or in a two-dimensional grid with rows and columns.

An array can include any number of reaction chambers for depositing reagents and conducting numerous individual reactions. For example, an array can include at least 256 reaction chambers, or at least 256,000, or at least 1-3 million, or at least 3-5 million, or at least 5-7 million, or at least 7-9 million, at least 9-11 million, at least 11-13 million reaction chambers, or even high density including 13-700 million reaction chambers or more. Reaction chambers arranged in a grid can have a center-to-center distance between adjacent reaction chambers (e.g., pitch) of less than about 10 microns, or less than about 5 microns, or less than about 1 microns, or less than about 0.5 microns.

An array can include reaction chambers having any width and depth dimensions. For example, a reaction chamber can have dimensions to accommodate a single microparticle (e.g., microbead) or multiple microparticles. A reaction chamber can hold 0.001-100 picoliters of aqueous volume.

In some embodiments, at least one reaction vessel (e.g., at least one reaction chamber) can be coupled to one or more sensors or can be fabricated above one or more sensors. A reaction chamber that is coupled to a sensor can provide confinement of reagents deposited therein so that products from a reaction can be detected by the sensor. A sensor can detect changes in products from any type of reaction, including any nucleic acid reaction such as primer extension, amplification or nucleotide incorporation reactions, within the reaction vessel. A sensor can detect changes in ions (e.g., hydrogen ions), protons, phosphate groups such as pyrophosphate groups. A sensor can detect at least one by product of nucleotide incorporation, including pyrophosphate, hydrogen ions, charge transfer, or heat. In some embodiments, at least one reaction chamber can be coupled to one or more field effect transistor (FET), including for example an ion sensitive field effect transistor (ISFET). Examples of an array of reaction chambers coupled to ISFET sensors can be found at U.S. Pat. No. 7,948,015, and U.S. Ser. No. 12/002,781, hereby incorporated by reference in their entireties. Other examples of sensors that detect byproducts of a nucleotide incorporation reaction can be found, for example, in Pourmand et al, Proc. Natl. Acad. Sci., 103: 6466-6470 (2006); Purushothaman et al., IEEE ISCAS, IV-169-172; Anderson et al, Sensors and Actuators B Chem., 129: 79-86 (2008); Sakata et al., Angew. Chem. 118:2283-2286 (2006); Esfandyapour et al., U.S. Patent Publication No. 2008/01666727; and Sakurai et al., Anal. Chem. 64: 1996-1997 (1992).

In some embodiments, the disclosure relates generally to method, and related compositions, systems, kits and apparatuses, which further include a sequencing reaction. In some embodiments, any target nucleic acid that has been amplified according to the present teachings can be sequenced.

In some embodiments, the disclosure relates generally to methods, as well as related, systems, compositions, kits and apparatuses, for synthesizing nucleic acids which further comprise sequencing one or more nucleic acids in the first amplified population, or sequencing one or more nucleic acids in the second amplified population, or sequencing one or more nucleic acids in both the first and second amplified populations of target nucleic acids.

In some embodiments, any type of sequencing platform can be employed, including: sequencing by oligonucleotide probe ligation and detection (e.g., SOLiD™ from Life Technologies, WO 2006/084131), probe-anchor ligation sequencing (e.g., Complete Genomics™ or Polonator™), sequencing-by-synthesis (e.g., Genetic Analyzer and HiSeq™, from Illumina), pyrophosphate sequencing (e.g., Genome Sequencer FLX from 454 Life Sciences), ion-sensitive sequencing (e.g., Personal Genome Machine (PGM™) and Ion Proton™ Sequencer, both from Ion Torrent Systems, Inc.), and single molecule sequencing platforms (e.g., HeliScope™ from Helicos™).

In some embodiments, nucleic acids that have been synthesized, or have been amplified, according to the present teachings can be sequenced by any sequencing method, including sequencing-by-synthesis, ion-based sequencing involving the detection of sequencing byproducts using field effect transistors (e.g., FETs and ISFETs), chemical degradation sequencing, ligation-based sequencing, hybridization sequencing, pyrophosphate detection sequencing, capillary electrophoresis, gel electrophoresis, next-generation, massively parallel sequencing platforms, sequencing platforms that detect hydrogen ions or other sequencing byproducts, and single molecule sequencing platforms. In some embodiments, a sequencing reaction can be conducted using at least one sequencing primer that can hybridize to any portion of the polynucleotide constructs, including a nucleic acid adaptor or a target polynucleotide.

In some embodiments, nucleic acid amplified according to the present teachings can be sequenced using methods that detect one or more byproducts of nucleotide incorporation. The detection of polymerase extension by detecting physicochemical byproducts of the extension reaction, can include pyrophosphate, hydrogen ion, charge transfer, heat, and the like, as disclosed, for example, in U.S. Pat. No. 7,948,015 to Rothberg et al.; and Rothberg et al, U.S. Patent Publication No. 2009/0026082, hereby incorporated by reference in their entireties. Other examples of methods of detecting polymerase-based extension can be found, for example, in Pourmand et al, Proc. Natl. Acad. Sci., 103: 6466-6470 (2006); Purushothaman et al., IEEE ISCAS, IV-169-172; Anderson et al, Sensors and Actuators B Chem., 129: 79-86 (2008); Sakata et al., Angew. Chem. 118:2283-2286 (2006); Esfandyapour et al., U.S. Patent Publication No. 2008/01666727; and Sakurai et al., Anal. Chem. 64: 1996-1997 (1992).

Reactions involving the generation and detection of ions are widely performed. The use of direct ion detection methods to monitor the progress of such reactions can simplify many current biological assays. For example, template-dependent nucleic acid synthesis by a polymerase can be monitored by detecting hydrogen ions that are generated as natural byproducts of nucleotide incorporations catalyzed by the polymerase. Ion-sensitive sequencing (also referred to as "pH-based" or "ion-based" nucleic acid sequencing) exploits the direct detection of ionic byproducts, such as hydrogen ions, that are produced as a byproduct of nucleotide incorporation. In one exemplary system for ion-based sequencing, the nucleic acid to be sequenced can be captured in a microwell, and nucleotides can be flowed across the well, one at a time, under nucleotide incorporation conditions. The polymerase incorporates the appropriate nucleotide into the growing strand, and the hydrogen ion that is released can change the pH in the solution, which can be detected by an ion sensor that is coupled with the well. This technique does not require labeling of the nucleotides or expensive optical components, and allows for far more rapid completion of sequencing runs. Examples of such ion-based nucleic acid sequencing methods and platforms include the Ion Torrent PGM™ or Proton™ sequencer (Ion Torrent™ Systems, Life Technologies Corporation).

In some embodiments, target polynucleotides produced using the methods, systems and kits of the present teachings can be used as a substrate for a biological or chemical reaction that is detected and/or monitored by a sensor including a field-effect transistor (FET). In various embodiments the FET is a chemFET or an ISFET. A "chemFET" or chemical field-effect transistor, is a type of field effect transistor that acts as a chemical sensor. It is the structural analog of a MOSFET transistor, where the charge on the gate electrode is applied by a chemical process. An "ISFET" or ion-sensitive field-effect transistor, is used for measuring ion concentrations in solution; when the ion concentration (such as H+) changes, the current through the transistor will change accordingly. A detailed theory of operation of an ISFET is given in "Thirty years of ISFETOLOGY: what happened in the past 30 years and what may happen in the next 30 years," P. Bergveld, Sens. Actuators, 88 (2003), pp. 1-20.

In some embodiments, the FET may be a FET array. As used herein, an "array" is a planar arrangement of elements such as sensors or wells. The array may be one or two dimensional. A one dimensional array can be an array having one column (or row) of elements in the first dimension and a plurality of columns (or rows) in the second dimension. The number of columns (or rows) in the first and second dimensions may or may not be the same. The FET or array can comprise $10^2$, $10^3$, $10^4$, $10^5$, $10^6$, $10^7$ or more FETs.

In some embodiments, one or more microfluidic structures can be fabricated above the FET sensor array to provide for containment and/or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, and/or concentration in the given well. In some embodiments, there can be a 1:1 correspondence of FET sensors and reaction wells.

Microwells or reaction chambers are typically hollows or wells having well-defined shapes and volumes which can be manufactured into a substrate and can be fabricated using conventional microfabrication techniques, e.g. as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al, Silicon Micromachining (Cambridge University Press, 2004); and the like. Examples of configurations (e.g. spacing, shape and volumes) of microwells or reaction chambers are disclosed in Rothberg et al, U.S. patent publication 2009/0127589; Rothberg et al, U.K. patent application GB24611127.

In some embodiments, the biological or chemical reaction can be performed in a solution or a reaction chamber that is in contact with, operatively coupled, or capacitively coupled to a FET such as a chemFET or an ISFET. The FET (or chemFET or ISFET) and/or reaction chamber can be an array of FETs or reaction chambers, respectively.

In some embodiments, a biological or chemical reaction can be carried out in a two-dimensional array of reaction chambers, wherein each reaction chamber can be coupled to a FET, and each reaction chamber is no greater than 10 µm$^3$ (i.e., 1 pL) in volume. In some embodiments each reaction chamber is no greater than 0.34 pL, 0.096 pL or even 0.012 pL in volume. A reaction chamber can optionally be no greater than 2, 5, 10, 15, 22, 32, 42, 52, 62, 72, 82, 92, or 102 square microns in cross-sectional area at the top. Preferably, the array has at least $10^2$, $10^3$, $10^4$, $10^5$, $10^6$, $10^7$, $10^8$, $10^9$, or more reaction chambers. In some embodiments, at least one of the reaction chambers is operatively coupled to at least one of the FETs.

FET arrays as used in various embodiments according to the disclosure can be fabricated according to conventional CMOS fabrications techniques, as well as modified CMOS fabrication techniques and other semiconductor fabrication techniques beyond those conventionally employed in CMOS fabrication. Additionally, various lithography techniques can be employed as part of an array fabrication process.

Exemplary FET arrays suitable for use in the disclosed methods, as well as microwells and attendant fluidics, and methods for manufacturing them, are disclosed, for example, in U.S. Patent Publication No. 20100301398; U.S. Patent Publication No. 20100300895; U.S. Patent Publication No. 20100300559; U.S. Patent Publication No. 20100197507, U.S. Patent Publication No. 20100137143; U.S. Patent Publication No. 20090127589; and U.S. Patent Publication No. 20090026082, which are incorporated by reference in their entireties.

In one aspect, the disclosed methods, compositions, systems, apparatuses and kits can be used for carrying out label-free nucleic acid sequencing, and in particular, ion-based nucleic acid sequencing. The concept of label-free detection of nucleotide incorporation has been described in the literature, including the following references that are incorporated by reference: Rothberg et al, U.S. patent publication 2009/0026082; Anderson et al, Sensors and Actuators B Chem., 129: 79-86 (2008); and Pourmand et al, Proc. Natl. Acad. Sci., 103: 6466-6470 (2006). Briefly, in nucleic acid sequencing applications, nucleotide incorporations are determined by measuring natural byproducts of polymerase-catalyzed extension reactions, including hydrogen ions, polyphosphates, PPi, and Pi (e.g., in the presence of pyrophosphatase). Examples of such ion-based nucleic acid sequencing methods and platforms include the Ion Torrent PGM™ or Proton™ sequencer (Ion Torrent™ Systems, Life Technologies Corporation).

In some embodiments, the disclosure relates generally to methods for sequencing nucleic acids that have been amplified by the teachings provided herein. In one exemplary embodiment, the disclosure relates generally to a method for obtaining sequence information from polynucleotides, comprising: (a) amplifying nucleic acids; and (b) performing template-dependent nucleic acid synthesis using at least one of the amplified nucleic acids produced during step (a) as a template. The amplifying can optionally be performed according to any of the amplification methods described herein.

In some embodiments, the template-dependent synthesis includes incorporating one or more nucleotides in a template-dependent fashion into a newly synthesized nucleic acid strand.

Optionally, the methods can further include producing one or more ionic byproducts of such nucleotide incorporation.

In some embodiments, the methods can further include detecting the incorporation of the one or more nucleotides into the sequencing primer. Optionally, the detecting can include detecting the release of hydrogen ions.

In another embodiment, the disclosure relates generally to a method for sequencing a nucleic acid, comprising: (a) amplifying nucleic acids according to the methods disclosed herein; (b) disposing the amplified nucleic acids into a plurality of reaction chambers, wherein one or more of the reaction chambers are in contact with a field effect transistor (FET). Optionally, the method further includes contacting amplified nucleic acids which are disposed into one of the reaction chambers, with a polymerase thereby synthesizing a new nucleic acid strand by sequentially incorporating one or more nucleotides into a nucleic acid molecule. Optionally, the method further includes generating one or more hydrogen ions as a byproduct of such nucleotide incorporation. Optionally, the method further includes detecting the incorporation of the one or more nucleotides by detecting the generation of the one or more hydrogen ions using the FET.

In some embodiments, the detecting includes detecting a change in voltage and/or current at the at least one FET within the array in response to the generation of the one or more hydrogen ions.

In some embodiments, the FET can be selected from the group consisting of: ion-sensitive FET (isFET) and chemically-sensitive FET (chemFET).

One exemplary system involving sequencing via detection of ionic byproducts of nucleotide incorporation is the Ion Torrent PGM™ or Proton™ sequencer (Life Technologies), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™ or Proton™ sequencer detects the nucleotide incorporations by detecting the hydrogen ion byproducts of the nucleotide incorporations. The Ion Torrent PGM™ or Proton™ sequencer can include a plurality of nucleic acid templates to be sequenced, each template disposed within a respective sequencing reaction well in an array. The wells of the array can each be coupled to at least one ion sensor that can detect the release of $H^+$ ions or changes in solution pH produced as a byproduct of nucleotide incorporation. The ion sensor comprises a field effect transistor (FET) coupled to an ion-sensitive detection layer that can sense the presence of $H^+$ ions or changes in solution pH. The ion sensor can provide output signals indicative of nucleotide incorporation which can be represented as voltage changes whose magnitude correlates with the $H^+$ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of $H^+$ ions in the reaction well, along with a concomitant change in the localized pH. The release of $H^+$ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously. Further details regarding the compositions, design and operation of the Ion Torrent PGM™ or Proton™ sequencer can be found, for example, in U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617, all of which applications are incorporated by reference herein in their entireties.

EXAMPLES

Embodiments of the present teachings can be further understood in light of the following examples, which should not be construed as limiting the scope of the present teachings in any way.

Example 1

In some embodiments, the disclosure relates generally to methods, as well as related, systems, compositions, kits and apparatuses, (a) providing a plurality of different populations of target nucleic acids, and a plurality of different types of discrete supports, and (b) forming different amplified populations of the target nucleic acids that are attached to the different types of discrete supports. Four different human genomic DNA fragment libraries were prepared. The libraries contained a 200 bp insert, and included an L1 (SEQ ID NOS:11 and 12), L2 (SEQ ID NOS:13 and 14), L3 (SEQ ID NOS: 15 and 16) or L4 double-stranded adaptor (SEQ ID NOS: 17 and 18) joined at one end and a universal adaptor A joined at the other end. Four different types of beads were prepared, each type of bead covalently attached with a plurality of one type of capture primers, AV1, AV2, AV3, or AV4 (SEQ ID NOS:1-4, respectively). A 1.2 mL aqueous mixture was prepared that contained about 250 million molecules of each of the four different human libraries, and about 1.5 billion beads of each of the four types, and four different types of fusion primers (AV1_L1, AV2_L2, AV3_L3, and AV4_L4) (SEQ ID NOS:23-26, respectively), and universal reverse A primers. A water-in-oil emulsion was prepared with the 1.2 mL mixture.

A control 1.2 mL emPCR reaction mixture was prepared. The control emPCR mixture contained about 250 million molecules of one type of human library (which included a 200 bp insert) with an AV1 adapter (SEQ ID NOS:11 and 12) joined to one end, and the universal adaptor A joined at the other end, and about 6 billion of one type of bead (B beads), and B_AV1 fusion primers and universal reverse A primers.

The emPCR procedure, using thermocycling, was conducted according to manufacturer's instructions contained in the user manual Ion PI™ Template OT2 200 Kit v3 (publication No. MAN0009133).

The templated beads from each reaction were sequenced separately on an Ion Torrent™ PI chip. The sequencing data as aligned to the human genome, and the number of duplicate sequences in each set of alignments was determined. The reaction containing four bead types produced a duplicate rate of 9.4% whereas the control reaction with only one bead type produced a duplicate rate of 26.5%. Other metrics such as yield of templated beads, polyclonal percentage, and number of alignments were similar between the two conditions (see Table 1).

TABLE 1

| number of bead types | templated bead yield | percent polyclonal | alignments | duplicate rate |
|---|---|---|---|---|
| 1 | 584,000,000 | 32% | 77,220,582 | 26.5% |
| 4 | 554,000,000 | 30% | 84,950,739 | 9.4% |

Example 2

In some embodiments, the disclosure relates generally to methods, as well as related, systems, compositions, kits and apparatuses, (a) providing a plurality of different populations of target nucleic acids, and a plurality of different types of discrete supports, and (b) forming different amplified populations of the target nucleic acids that are attached to the different types of discrete supports. Four different human genomic DNA fragment libraries were prepared. The libraries contained a 200 bp insert, and included an L1 (SEQ ID NOS:11 and 12), L2 (SEQ ID NOS:13 and 14), L3 (SEQ ID NOS:15 and 16) or L4 double-stranded adaptor (SEQ ID NOS:17 and 18) joined at one end and a universal adaptor A joined at the other end. Four different types of beads were prepared, each type of bead covalently attached with a plurality of one type of capture primers, AV1, AV2, AV3, or AV4 (SEQ ID NOS:1-4, respectively). A 2.4 mL aqueous mixture was prepared that contained about 125 million molecules of each of the four different human libraries, and about 1.5 billion beads of each of the four types, and four different types of fusion primers (AV1_L1, AV2_L2, AV3_L3, and AV4_L4) (SEQ ID NOS:23-26, respectively) and universal reverse A primers. A water-in-oil emulsion was prepared with the 2.4 mL mixture.

A control 2.4 mL emPCR reaction mixture was prepared. The control emPCR mixture contained about 125 million molecules of one type of human library (which included a 200 bp insert) with an AV1 adapter (SEQ ID NOS:11 and 12) joined to one end, and the universal adaptor A joined at the other end, about 6 billion of one type of bead (B beads), and B_AV1 fusion primers and reverse universal A primers.

The emPCR procedure, using thermocycling, was conducted according to manufacturer's instructions contained in the user manual Ion PI™ Template OT2 200 Kit v3 (publication No. MAN0009133).

Typically, this emPCR reaction is conducted using 500 million molecules per bead type, which yields approximately 30% polyclonality. In this reaction, only 125 million library molecules per bead type were included in the emPCR reaction mixture.

The templated beads from each reaction were sequenced separately, aligned to the human genome, and the number of duplicate sequences in each set of alignments was determined. Both reactions produced a low number of polyclonal beads (19% and 21%, see Table 2). However, the reaction containing four bead types produced a duplicate rate of 12% whereas the control reaction with only one bead type produced a duplicate rate of 27.7%. Other metrics such as yield of templated beads and number of alignments were similar between the two conditions (see Table 2).

TABLE 2

| number of bead types | templated bead yield | percent polyclonal | alignments | duplicate rate |
|---|---|---|---|---|
| 1 | 161,000,000 | 21% | 64,993,033 | 27.7% |
| 4 | 134,000,000 | 19% | 74,452,984 | 12.0% |

Example 3

In some embodiments, the disclosure relates generally to methods, as well as related, systems, compositions, kits and apparatuses, for preparing an enriched sample containing templated beads attached to a substantially monoclonal population of one of target nucleic acids. In some embodiments, the enrichment steps are performed manually or by automation. For example, automated enrichment steps can be conducted using an Ion Torrent One Touch apparatus and kit (e.g., Ion PGM™ Template OT2 200 Kit, from Ion Torrent™ Systems, Life Technologies Corporation). Alternatively, manual enrichment steps can be conducted using the reagents and solutions from an Ion PGM™ Template OT2 200 Kit, without the OT2™ apparatus. Prepare fresh Melt-Off solution by mixing together 280 uL Tween Solution (from the Ion PGM™ Template OT2 200 Kit) and 40 uL of 1 M NaOH. Prepare fresh 3 mM SDS. Remove the Recovery Solution from the Recovery tubes, leaving approximately 100 uL in the tubes. Pool the remaining Recovery Solution into a 1.7 mL tube. Rinse the Recovery Tubes with approximately 100 uL of water, and add to the 1.7 mL tube. Bring the volume of the 1.7 mL tube to 1000 mL with water. Optionally, remove an aliquot for Guava. Split into two 1.7 mL tubes, and add 500 uL of One Touch Wash Solution to each 1.7 mL tube. Vortex the MyOne beads for about 30 seconds. Add about 100 uL of unwashed OneTouch™ beads to the 1.7 mL tubes. Vortex the 1.7 mL tubes for about 30 seconds. Incubate at room temperature for about 2 minutes. Place the tubes on a magnet (e.g., DynaMag™ from Life Technologies) for separation for about 2 minutes. Remove the supernatant and discard. Add 200 uL of the Melt-Off solution to the tubes. Vortex the tubes for about 30 seconds and centrifuge for about 2 seconds. Incubate at room temperature for about 2 minutes. Place the tubes on the magnet for about 2 minutes. Remove the supernatant (contains an enriched population of templated beads) and add to a fresh 1.7 mL tube (enrichment tube). Bring the volume of the enrichment tube to 1000 uL with water. Centrifuge for about 8 minutes at about 15,500×g to pellet the enriched population of templated beads. Remove the supernatant, leaving about 20 uL, and dispose the supernatant. Add about 180 uL of nuclease-free water to four 0.2 mL tubes. Remove about 1 uL of the enriched sample for Guava analysis. Split the enriched sample into the four 0.2 mL tubes, and bring the volume in each tube to 200 uL with water. Centrifuge the 0.2 mL tubes for about 5 minutes at about 15,500×g to pellet the enriched templated beads. Remove the supernatant and dispose, leaving the enriched templated beads in the pellet in about 10 uL liquid. To each 0.2 mL tube, add 20 uL of Annealing Buffer and 20 uL of Sequencing Buffer and mix (both buffers from an Ion Torrent™ Sequencing kit from Life Technologies). Anneal the sequencing primers by incubating in a thermocycler (using the heated lid option) at 95 degrees for 120 seconds, and 37 degrees for 120 seconds. After the annealing step, pool the samples and add 40 uL loading buffer. Load several PGM or PI Ion Torrent™ sequencing chips, and conduct the sequencing steps according to the manufacture instructions (e.g., Ion PGM™ Sequencing 200 Kit v2, catalog No. 4482006, or Ion PI™ Sequencing 200 Kit v3, catalog No. 4488315).

Example 4

Another example for the preparation of an enriched sample containing templated particles (e.g., beads) in accordance with the present disclosure may be performed using the following protocol.

Library Preparation:

For library preparation, follow the preparation workflow instructions in the Ion Xpress™ Plus gDNA Fragment Library Preparation User Guide (MAN0009847 Rev C.0) for product information, and required materials and equipment, and in Ion Xpress™ Plus gDNA Fragment Library Preparation User Guide (MAN0009847 Rev C.0) for gDNA fragmentation. Proceed with the preparation using the above instructions up until the adapter ligation and nick-repair procedure of Chapter 4, "Ligate adapters, nick-repair, and purify the ligated DNA".

Perform ligation and nick-repair as follows. In a 0.2-mL tube (e.g., PCR tube), combine the reagents as indicated in the appropriate table for non-barcoded or barcoded libraries, and mix well by pipetting up and down. For barcoded libraries, use the table below for the reaction setup up:

Reaction Setup for Barcoded Libraries

| Component | Volume by Input gDNA | |
| --- | --- | --- |
| | 50-100 ng | 1 μg |
| DNA | ~25 μL | ~25 μL |
| 10X Ligase Buffer | 10 μL | 10 μL |
| Mosaic Library Adaptors | 2 μL | 10 μL |
| Ion Xpress Barcode X | 2 μL | 10 μL |
| dNTP Mix | 2 μL | 2 μL |
| Nuclease-free Water | 49 μL | 31 μL |
| DNA Ligase | 2 μL | 4 μL |
| Nick Repair Polymerase | 8 μL | 8 μL |
| Total | 100 μL | 100 μL |

Once the tube reaction mixture outlined above has been generated, and mixed via pipetting, place the tube in a thermal cycler and thermal cycle the tube as follows:

| Stage | Temperature | Time |
| --- | --- | --- |
| Hold | 25° C. | 15 min |
| Hold | 72° C. | 5 min |
| Hold | 4° C. | Hold |

Then, transfer the entire reaction mixture to a 1.5-mL tube (e.g., Eppendorf LoBind® Tube) for the next cleanup step. For cleanup, follow the instructions in the Ion Xpress™ Plus gDNA Fragment Library Preparation (MAN0009847 Rev C.0) at Chapter 4, "Purify the adapter-ligated and nick-repaired DNA" and Chapter 5, "Size-select the unamplified library—Option 2: Size-Select the library with Pippin Prep™ instrument".

For 220-base-read libraries, from the cassette type drop-down menu using the Pippin Prep™ instrument, choose 2% Marker B No Overflow Detection. Select the Tight collection mode for each lane and then define the BP Target setting for each of 1-4 lanes used.

| Sequencing System | Library Size | BP Target Setting |
| --- | --- | --- |
| Proton | 220-base reads | 310 bp |

Define lanes 1-4 as sample lanes and 5 as the ladder lane by entering "5" in the reference lane box and selecting the Apply Reference to all Lanes button. Ensure that the "Ref Lane" value for each lane is 5. Set the run time for 1.5 hours. And then proceed to "LOAD the Sample: For 100-300-base read libraries". Once completed, quantify the library using the Ion Library Quantitation Kit (Cat. No. 4468802).

Next, perform a templating reaction using an OT2 PSP4. For the templating reaction, refer to the Ion PI™ Template OT2 200 Kit v3 User Guide (MAN0009133 Revision B.0) for production information, and required materials and equipment.

Dispense 150 μL Ion PI™ OT2 Breaking Solution into each of two tubes (e.g., Recovery Tubes). Add 4 μL of the 1 mM AV1-4 Mosaic Oligo Pool to the 150 Breaking Solution in each Recovery Tube. Install the tubes and the Ion OneTouch™ Recovery Router, then close the centrifuge lid. Follow the procedure outlined in the Ion PI™ Template OT2 200 Kit v3 User Guide (MAN0009133Revision B.0) for installation of the Ion OneTouch™ 2 Amplification Plate, disposable injector, and reagents.

Next, prepare the amplification solution as follows. Vortex the AV1-4 Ion Sphere™ Particle Mix at maximum speed for 1 minute, centrifuge for 2 seconds, pipet up and down to mix; then immediately proceed to the next step. In a 2.5-mL Reaction Tube at 15° C. to 30° C., add the following components in the designated order. Add each component, then pipette the amplification solution up and down to mix:

| Order | Reagent | Volume |
| --- | --- | --- |
| 1 | Nuclease-Free Water | 160 μL |
| 3 | 1.2x Taq LR1 Amplification Mix | 2000 μL |
| 4 | 30x Taq LR1 Enzyme | 120 μL |
| 5 | Mosaic AV1-4 Ion Sphere Mix | 100 μL |
| 6 | Mosaic Library (100 pM) | 28.8 μL |
| 7 | Fusion Primer Pool (100 uM) | 4.8 μL |
| | Total | 2400 μL |

Vortex the complete amplification solution prepared at maximum speed for 5 seconds. Proceed immediately to follow the instructions found in "Fill and install the Ion PI™ Plus Reaction Filter Assembly on the Ion OneTouch™ 2 Instrument" described in the Ion PI™ Template OT2 200 Kit v3 User Guide (MAN0009133Revision B.0).

After amplification, the template-positive particles (Ion PI™ Ion Sphere™ Particles) are recovered. Reference is made to the production, information, materials and equipment outlined in the Ion PI™ Template OT2 200 Kit v3 User Guide (MAN0009133 Revision B.0). At the end of the amplification run, follow the screen prompts to centrifuge the sample. If reaction tubes are removed at the end of the run before the Ion OneTouch™ 2 Instrument has spun the sample or has not processed the sample after 15 minutes, centrifuge the sample on the instrument as follows:

a. On the home screen of the instrument, touch Open Lid, wait until the lid clicks open, then insert the two filled Ion OneTouch™ Recovery Tubes from the run in the centrifuge rotor. Close the lid until it locks.

b. Touch Options, then touch Final Spin (see figure below), then follow the screen prompts (touch Next on the next 2 screens) until the centrifugation begins. Centrifugation of the samples takes 10 minutes.

Immediately after the centrifuge has stopped, on the instrument display, touch Open Lid, wait until the lid clicks open, then remove and discard the Ion OneTouch™ Recovery Router. Remove both Ion OneTouch™ Recovery Tubes from the instrument, and put the two Recovery Tubes in a tube rack. Some cloudiness in the tube may be observable, which is normal.

Without any intervening storage of the recovered, template-positive particles at a reduced temperature, proceed immediately to washing the template-positive particles. Label a new 1.5 mL tube (e.g., 1.5-mL Eppendorf LoBind® Tube) for the template-positive particles. Use a pipette to remove all but about 100 μL of Ion OneTouch™ Recovery Solution from each tube (e.g., Ion OneTouch™ Recovery Tube). Withdraw the supernatant from the surface and on the opposite side from the pellet. Do not disturb the pellet of template-positive particles. Resuspend the template-positive particles in the remaining Recovery Solution in each tube by pipetting the suspension up and down. Transfer the suspension from each Recovery Tube to the new labeled tube (e.g., 1.5-mL tube Eppendorf LoBind® Tube). Add 100 μL of Nuclease-free Water to each of the Recovery Tubes, then pipette each aliquot in the tube up and down to mix and recover residual particles. Transfer the 100-μL aliquot from each Recovery Tube to the new labeled tube (e.g., 1.5-mL Eppendorf LoBind® Tube) to combine the aliquots.

Bring the volume of the suspension to 1 mL with Nuclease-free Water. The template-positive particles can be stored at 2° C. to 8° C. for up to 3 days. Do not store the recovered template-positive particles in Ion OneTouch™ Recovery Solution. After storage for up to 3 days, vortex the tube of template-positive particles for 30 seconds to completely resuspend the particles, and then centrifuge the tube for 2 seconds. Take 2 uL for Qubit assay. Split the sample into total of 2-1.5 mL tubes and add 500 uL of wash solution (e.g., Ion OneTouch™ Wash Solution). Vortex e Dynabeads® MyOne™ Streptavidin C1 Beads for 30 seconds and add 100 uL unwashed e Dynabeads® MyOne™ Streptavidin C1 Beads to each tube. Vortex the tubes containing the template-positive particles and e Dynabeads for 30 Seconds and incubate at room temperature for 2 minutes. Place the tubes on a magnet (e.g., DynaMag™ from Life Technologies) and allow particles to pellet to wall of tubes. Remove supernatant without disturbing the pellet and add 1 mL Ion PI™ ES Wash Solution (W). Remove from the magnet and vortex for 30 seconds and return to the magnet for separation. Remove supernatant and dispense 200 uL freshly made melt off solution and vortex for 30 sec, quick spin and incubate at room temperature for 2 minutes. Again, place the tubes on the magnet for separation.

At this point, the enriched particles are now in supernatant, and the supernatant should not be discarded. Transfer and pool both 1.7 mL supernatants into a new, labelled 1.7 mL tube. Bring the volume of the contents of the tube to 1 mL with Nuclease free water and centrifuge for 8 minutes at 15,500×g. Bring the volume of the tube down to about 20 uL and dispense about 180 uL Nuclease free water bringing the volume to 200 uL. Pipette up and down to resuspend beads and take 2 uL for Qubit. Split samples equally across four (4) 0.2 mL tubes (e.g., PCR tubes) and bring volume to 200 ul with Nuclease free water.

At this point, sequencing can be performed as outlined in the Ion PI™ Sequencing 200 Kit v3 (MAN0009136 Revision B.0).

Example 5

Figures 4A, 4B:
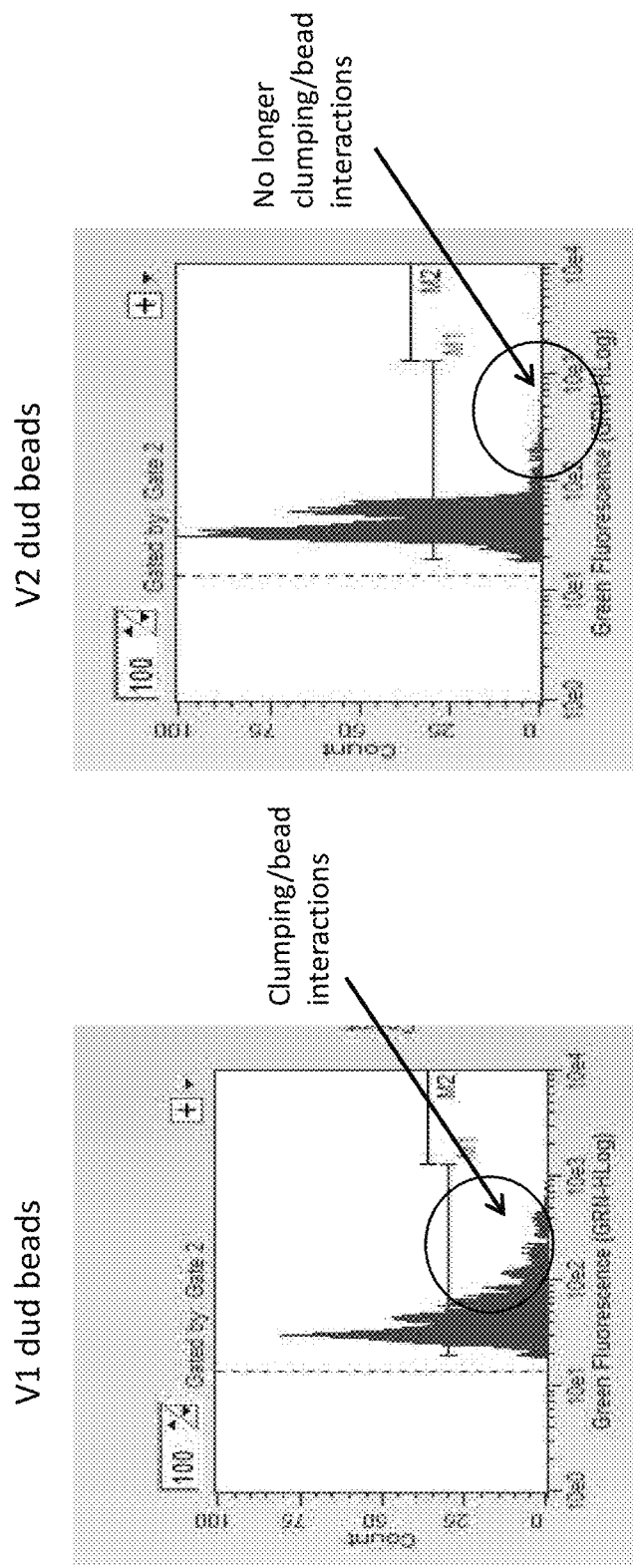
FIG. 4A shows a fluorescence profile of a first batch of templated beads prepared using four different beads attached with capture primers and their cognate adaptors, fusion primers, and reverse primers.
FIG. 4B shows a fluorescence profile of a second batch of templated beads prepared using four different beads attached with capture primers and their cognate adaptors, fusion primers, and reverse primers.

The protocol described in Example 4 (above) was used to prepare 2 batches of templated beads, and to compare bead clumping by conducting a nucleic acid synthesis reaction, in a single reaction vessel with an emulsion, using four different types of beads. In a first batch, the bead templating reaction employed a set of four different beads/capture primers and their cognate adaptors, fusion primers, and reverse primers (FIG. 4A). The first batch included capture primers AV1, AV2, AV3 and AV4 (SEQ ID NOS:1-4, respectively); double-stranded adaptors L1 (SEQ ID NOS:11 and 12), L2 (SEQ ID NOS:13 and 14), L3 (SEQ ID NOS:15 and 16) and L4 (SEQ ID NOS:17 and 18); and fusion primers AV1_L1, AV2_L2, AV3_L3, and AV4_L4) (SEQ ID NOS: 23-26, respectively). In a second batch, the bead templating reaction employed an improved set of four different beads/ capture primers and their cognate adaptors, fusion primers, and reverse primers, that were designed to decrease primer-dimer formation (FIG. 4B). The second batch include capture primers AV1, AV3, AV5 and AV6 (SEQ ID NOS:1, 3, 5 and 6, respectively); double-stranded adaptors L1 (SEQ ID NOS:11 and 12), L3 (SEQ ID NOS:15 and 16), L5 (SEQ ID NOS:19 and 20) and L6 (SEQ ID NOS:21 and 22); fusion primers AV1_L1, AV3_L3, AV5_L5 and AV6_L6 (SEQ ID NOS:23, 25, 27 and 28, respectively). The profile of templated beads was monitored using a fluorescently-labeled probe. The data in FIGS. 4A and B demonstrates that the amount of bead clumping is reduced when conducting the bead templating reaction with the improved set of primers.

Example 6

Figure 5B:
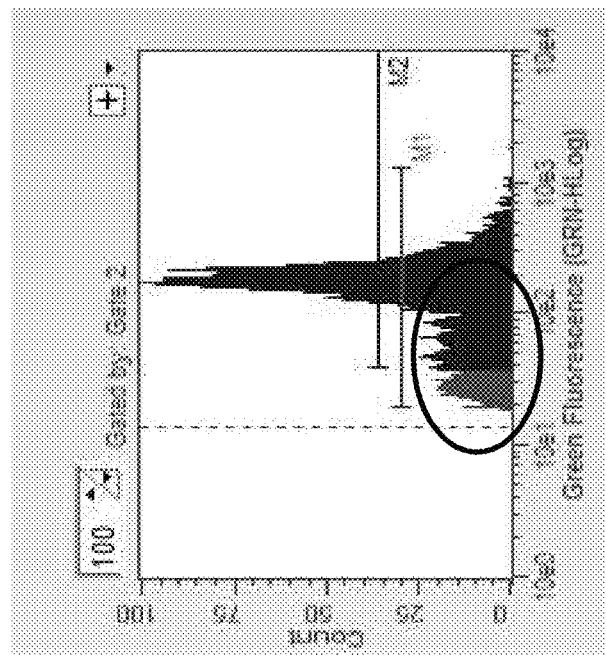
FIG. 5B shows a fluorescence profile of the same first batch of templated beads shown in FIG. 5A (enriched) prepared using four different beads attached with capture primers and their cognate adaptors, fusion primers, and reverse primers.
Figure 5A:
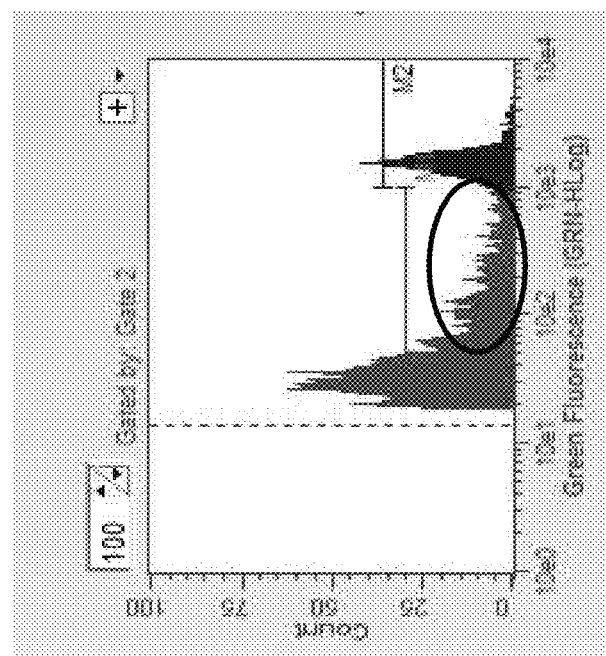
FIG. 5A shows a fluorescence profile of a first batch of templated beads (pre-enriched) prepared using four different beads attached with capture primers and their cognate adaptors, fusion primers, and reverse primers.
Figure 5D:
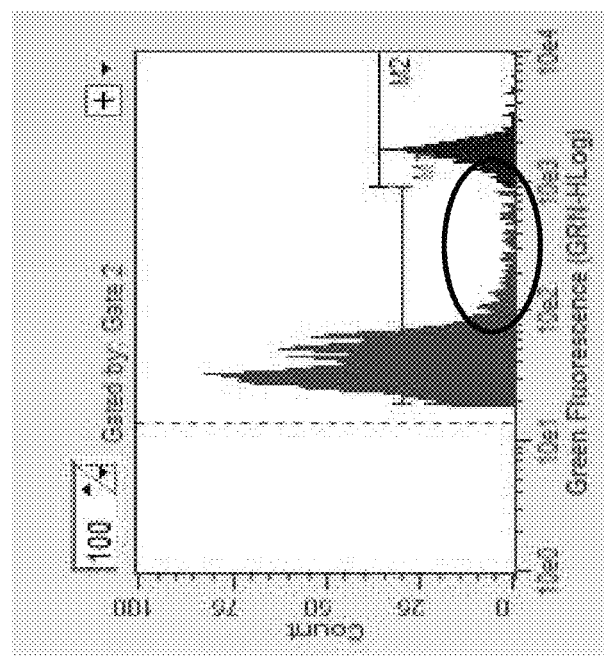
FIG. 5D shows a fluorescence profile of the same first batch of templated beads shown in FIG. 5C (enriched) prepared using four different beads attached with capture primers and their cognate adaptors, fusion primers, and reverse primers.
Figure 5C:
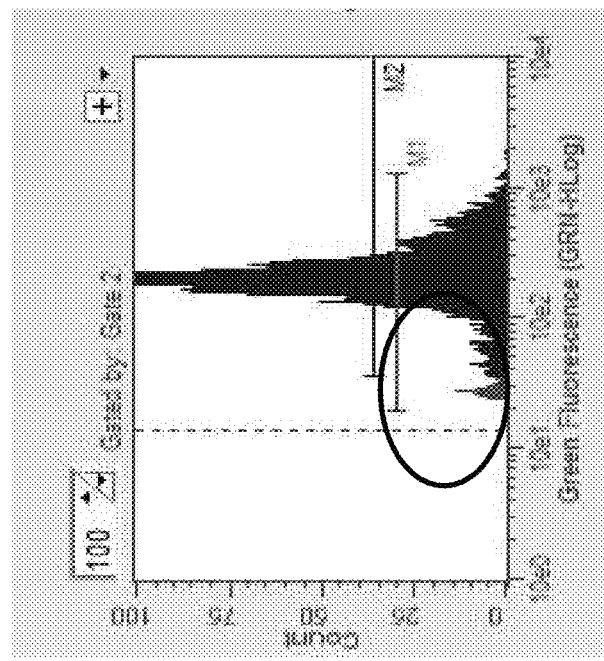
FIG. 5C shows a fluorescence profile of a second batch of templated beads (pre-enriched) prepared using four different beads attached with capture primers and their cognate adaptors, fusion primers, and reverse primers.

The protocol described in Example 4 (above) was used to prepare 2 batches of templated beads, and to compare bead clumping by conducting a nucleic acid synthesis reaction, in a single reaction vessel with an emulsion, using four different types of beads. In a first batch, the bead templating reaction employed a set of four different beads/capture primers and their cognate adaptors, fusion primers, and reverse primers (FIGS. 5A and B). The first batch included capture primers AV1, AV2, AV3 and AV4 (SEQ ID NOS:1-4, respectively); double-stranded adaptors L1 (SEQ ID NOS: 11 and 12), L2 (SEQ ID NOS:13 and 14), L3 (SEQ ID NOS:15 and 16) and L4 (SEQ ID NOS:17 and 18); and fusion primers AV1_L1, AV2_L2, AV3_L3, and AV4_L4) (SEQ ID NOS:23-26, respectively). In a second batch, the bead templating reaction employed an improved set of four different beads/capture primers and their cognate adaptors, fusion primers, and reverse primers, that were designed to decrease primer-dimer formation (FIGS. 5C and D). The second batch include capture primers AV1, AV3, AV5 and AV6 (SEQ ID NOS:1, 3, 5 and 6, respectively); double-stranded adaptors L1 (SEQ ID NOS:11 and 12), L3 (SEQ ID NOS:15 and 16), L5 (SEQ ID NOS:19 and 20) and L6 (SEQ ID NOS:21 and 22); fusion primers AV1_L1, AV3_L3, AV5_L5 and AV6_L6 (SEQ ID NOS:23, 25, 27 and 28, respectively). The profile of templated beads was monitored using a fluorescently-labeled probe. FIGS. 5A and B show pre-enriched and enriched templated beads, respectively, that were prepared using the original set of primers. FIGS. 5C and D show pre-enriched and enriched templated beads, respectively, that were prepared using the improved set of primers. The circled regions in FIGS. 5A-D indicate the poorly templated and clumped beads. The data in FIGS. 5A-D demonstrates that the amount of bead clumping is reduced when conducting the bead templating reaction with the improved set of primers.

Example 7

The protocol described in Example 4 (above) was used to prepare 4 batches of templated beads, by conducting a nucleic acid synthesis reaction, in a single reaction vessel with an emulsion, using four different types of beads and a library containing 220 bp target polynucleotides inserts from a human DNA sample (NA12878). Two batches of the resulting templated beads were combined and then loaded onto six Ion Torrent™ Proton I™ chips, and sequenced to achieve approximately 30× coverage (see Table 3 below). For example, each of the bead templating reactions contained four types of beads (AV1+AV3+AV5+AV6).

TABLE 3

|  | V2 2X OT combined Set 1 | V2 2X OT combined Set 2 |
| --- | --- | --- |
| Total aligned reads (M) | 547 M | 503 M |
| Total aligned bases (G) | 104 G | 95.3 G |
| Coverage | 33.9 X | 30.8 X |
| Polyclonality | 26% | 25% |

TABLE 3-continued

| | V2 2X OT combined Set 1 | V2 2X OT combined Set 2 |
|---|---|---|
| Low Quality | 6% | 9% |
| AQ17 mean read length | 182 | 180 |
| Duplicate rate (start + end) | 13% | 12% |

Example 8

The protocol described in Example 4 (above) was used to prepare templated beads, and to compare duplicate bead formation by conducting a nucleic acid synthesis reaction, in a single reaction vessel with an emulsion, using one, two, three and four different types of beads, and the resulting templated beads were loaded onto four Ion Torrent® Proton I™ chips, and sequenced.

Figure 6:
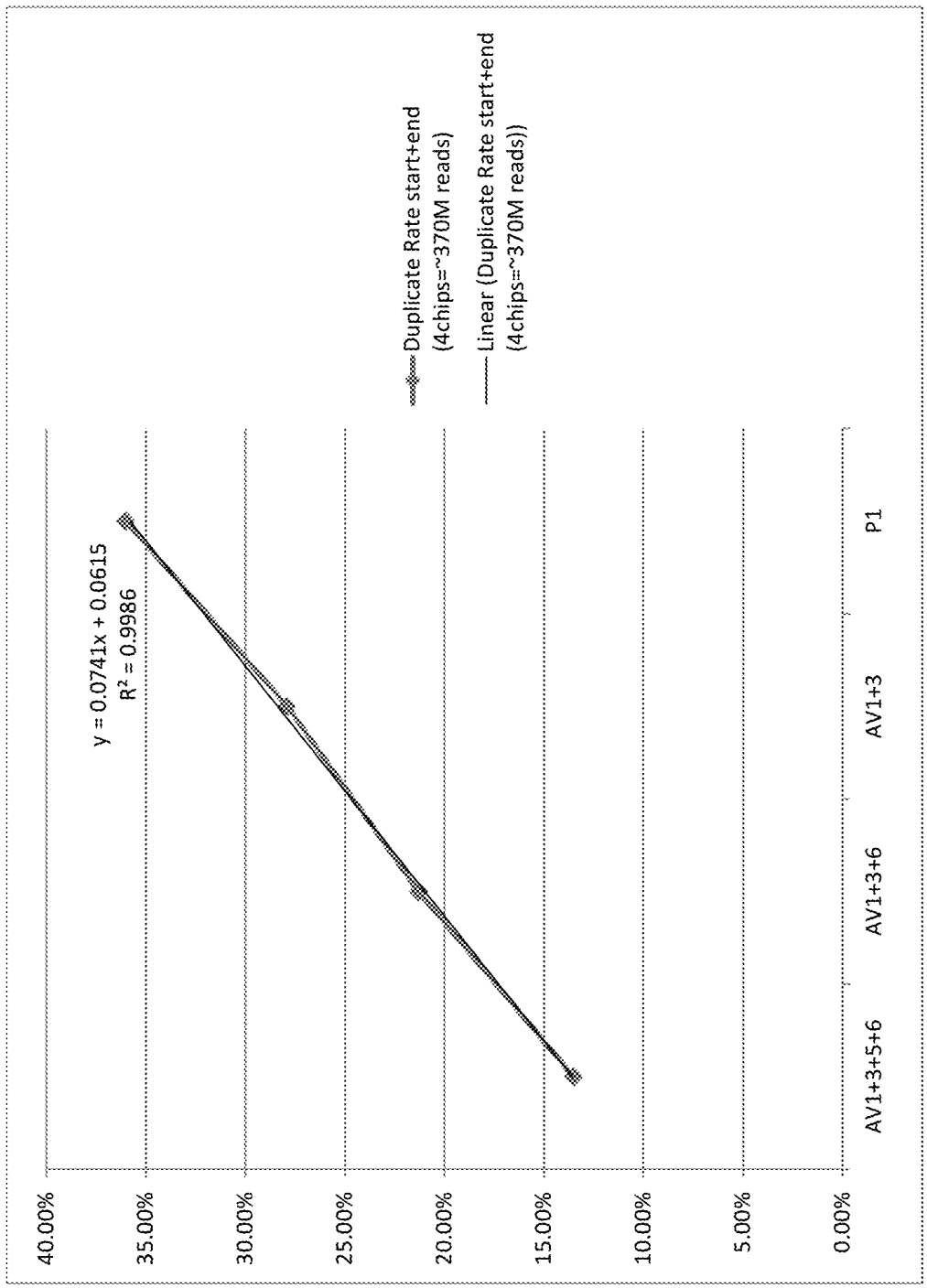
FIG. 6 is a graph showing duplicate rates of separate batches of templated beads using one, two, three or four different types of beads attached with capture primers and their cognate adaptors, fusion primers, and reverse primers.

For example, the bead templating reactions contained one type of bead (P1), two types of beads (AV1+AV3), three types of beads (AV1+AV3+AV6), and four types of beads (AV1+AV3+AV5+AV6). The data presented in Table 4 below and in FIG. 6 shows the combined duplicate rate per number of different bead types loaded onto 4 Ion Proton I™ chips per single emulsion. The bead templating reaction contained 18 billion beads and 350 million each library molecules.

TABLE 4

| Metric (merged) | AV1 + 3 + 5 + 6 | AV1 + 3 + 6 | AV1 + 3 | P1 |
|---|---|---|---|---|
| Total Reads (M) | 359 | 375 | 383 | 331 |
| Total Aligned Bases (G) | 67.1 | 70.9 | 74.3 | 56.4 |
| Duplicates (start pos) | 17% | 25% | 30% | 39% |
| Duplicates (start pos + insert end flow) | 13.5% | 21% | 28% | 36% |

The data in Table 4 and FIG. 6 demonstrate that the duplicate bead percent decreases from approximately 36% for one type of bead, to approximately 13% for four different types of beads.

Example 9

Figure 7:
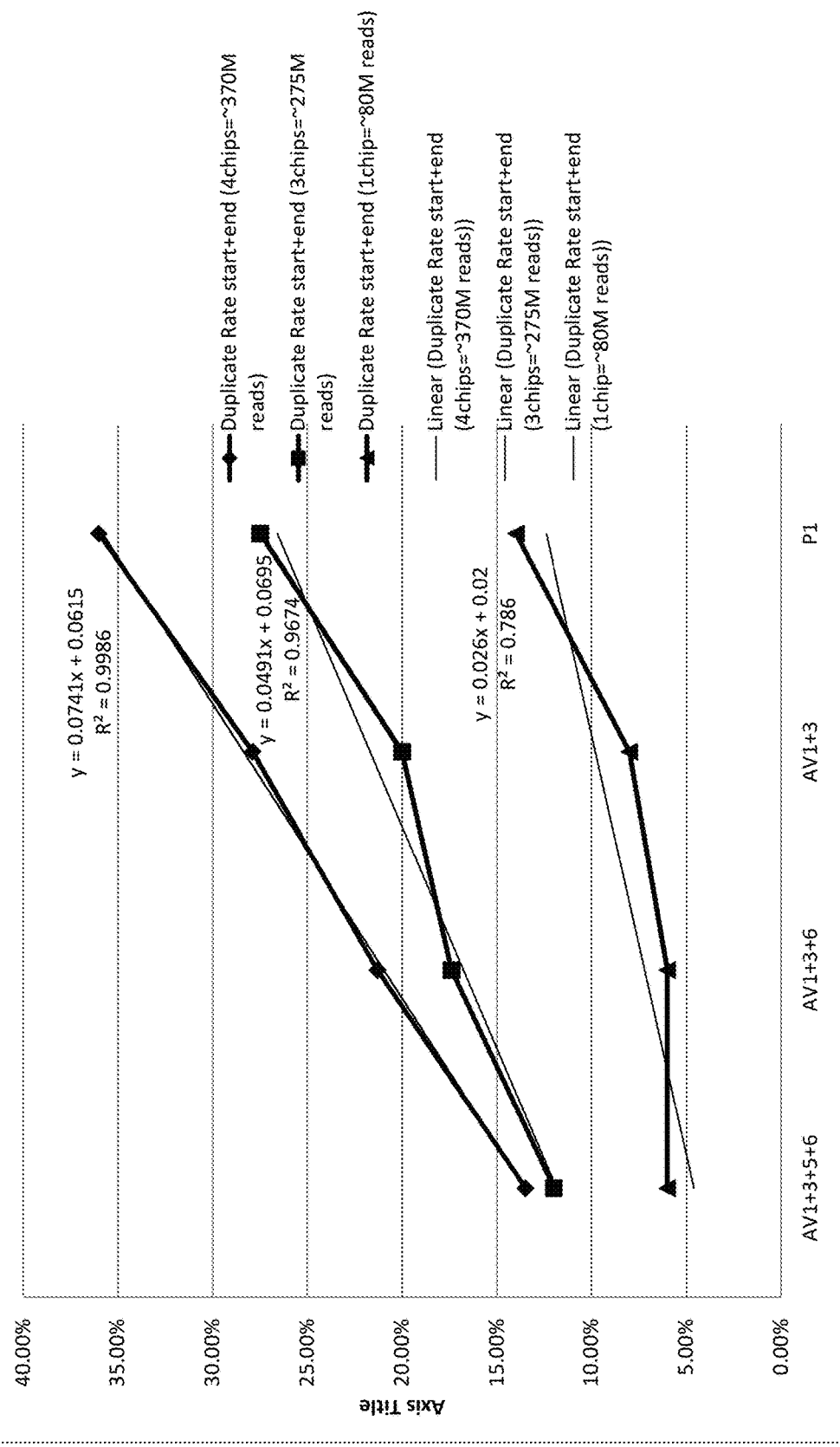
FIG. 7 is a graph showing duplicate rates of separate batches of templated beads using one, two, three or four different types of beads attached with capture primers and their cognate adaptors, fusion primers, and reverse primers. The resulting templated beads were loaded onto one, three, or four Ion Torrent™ Proton I™ chips, and sequenced.

The protocol described in Example 4 (above) was used to prepare templated beads, and to compare duplicate bead formation by conducting a nucleic acid synthesis reaction, in a single reaction vessel with an emulsion, using one, two, three and four different types of beads, and the resulting templated beads were loaded onto one, three, or four Ion Torrent™ Proton I™ chips, and sequenced (see FIG. 7). For example, the bead templating reactions contained one type of bead (P1), two types of beads (AV1+AV3), three types of beads (AV1+AV3+AV6), and four types of beads (AV1+AV3+AV5+AV6).

The graph in FIG. 7 shows duplicate bead production for bead templating reactions containing one, two, three or four different types of beads, which were loaded onto 4 Ion Proton I™ chips (♦), which yielded about 370 million reads. The (♦) represents data for duplicate bead rate (start+end) and is similar to the calculated linear duplicate rate.

The graph in FIG. 7 also shows duplicate bead production for bead templating reactions containing one, two, three or four different types of beads, which were loaded onto 3 Ion Proton I™ chips (■), which yielded about 275 million reads. The (■) represents data for duplicate bead rate (start+end) and is similar to the calculated linear duplicate rate.

The graph in FIG. 7 also shows duplicate bead production for bead templating reactions containing one, two, three or four different types of beads, which were loaded onto 1 Ion Proton I™ chip (▲), which yielded about 80 million reads. The (▲) represents data for duplicate bead rate (start+end) and is similar to the calculated linear duplicate rate.

The sequences of the capture primers, adaptors and fusion primers, that were used to conduct the experiments described in Examples 1-9 above, are listed below.

```
Bead capture primers:
AV1:
                                    (SEQ ID NO: 1)
5'-GCACACATTCAGAGTCAGCAGCTCAGCATCAT AV2:
                                    (SEQ ID NO: 2)
5'-TTAGGAGATGTTCATGCAGACTCACGATCAGT AV3:
                                    (SEQ ID NO: 3)
5'-AGTCACTTATCATCGGTGGTACGCAGCTCATT AV4:
                                    (SEQ ID NO: 4)
5'-ATTCGAGCTGTTCATCTGTATCTTGCGCTACCAA AV5:
                                    (SEQ ID NO: 5)
5'-GAATCTGTTCTCACTATTCACGCTGGAGGAGT AV6:
                                    (SEQ ID NO: 6)
5'-GTAACTCGATCAGGTCACACGACCGTTCTCAGCAT AV7:
                                    (SEQ ID NO: 7)
5'-GATTTCGCAGCTAACCTTGGTGGAAGCTCTCAT AV8:
                                    (SEQ ID NO: 8)
5'-CTTGAACTACACCACTCTGATGTGCCAGTCTA AV9:
                                    (SEQ ID NO: 9)
5'-TATCGAGCTAGTGCGTGCTATCAGAACCTATCAGT AV10:
                                    (SEQ ID NO: 10)
5'-ACGTCGACACTAGCTACCTGTCAGCTACGTGTA Library adaptors (comprising top and bottom
strands, and having phosphorothiolate,
phosphorothioate, and/or phosphoramidate
linkages (*)):
ML1a:
                                   (SEQ ID NO: 11)
5'-CCACTACGCCTCCGCTTTCCTCTCTATGGGCAGTCGGTGAAGCTCTC
ATGAT ML1b:
                                   (SEQ ID NO: 12)
5'-ATCATGAGAGCTTCACCGACTGCCCATAGAGAGGAAAGCGGAGGCGT
AGTGG*T*T ML2a:
                                   (SEQ ID NO: 13)
5'-CCACTACGCCTCCGCTTTCCTCTCTATGGGCAGTCGGTGTGCCAGTC
TAGAT
```

ML2b:
(SEQ ID NO: 14)
5'-ATCTAGACTGGCACACCGACTGCCCATAGAGAGGAAAGCGGAGGCGT
AGTGG*T*T

ML3a:
(SEQ ID NO: 15)
5'-CCACTACGCCTCCGCTTTCCTCTCTATGGGCAGTCGGTGACCTATCA
GTGAT

ML3b:
(SEQ ID NO: 16)
5'-ATCACTGATAGGTCACCGACTGCCCATAGAGAGGAAAGCGGAGGCGT
AGTGG*T*T

ML4a:
(SEQ ID NO: 17)
5'-CCACTACGCCTCCGCTTTCCTCTCTATGGGCAGTCGGTGGCTACGTG
TAGAT

ML4b:
(SEQ ID NO: 18)
5'-ATCTACACGTAGCCACCGACTGCCCATAGAGAGGAAAGCGGAGGCGT
AGTGG*T*T

ML5a:
(SEQ ID NO: 19)
5'-CCACTACGCCTCCGCTTTCCTCTCTATGGGCAGTCGGTGTGCCAGTC
TAGAT

ML5b:
(SEQ ID NO: 20)
5'-ATCTAGACTGGCACACCGACTGCCCATAGAGAGGAAAGCGGAGGCGT
AGTGG*T*T

ML6a:
(SEQ ID NO: 21)
5'-CCACTACGCCTCCGCTTTCCTCTCTATGGGCAGTCGGTGGCTACGTG
TAGAT

ML6b:
(SEQ ID NO: 22)
5'-ATCTACACGTAGCCACCGACTGCCCATAGAGAGGAAAGCGGAGGCGT
AGTGG*T*T

P1(a) adaptor:
(SEQ ID NO: 30)
5'-CCACTACGCCTCCGCTTTCCTCTCTATGGGCAGTCGGTGAT

P1(b) adaptor:
(SEQ ID NO: 31)
5'-ATCACCGACTGCCCATAGAGAGGAAAGCGGAGGCGTAGTGG*T*T

Fusion primers:
AV1/ML1:
(SEQ ID NO: 23)
5'-GCACACATTCAGAGTCAGCAGCTCAGCATCATGCAGTCGGTGAAGCT
CTCAT AV2/ML2:
(SEQ ID NO: 24)
5'-TTAGGAGATGTTCATGCAGACTCACGATCAGTGCAGTCGGTGTGCCA
GTCTA AV3/ML3:
(SEQ ID NO: 25)
5'-AGTCACTTATCATCGGTGGTACGCAGCTCATTGCAGTCGGTGACCTA
TCAGT AV4/ML4:
(SEQ ID NO: 26)
5'-ATTCGAGCTGTTCATCTGTATCTTGCGCTACCAAGCAGTCGGTGGCT
ACGTGTA AV5/ML5:
(SEQ ID NO: 27)
5'-GAATCTGTTCTCACTATTCACGCTGGAGGAGTGCAGTCGGTGTGCCA
GTCTA AV6/ML6:
(SEQ ID NO: 28)
5'-GTAACTCGATCAGGTCACACGACCGTTCTCAGCATGCAGTCGGTGGC
TACGTGTA

B/P1:
(SEQ ID NO: 29)
5'-CCTATCCCCTGTGTGCCTTGGCAGTCTCAGCCTCTCTATGGGCAGTC
GGTGAT

---

What is claimed:

1. A method of nucleic acid synthesis, comprising:
a) providing a single reaction mixture that provides compartmentalization in an emulsion containing a plurality of supports of a first type that include first capture primers; a plurality of supports of a second type that include second capture primers, wherein the sequences of the first and second capture primers are different, a first population of nucleic acids, wherein the first population of nucleic acids includes at least one nucleic acid of a first adapter type, a second population of nucleic acids, wherein the second population of nucleic acids includes at least one nucleic acid of a second adapter type, wherein the first and second adapter types are different, a first fusion primer having a first sequence portion identical to at least a portion of the first capture primer and a second sequence portion that binds to the first adapter type, and a second primer having a first sequence portion identical to at least a portion of the second capture primer and a second sequence portion that binds to the second adapter type;

b) forming a first amplified population of nucleic acids by amplifying one or more nucleic acids of the first population of nucleic acids, wherein the first amplified population of nucleic acids is attached to one or more supports of the first type; and c) forming a second amplified population of nucleic acids by amplifying one or more nucleic acids from the second population of nucleic acids, wherein the second amplified population of nucleic acids is attached to one or more supports of the second type.

2. The method of claim 1, wherein forming the first amplified population of nucleic acids and/or forming the second amplified population of nucleic acids includes amplifying a nucleic acid from the first and/or second population of nucleic acids, respectively, by PCR, isothermal or rolling circle amplification.

3. The method of claim 1, wherein the first amplified population of nucleic acids, the second amplified population of nucleic acids or both are substantially monoclonal.

4. The method of claim 1, wherein the emulsion includes a water-in-oil emulsion.

5. The method of claim 1, wherein the capture primers are not labeled.

6. The method of claim 1, wherein the single reaction mixture includes at least two, three, four, five, six, seven, eight, nine, ten, or more types of supports, and wherein each type of support includes a different capture primer.

7. The method of claim 1, further comprising sequencing one or more nucleic acids of the first amplified population and one or more nucleic acids of the second amplified population in parallel.

8. The method of claim 7, wherein the sequencing includes detection of one or more nucleotide incorporation byproducts.

9. The method of claim 7, wherein the sequencing includes detecting hydrogen ions or pyrophosphate.

10. The method of claim 1, wherein the first and second capture primers are present in about the same concentration.

11. The method of claim 1, wherein forming the first amplified population of nucleic acids includes extending the at least one nucleic acid sequence from the first population of nucleic acids to form an extended portion complementary to the first sequence portion of the first fusion primer and hybridizing the extended portion of the first population of nucleic acids to a first capture primer on the first type of supports; and forming the second amplified population of nucleic acids includes extending the at least one nucleic acid sequence from the second population of nucleic acids to form an extended portion complementary to the second sequence portion of the second fusion primer and hybridizing the extended portion of the second population of nucleic acids to a second capture primer on the second type of supports.

12. The method of claim 1, further including extending one or more first and second capture primers in a template-dependent fashion.

13. A method of amplifying a first nucleic acid sequence from a first population of nucleic acids and a first nucleic acid sequence from a second population of nucleic acids comprising:

(a) providing a single reaction mixture that provides compartmentalization in an emulsion containing a plurality of a first type of supports that include first capture primers, a plurality of a second type of supports that include second capture primers, wherein the first and second capture primers are different, a first fusion primer that includes a portion identical or complementary to the first capture primers, a second fusion primer that includes a portion identical or complementary to the second capture primers, a first population of nucleic acids, wherein the first population of nucleic acids includes at least one nucleic acid comprising sequence identical or complementary to a portion of a first fusion primer and a second population of nucleic acids, wherein the second population of nucleic acids includes at least one nucleic acid comprising sequence identical or complementary to a portion of a second fusion primer;

(b) forming a first amplified population of a first nucleic acid sequence from the first population of nucleic acids on the first type of supports using the first fusion primer; and (c) forming a second amplified population of the first nucleic acid sequence from the second population of nucleic acids on the second type of supports using the second fusion primer.

14. The method of claim 13, wherein the first amplified population, the second amplified population or both are substantially monoclonal.

15. The method of claim 13, wherein the first amplified population of nucleic acids, the second amplified population of nucleic acids, or both, are substantially monoclonal.

16. The method of claim 13, wherein the amplifying includes PCR, isothermal or rolling circle amplification.

17. The method of claim 13, wherein the emulsion includes a water-in-oil emulsion.

18. The method of claim 13, wherein the first amplified population of nucleic acids is covalently bound to one or more supports of the first plurality of supports and/or the second amplified population of nucleic acids is covalently bound to one or more supports of the second plurality of supports.

19. The method of claim 13, wherein the single reaction mixture further includes at least two, three, four, five, six, seven, eight, nine, ten, or more types of supports, each type of support including a different type of capture sequence.

20. The method of claim 13, further comprising sequencing one or more nucleic acids of the first amplified population and one or more nucleic acids of the second amplified population in parallel.

* * * * *